US005861424A

United States Patent [19]
Chen et al.

[11] Patent Number: 5,861,424
[45] Date of Patent: Jan. 19, 1999

[54] COMPOSITION AND METHOD FOR TREATING CANCER

[75] Inventors: Lan Bo Chen, Lexington, Mass.; Tadao Shishido, Kanagawa-Ken, Japan

[73] Assignees: Dana Farber Cancer Institute, Boston, Mass.; Fuji Photo Film Co., Ltd., Kanagawa, Japan

[21] Appl. No.: 478,582

[22] Filed: Jun. 7, 1995

Related U.S. Application Data

[63] Continuation of Ser. No. 974,480, Nov. 12, 1992, abandoned, which is a continuation-in-part of Ser. No. 692,347, Apr. 26, 1991, abandoned.

[51] Int. Cl.⁶ .................................................. A61K 31/425
[52] U.S. Cl. ......................... 514/366; 514/314; 514/338; 514/367; 514/369; 514/375; 514/376
[58] Field of Search ..................................... 514/439, 314, 514/338, 366, 367, 369, 375, 376

[56] References Cited

U.S. PATENT DOCUMENTS

| | | | |
|---|---|---|---|
| 2,388,963 | 11/1945 | Fry et al. | 260/240 |
| 2,454,629 | 11/1948 | Brovker | 548/156 X |
| 2,504,468 | 4/1950 | Thompson | 548/156 X |
| 2,961,318 | 11/1960 | Jones | 548/151 X |

FOREIGN PATENT DOCUMENTS

| | | |
|---|---|---|
| 028625 | 10/1988 | European Pat. Off. . |
| 55-31024 | 3/1960 | Japan . |
| 54-151133 | 11/1979 | Japan . |
| 55-69513 | 5/1980 | Japan . |
| 55-100318 | 7/1980 | Japan . |
| 154325 | 11/1989 | Japan . |
| 390025 | 4/1991 | Japan . |
| 487051 | 6/1938 | United Kingdom . |
| 489335 | 7/1938 | United Kingdom . |

OTHER PUBLICATIONS

E.B. Knott, *J. Chem. Soc.*, 949 (1955).
E.B. Knott, *J. Chem. Soc.*, 4672 (1952).

Primary Examiner—Richard L. Raymond

Attorney, Agent, or Firm—Sughrue, Mion, Zinn, Macpeak, and Seas.

[57] ABSTRACT

A pharmaceutical composition for treatment of cancer in a mammal comprising:

(A) a therapeutically effective amount of at least one compound selected from the group consisting of compounds represented by the General Formulas (1) to (6)

-continued

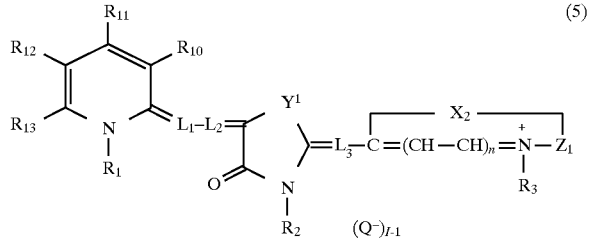

(5)

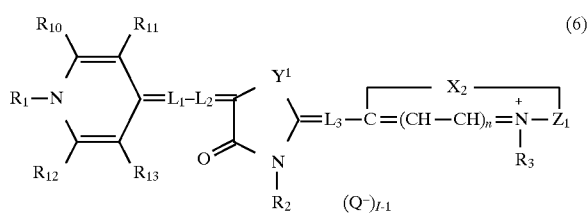

(6)

wherein
$X_1$ is O, S, Se, or >N—$R_{14}$,

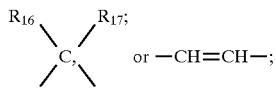  or —CH=CH—;

$X_2$ is O, S, Se, >N—$R_{15}$, $X_3$ is O, S, Se,

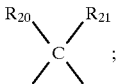  ;

$X_4$ is >N—$R_{19}$, or
$Y_1$ is O, S, Se, or >N—$R_{18}$;
$Z_1$ represents an atomic group necessary to form a saturated or unsaturated 5- or 6-membered ring which may be substituted or may have another ring fused therewith;
$Z_2$ is a naphthalene ring, an anthracene ring or a phenanthrene ring which may be substituted; in combination with (B) a pharmaceutically acceptable carrier or diluent; and a method for treatment of cancer comprising administering the above pharmaceutical composition to a host afflicted with cancer.

50 Claims, 7 Drawing Sheets

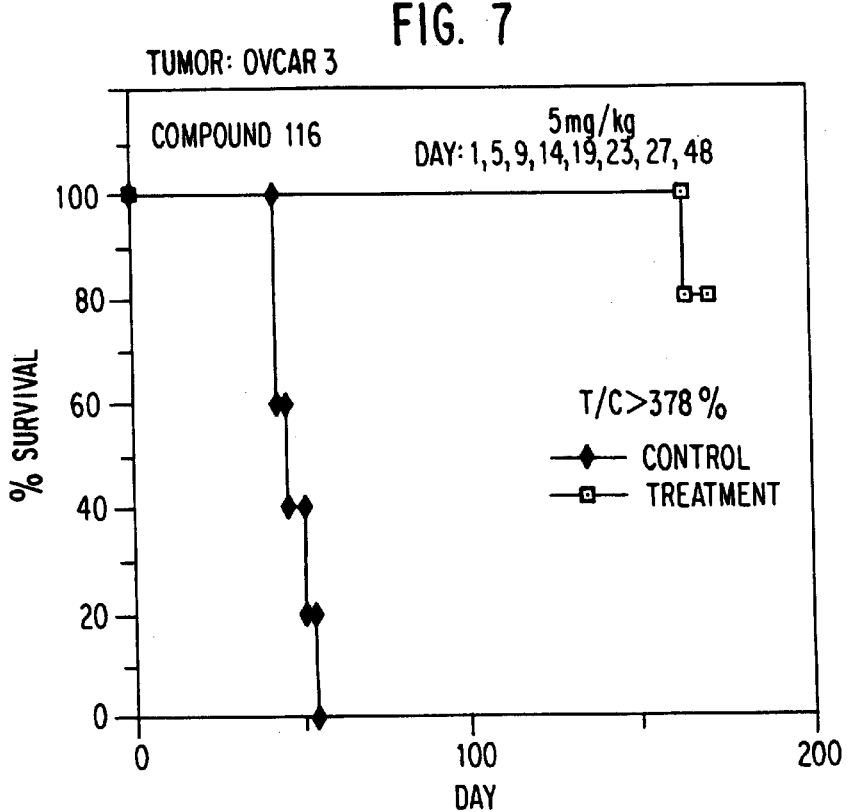
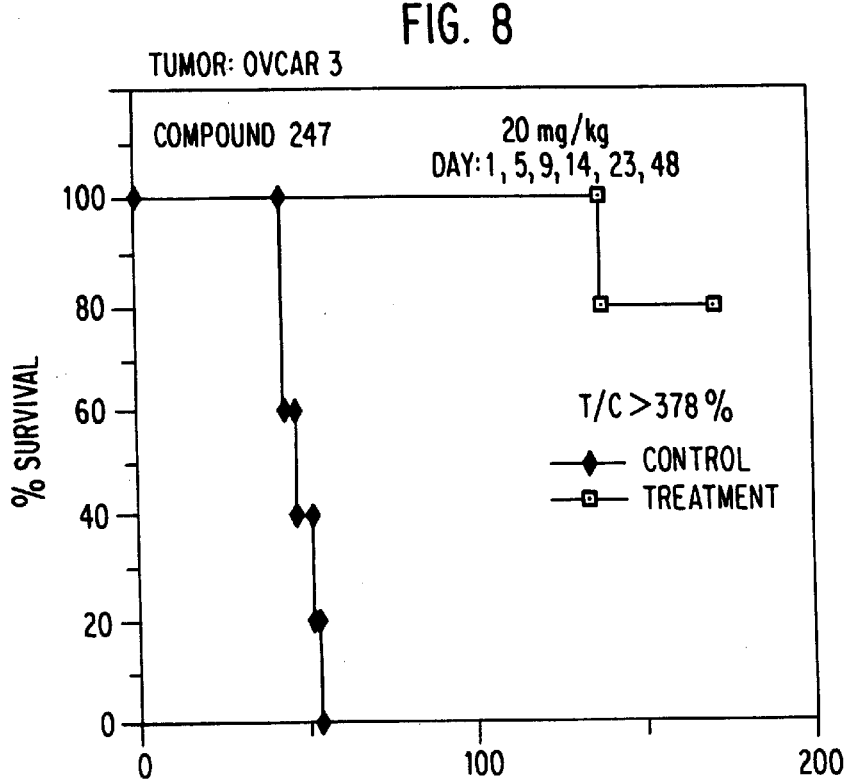

COMPOSITION AND METHOD FOR TREATING CANCER

This is a Continuation of application Ser. No. 07/974,480 filed on Nov. 12, 1992 (abandoned), which is a Continuation-in-Part of application Ser. No. 07/692,347 filed Apr. 26, 1991 (abandoned).

FIELD OF THE INVENTION

This invention relates to a composition and a method useful in treating a number of different types of cancers, and, in particular, carcinomas or melanomas. More particularly, this invention relates to a pharmaceutical composition containing a select class of rhodacyanine dyes useful in treating cancers and to a method for treating cancers using this composition.

BACKGROUND OF THE INVENTION

Cancer is a serious health problem throughout the world. As a result, an extensive amount of research has been conducted to develop therapies appropriate to the treatment and alleviation of cancer in humans.

In the chemotherapeutic area, research has been conducted to develop anti-tumor agents effective against various types of cancer. Often anti-tumor agents developed and found effective against cancerous cells, unfortunately, are toxic to normal cells. This toxicity gives rise to hair loss, nausea, weight loss, vomiting, hallucination, fatigue, itching, loss of appetite, etc., when administered to a patient needing cancer therapy.

Further, conventionally used chemotherapeutic agents do not have the effectiveness desired or are not as broadly effective against different types of cancers as is desired. As a result, chemotherapeutic agents which have greater effectiveness against cancers and which have a higher degree of selectivity for killing cancer cells with no or minimal effect on normal healthy cells is desired. Highly effective and selective anti-tumor agents, in particular, against cancers of the colon, bladder, prostate, stomach, pancreas, breast, lung, liver, brain, testis, ovary, cervix, skin, vulva, small intestine and like organs is desired. Anti-tumor agents against cancers such as colon cancer and melanomas are also particularly desired because of the lack of any particularly effective therapy at present.

Certain types of cyanine dyes have been disclosed as having anti-cancer activity (see, for example, Japanese Kokai 79/151,133, 80/31,024, 80/69,513, 80/100,318, Japanese Koho 89/54,325, E.P. No. 286252A2). However, these cyanine dyes cannot be used effectively for therapy in humans because of their high toxicity to healthy cells as well as to cancer cells. In addition, these cyanine dyes often are poorly soluble in diluents acceptable for human administration.

SUMMARY OF THE INVENTION

Accordingly, an object of this invention is to provide anti-tumor agents effective against cancer cells.

A further object of the present invention is to provide anti-tumor agents useful in the treatment of cancer where a higher degree of selectivity against cancer cells exists than has been found for prior art anti-tumor agents.

An even further object of the present invention is to provide anti-tumor agents effective in treatment against carcinomas and melanomas for which prior art treatments have not been found to be particularly effective.

A still further object of this invention is to provide pharmaceutical compositions and a method using the pharmaceutical compositions useful in the treatment and alleviation of cancer in mammals such as humans.

Still another object of the present invention is to provide rhodacyanine dyes which are highly soluble in aqueous diluents suitable for human administration using a pharmaceutically acceptable salt thereof, e.g., using acetate or chloride as a counter ion.

As a result of extensive research, it has now been found that the above-objects of the present invention are satisfied by classes of rhodacyanine dyes, heretofore known primarily for their use in the fabrication of photosensitive materials, which are effective in treating cancer and, in particular carcinomas and melanomas.

In one embodiment, the present invention provides a composition containing (A) a therapeutically effective amount of a rhodacyanine compound selected from the group consisting of compounds of the General Formulas (1), (2), (3), (4), (5) and (6)

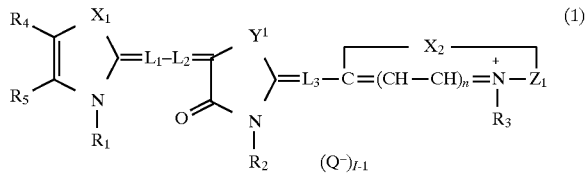

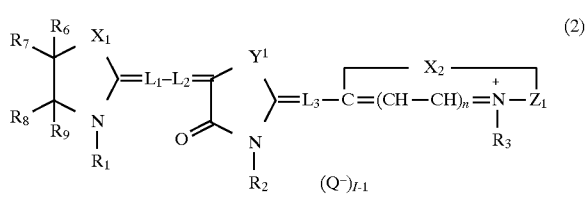

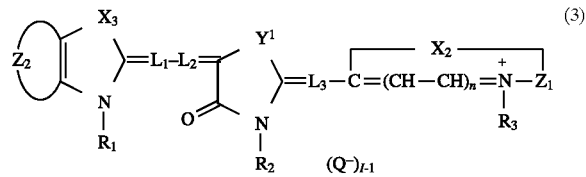

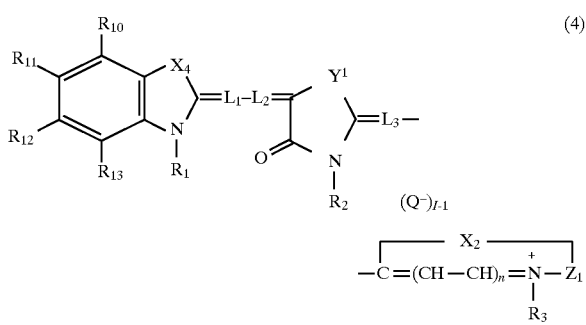

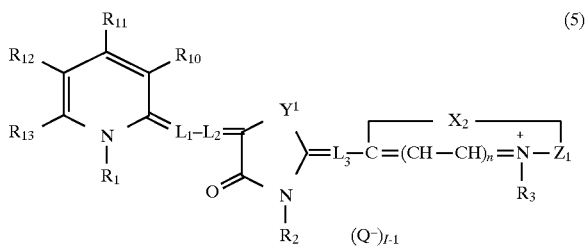

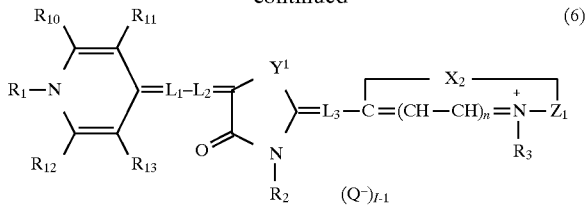

(6)

wherein $X_1$ is O, S, Se, or $>N\text{---}R_{14}$,

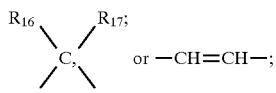

or —CH=CH—;

$X_2$ is O, S, Se, N—$R_{15}$,
$X_3$ is O, S, or Se,

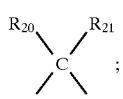

$X_4$ is $>N\text{---}R_{19}$, or $Y_1$ is O, S, Se, or $>N\text{---}R_{18}$;

$Z_1$ represent an atomic group necessary to form a saturated or unsaturated 5- or 6-membered ring which may be substituted or may have another ring fused therewith;

$Z_2$ represents an atomic group necessary to form a naphthalene ring, an anthracene ring or a phenanthrene ring which may be substituted;

$R_1$, $R_3$, $R_{14}$, $R_{15}$, and $R_{19}$, which may be the same or different, each represents an unsubstituted or substituted alkyl group;

$R_2$ and $R_{18}$, which may be the same or different, each represents an unsubstituted or substituted alkyl group, an unsubstituted or substituted aryl group or an unsubstituted or substituted heterocyclic group, $L_1$, $L_2$, and $L_3$, which may be the same or different, each represents a methine group or a substituted methine group, and in the case of a substituted methine group $L_1$ and $R_1$ and/or $L_3$ and $R_3$ may combine and form a saturated or unsaturated 5- or 6-membered ring;

$R_4$ and R5, which may be the same or different, each represents a hydrogen atom, an unsubstituted or substituted alkyl group or an unsubstituted or substituted aryl group;

$R_6$, $R_7$, $R_8$, and $R_9$, which may be the same or different, each represents a hydrogen atom, an unsubstituted or substituted alkyl group or an unsubstituted or substituted aryl group or any two of $R_6$ to $R_9$ may combine and form a saturated or unsaturated 5- or 6-membered ring;

$R_{10}$, $R_{11}$, $R_{12}$ and $R_{13}$, which may be the same or different, each represents a hydrogen atom, an unsubstituted or substituted alkyl group, an unsubstituted or substituted aryl group, an unsubstituted or substituted alkoxy group, an unsubstituted or substituted aryloxy group, an unsubstituted or substituted acyl group, an unsubstituted or substituted alkoxycarbonyl group, a trifluoromethyl group, an unsubstituted or substituted benzoyl group, an unsubstituted or substituted ureido group, an unsubstituted or substituted amino group, an unsubstituted or substituted amido group, an unsubstituted or substituted sulfamido group, an unsubstituted or substituted carbamyl group, an unsubstituted or substituted sulfamoyl group, a halogen atom, a nitro group, a cyano group, a hydroxy group or a carboxyl group, or any adjacent two of $R_{10}$ to $R_{13}$ may combine and form a saturated or unsaturated 5- or 6-membered ring, which may be substituted and which may have other rings fused therewith;

$R_{16}$, $R_{17}$, $R_{20}$ and $R_{21}$, which may be the same or different, each represents an unsubstituted or substituted alkyl group;

$Q^\ominus$ represents a pharmaceutically acceptable anion;

n represents 0 or 1; and l represents 1 or 2.

BRIEF DESCRIPTION OF THE ACCOMPANYING DRAWINGS

FIGS. 1 to 13 are graphical presentations of the results obtained in the Examples described hereinafter.

DETAILED DESCRIPTION OF THE INVENTION

Figure 1:
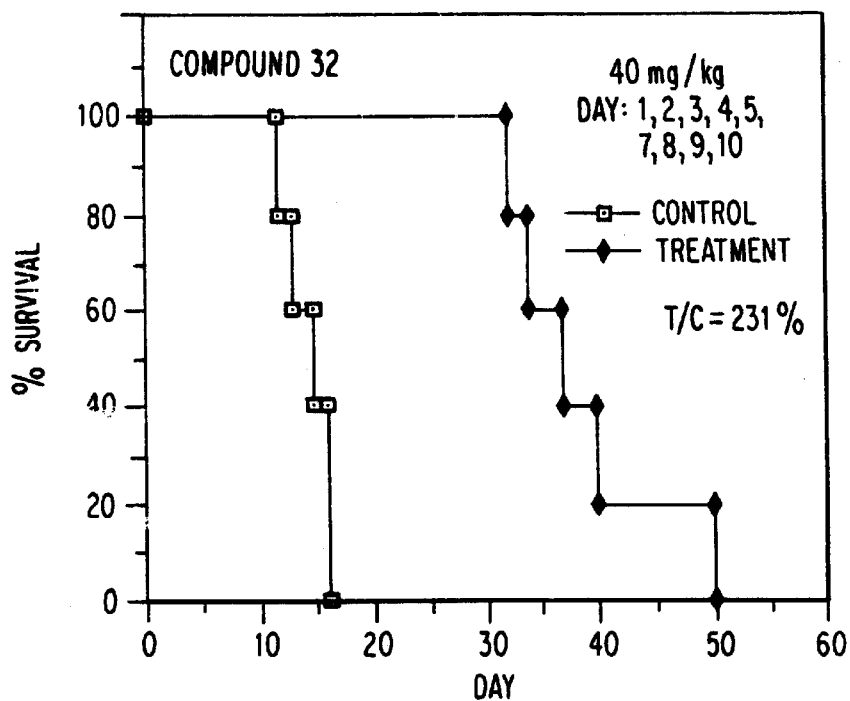
Figure 2:
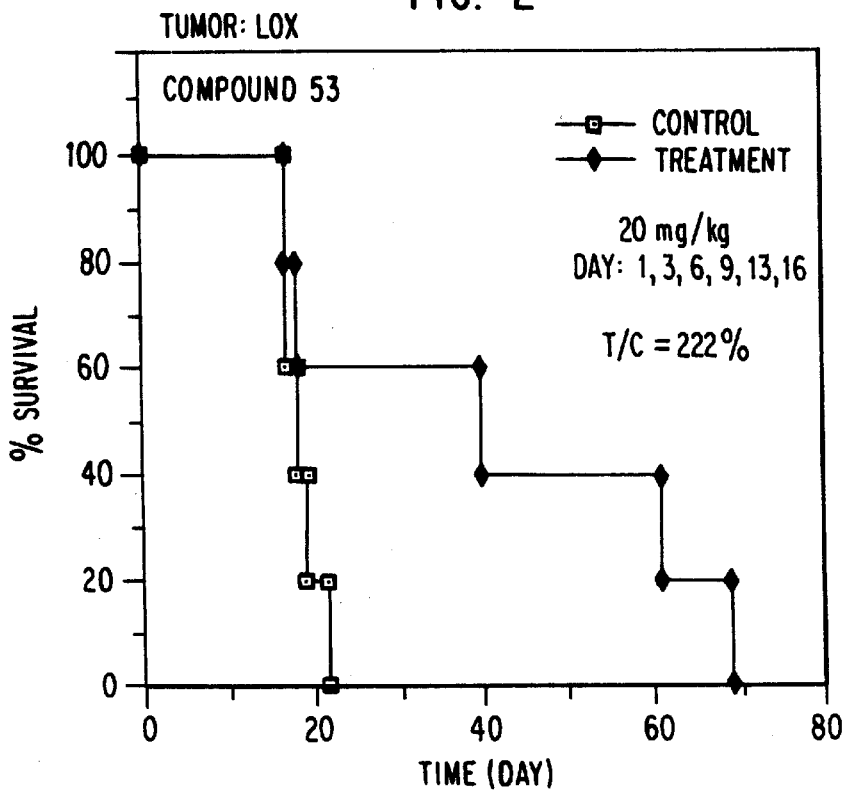
Figure 3:
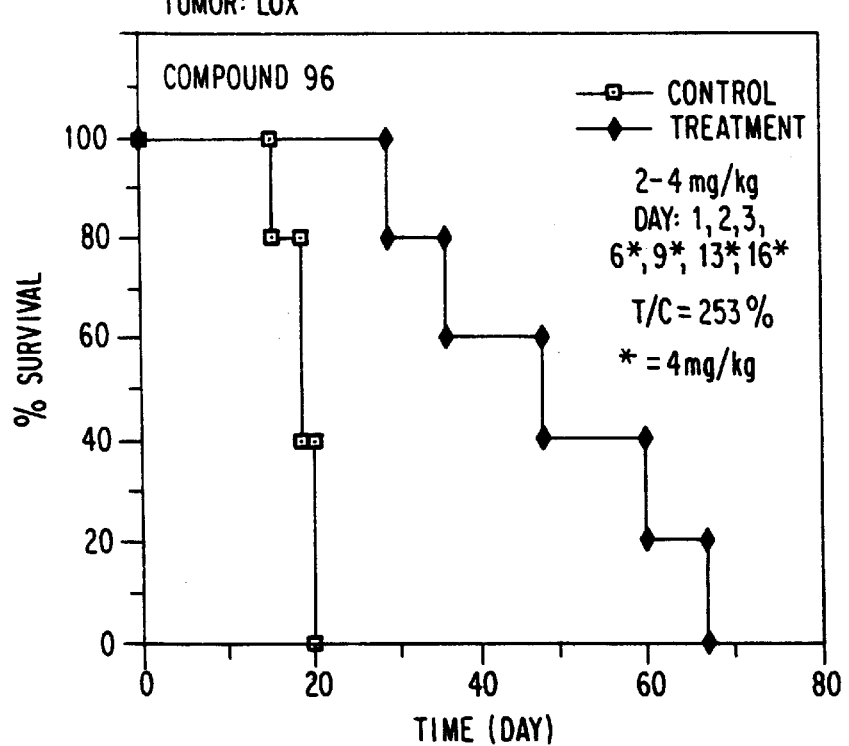
Figure 4:
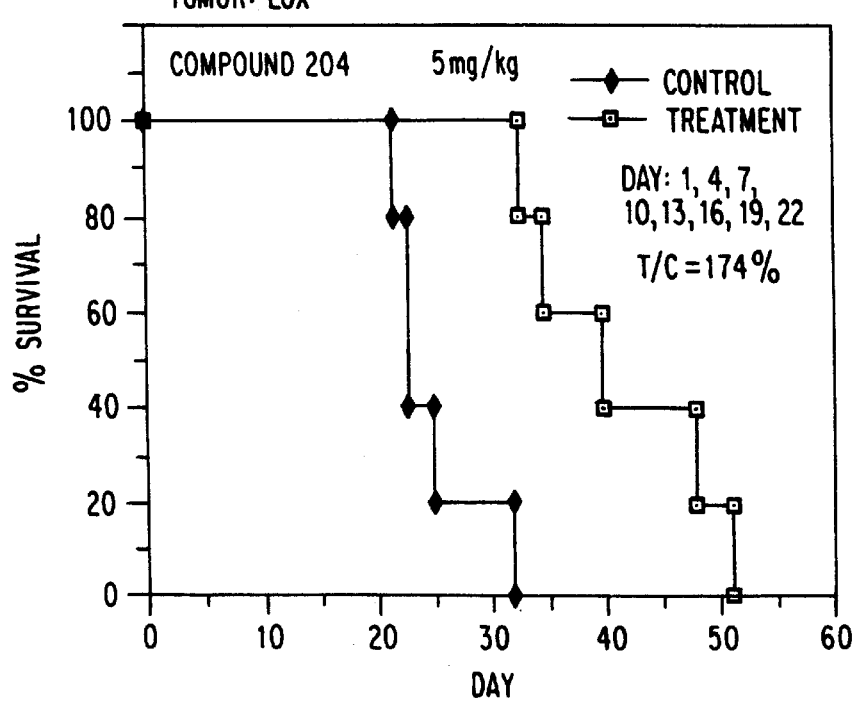
Figure 5:
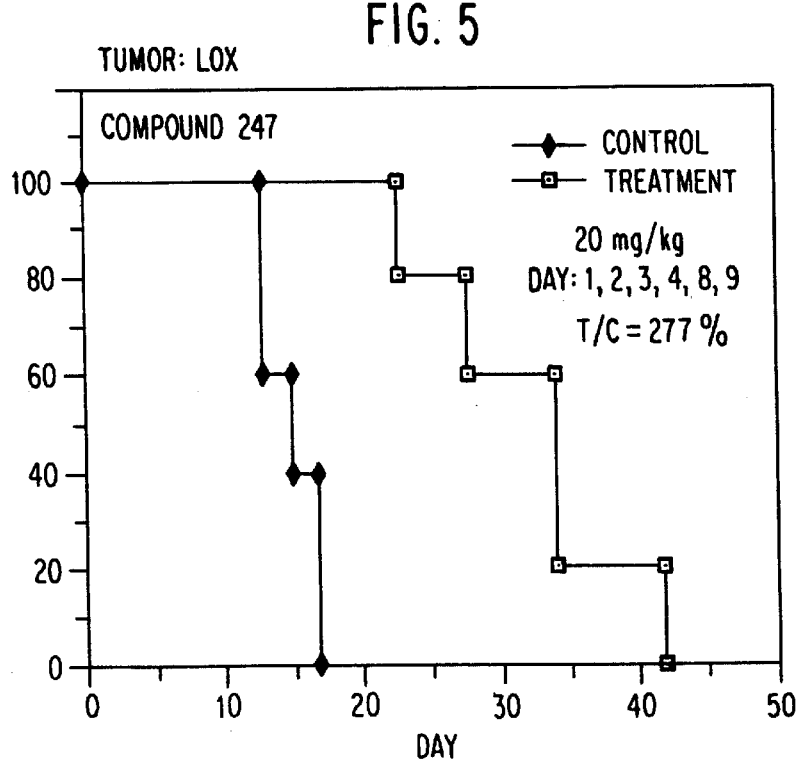
Figure 6:
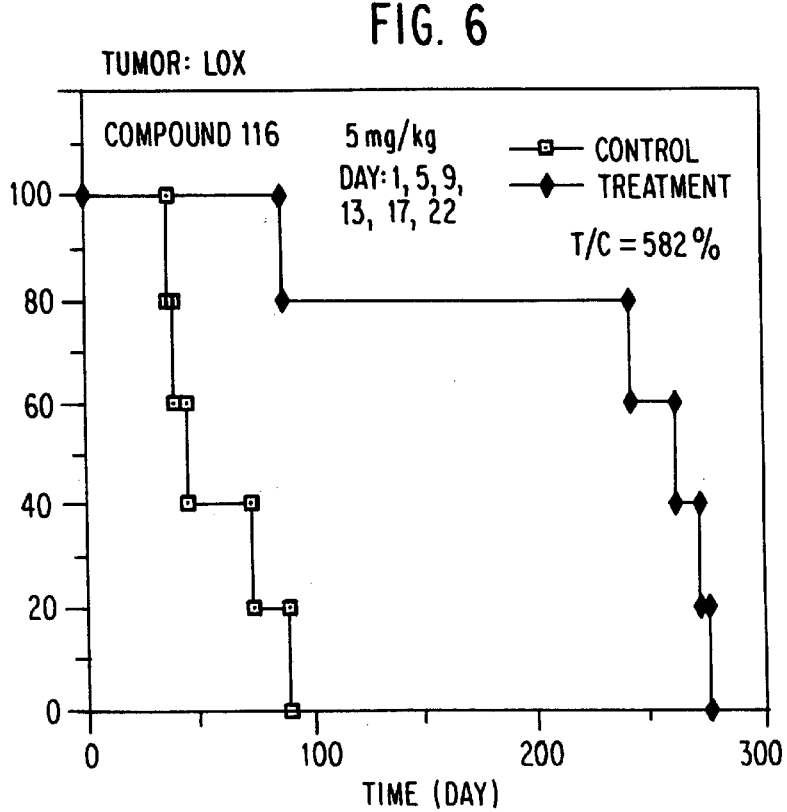

The embodiments of this invention involve cyanine compounds selected from the group consisting of compounds represented by the General Formulas (1) to (6) above as an anti-cancer agent, along with a suitable pharmaceutically acceptable carrier or diluent.

In greater detail, in the General Formulas (1) to (6)

$X_1$, $X_2$ and $X_3$ each, individually, represents an oxygen atom, a sulfur atom or a selenium atom. Moreover, $X_1$ represents a group of the formula $>N\text{---}R_{14}$, $X_2$ represents a group of the formula $>N\text{---}R_{15}$,

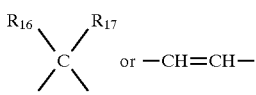

and $X_4$ represents a group of the formula $>N\text{---}R_{19}$ or

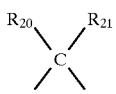

where $R_{14}$, $R_{15}$, $R_{16}$, $R_{17}$, $R_{19}$, $R_{20}$ and $R_{21}$ each represents an unsubstituted or substituted alkyl group such as a straight-chain, branched chain or cyclic alkyl group, $Y_1$ represents an oxygen atom, a sulfur atom, a selenium atom or a group of the formula

where $R_{18}$ is an unsubstituted or substituted alkyl group such as a straight-chain, branched chain or cyclic alkyl group, an unsubstituted or substituted aryl group such as a monocyclic or bicyclic aryl group, or an unsubstituted or substituted heterocyclic group such as a 5- to 6-membered heterocyclic group which can be saturated or unsaturated and can contain one or more nitrogen atoms, oxygen atoms and sulfur atoms.

$R_1$, $R_2$ and $R_3$ each individually represents an unsubstituted or substituted alkyl group such as a straight-chain, branched chain or cyclic alkyl group and $R_2$ can additionally be an unsubstituted or substituted aryl group such as a monocyclic, bicyclic or tricyclic aryl group or an unsubstituted or substituted heterocyclic group such as a 5- to 6-membered heterocyclic group which can be saturated or unsaturated and can contain one or more nitrogen atoms, oxygen atoms and sulfur atoms as hetero atoms.

$Z_1$ represents an atomic group necessary to form a saturated or unsaturated 5- or 6-membered ring which may contain one or more nitrogen atoms, oxygen atoms, sulfur atoms or selenium atoms as hetero atoms and $Z_1$ may be substituted or condensed with another ring such as a saturated or unsaturated ring.

$Z_2$ represents an atomic group necessary to form a naphthalene ring, an anthracene ring or a phenanthrene ring, which rings may be substituted.

$L_1$, $L_2$ and $L_3$ individually represent a methine group or a substituted methine group and when any of $L_1$, $L_2$ and $L_3$ is a substituted methine group, $L_1$ and $R_1$ and/or $L_3$ and $R_3$ may combine to form a saturated or unsaturated 5- or 6-membered ring.

$R_4$ and $R_5$ each represents a hydrogen atom or an unsubstituted or substituted alkyl group such as a straight-chain, branched chain or cyclic alkyl group and moreover, $R_4$ and $R_5$ represents an unsubstituted or substituted aryl group such as a monocyclic, bicyclic or tricyclic aryl group.

$R_6$, $R_7$, $R_8$ and $R_9$ each represents a hydrogen atom or an unsubstituted or substituted alkyl group such as a straight-chain, branched chain or cyclic alkyl group and moreover, $R_6$, $R_7$, $R_8$ and $R_9$ represents an unsubstituted or substituted aryl group such as a monocyclic, bicyclic or tricyclic aryl group.

Further, any two of $R_6$ and $R_9$ may combine and form an unsubstituted or substituted 5- or 6-membered carbocyclic ring.

$R_{10}$, $R_{11}$, $R_{12}$ and $R_{13}$ each represents a hydrogen atom or an unsubstituted or substituted alkyl group such as a straight-chain, branched chain or cyclic alkyl group and moreover, $R_{10}$, $R_{11}$, $R_{12}$ and $R_{13}$ each represents an unsubstituted or substituted aryl group such as a monocyclic or bicyclic aryl group.

Further, $R_{10}$, $R_{11}$, $R_{12}$ and $R_{13}$ each represents an unsubstituted or substituted alkoxy group, for example, an alkoxyl group where the alkyl moiety thereof is a straight-chain or branched chain alkyl moiety; an unsubstituted or substituted aryloxy group, for example, an aryloxy group where the aryl moiety thereof is monocyclic or bicyclic; an unsubstituted or substituted acyl group, for example, an alkylacyl group where the alkyl moiety thereof is a straightchain or branched chain alkyl moiety or an arylacyl group where the aryl moiety thereof is monocyclic or bicyclic; an unsubstituted or substituted alkoxycarbonyl group, for example, an alkoxycarbonyl group where the alkyl moiety thereof is a straight-chain or branched chain alkyl moiety; a trifluoro methyl group; an unsubstituted or substituted benzoyl group; an unsubstituted or substituted ureido group, for example, an alkylureido group where the alkyl moiety thereof is a straight-chain or branched chain alkyl moiety or an arylureido group where the aryl moiety thereof is monocyclic or bicyclic; an unsubstituted or substituted amino group, for example, a mono- or di-alkylamino group where the alkyl moiety thereof is a straight-chain or branched chain alkyl moiety or a mono- or di-arylamino group where the aryl moiety thereof is a monocyclic or bicyclic; an unsubstituted or substituted amido group, for example, a mono- or di-alkylamido group where the alkyl moiety thereof is a straight-chain or branched chain alkyl moiety or a mono- or di- arylamido group where the aryl moiety thereof is monocyclic or bicyclic; an unsubstituted or substituted sulfamido group, for example, an alkylsulfamido group where the alkyl moiety thereof is a straight chain or branched chain alkyl moiety or an arylsulfonamido group where the aryl moiety thereof is monocyclic or bicyclic an unsubstituted or substituted carbamyl group, for example, an alkylcarbamyl group where the alkyl moiety thereof is a straight chain or branched chain alkyl moiety or an arylcarbamyl group where the aryl moiety thereof is monocyclic or bicyclic; an unsubstituted or substituted sulfamoyl group, for example, an alkylsulfamoyl group where the alkyl moiety thereof is a straight chain or branched chain alkyl moiety or an arylsulfamoyl group where the aryl moiety thereof is monocyclic or bicyclic; a halogen atom such as a bromine atom, a chlorine atom, an iodine atom or a fluorine atom; a nitro group; a cyano group; a hydroxy group; or a carboxy group, or any adjacent two of $R_{10}$ to $R_{13}$ may combine and form a saturated or unsaturated 5- or 6-membered ring which may have other rings fused therewith.

$R_{16}$, $R_{17}$, $R_{20}$ and $R_{21}$ each represents an unsubstituted or substituted alkyl group, which may be a straight-chain, branched chain or cyclic alkyl group.

Q represents a pharmaceutically acceptable anion necessary for electrical charge balance, l is 1 or 2 and n is 0 or 1.

More specifically, as described above, $R_1$ and $R_3$ individually can represent an alkyl group which may be unsubstituted or substituted. Suitable examples of alkyl groups include straight-chain, branched chain and cyclic alkyl groups having 1 to 15 carbon atoms, more preferably 1 to 10 carbon atoms, even more preferably 1 to 8 carbon atoms. Specific examples of alkyl groups for $R_1$ and $R_3$ include methyl, ethyl, n-propyl, i-propyl, n-butyl, i-butyl, sec-butyl, tert-butyl, n-pentyl, hexyl, heptyl, octyl, cyclopropyl, cyclopentyl, cyclohexyl, 2-propenyl, 2-butenyl, 3-hexenyl and the like Specific examples of suitable substituents which can be present on the alkyl group when $R_1$ and $R_3$ represent a substituted alkyl group include halogen atoms such as chlorine, bromine, fluorine and iodine, an alkyl group, aryl group, an alkoxy group, a hydroxy group, and the like. A preferred number of carbon atoms for the unsubstituted and substituted alkyl groups for $R_1$ and $R_3$ ranges from 1 to 15, more preferably 1 to 10.

As defined above, $R_2$ and $R_{18}$ each represents an alkyl group which can be a straight-chain, branched chain or cyclic alkyl group and which may be substituted. Suitable examples of alkyl groups and substituents thereon are as described above for $R_1$ and $R_3$. A preferred number of carbon atoms for the alkyl group represented by $R_2$ and $R_{18}$ is from 1 to 15 carbon atoms, more preferably 1 to 10 carbon atoms.

The aryl group represented by $R_2$ and $R_{18}$ above can be a monocyclic, bicyclic or tricyclic aryl group such as a phenyl group, a biphenyl group, a naphthyl group or an anthracenyl group and such may be unsubstituted or substituted. Suitable examples of substituents which can be present on the aryl group represented by $R_2$ and $R_{18}$ include one or more of a halogen atom such as chlorine, bromine, fluorine or iodine, an alkyl group, an alkoxy group, a hydroxy group, a nitro group, a cyano group, an amino group, an alkyl- or aryl-substituted amino group, an acylamino group, a sulfonylamino group, a carbamoyl group, a sulfamoyl group, a carboxyl group, an alkoxycarbonyl group, and the like. A suitable number of carbon atoms for the aryl group for $R_2$ and $R_{18}$ is 6 to 20, preferably 6 to 15.

The heterocyclic ring represented by $R_2$ and $R_{18}$ can be a 5- to 6-membered heterocyclic ring containing one or more oxygen atoms, sulfur atoms or nitrogen atoms as hetero atoms. Suitable examples of heterocyclic rings represented by $R_2$ and $R_{18}$ include an imidazole ring, a thiazole ring, a pyrrole ring, a pyrazole ring, a furan ring, a thiophene ring, a piperidine ring, a morpholine ring, a piperadine ring, a pyrazine ring, a pyridine ring, a pyrimidine ring, and the like. These heterocyclic rings may be substituted, for example, by substitutents as described above for the aryl group for $R_2$ and $R_{18}$ or may be condensed with another ring such as a saturated or unsaturated ring.

Examples of alkyl groups represented by $R_{16}$, $R_{17}$, $R_{20}$ and $R_{21}$ include unsubstituted or substituted alkyl groups having from 1 to 15 carbon atoms, more preferably 1 to 10 carbon atoms. Suitable examples of suitable alkyl groups include those described above for $R_1$ and $R_3$ and substituents which can be present on the alkyl group represented by $R_{16}$, $R_{17}$, $R_{20}$ and $R_{21}$ include an alkyl group, an alkoxy group, a hydroxy group, a cyano group, a halogen atom, and the like.

Examples of alkyl groups represented by $R_{14}$, $R_{15}$, $R_{18}$ and $R_{19}$ above include alkyl groups as described above for $R_{16}$, $R_{17}$, $R_{20}$ and $R_{21}$. A suitable number of carbon atoms for the alkyl group for $R_{14}$, $R_{15}$, $R_{18}$ and $R_{19}$ is 1 to 15 carbon atoms, more preferably 1 to 10 carbon atoms. Further, $R_{14}$, $R_{15}$, $R_{16}$ and $R_{19}$ represents an unsubstituted or substituted aryl group which includes monocyclic, bicyclic and tricyclic aryl groups. A suitable number of carbon atoms for the aryl group for $R_{14}$, $R_{15}$, $R_{16}$ and $R_{19}$ is 6 to 20 carbon atoms, more preferably 6 to 15 carbon atoms. Specific examples of suitable aryl groups for $R_{14}$, $R_{15}$, $R_{18}$ and $R_{19}$ and substituents therefor include those described above for $R_2$.

The alkyl group represented by $R_4$, $R_5$, $R_6$, $R_7$, $R_8$, $R_9$, $R_{10}$, $R_{11}$, $R_{12}$ and $R_{13}$ above can be straight-chain, branched chain or cyclic and can include 1 to 15 carbon atoms, more preferably 1 to 10 carbon atoms, even more preferably 1 to 8 carbon atoms. The alkyl group represented by $R_4$, $R_5$, $R_6$, $R_7$, $R_8$, $R_9$, $R_{10}$, $R_{11}$, $R_{12}$ and $R_{13}$ can also be a substituted alkyl group. Specific examples of alkyl groups for $R_4$, $R_5$, $R_6$, $R_7$, $R_8$, $R_9$, $R_{10}$, $R_{11}$, $R_{12}$ and $R_{13}$ include methyl, ethyl, n-propyl, i-propyl, 2-propenyl, n-butyl, i-butyl, sec-butyl, tert-butyl, n-pentyl, hexyl, heptyl, octyl, cyclopropyl, cyclopentyl, cyclohexyl and the like. Specific examples of suitable substituents which can be present on the alkyl group when $R_4$, $R_5$, $R_6$, $R_7$, $R_8$, $R_9$, $R_{10}$, $R_{11}$, $R_{12}$ and $R_{13}$ represent a substituted alkyl group include halogen atoms such as chlorine, bromine, fluorine and iodine, an alkyl group, aryl group, an alkoxy group, a hydroxy group, and the like. A preferred number of carbon atoms for the unsubstituted and substituted alkyl groups for $R_4$, $R_5$, $R_6$, $R_7$, $R_8$, $R_9$, $R_{10}$, $R_{11}$, $R_{12}$ and $R_{13}$ ranges from 1 to 15, more preferably 1 to 10.

The aryl group represented by $R_4$, $R_5$, $R_6$, $R_7$, $R_8$, $R_9$, $R_{10}$, $R_{11}$, $R_{12}$ and $R_{13}$ can be a monocyclic, bicyclic or tricyclic aryl group such as a phenyl group, a biphenyl group, a naphthyl group or an anthracenyl group and such may be unsubstituted or substituted. Suitable examples of substituents which can be present on the aryl group represented by $R_4$–$R_{13}$ include one or more of a halogen atom such as chlorine, bromine, fluorine or iodine, an alkyl group, an alkoxy group, a hydroxy group, a nitro group, a cyano group, an amino group, an alkyl- or aryl-substituted amino group, an acylamino group, a sulfonylamino group, a carbamoyl group, a sulfamoyl group, a carboxyl group, an alkoxycarbonyl group, and the like. A suitable number of carbon atoms for the aryl group for $R_4$ to $R_{13}$ is 6 to 20, preferably 6 to 15.

Moreover, two of $R_6$, $R_7$, $R_8$ and $R_9$ may combine and form a 5- or 6-membered carbocyclic ring. A suitable number of carbon atoms for the carbocyclic ring including substituent groups thereon for $R_6$, $R_7$, $R_8$ and $R_9$ is 3 to 15 cabon atoms, preferably 3 to 10 carbon atoms.

Typical examples of 5- and 6-membered carbocyclic rings include a cyclopentane ring, a cyclopentene ring, a cyclohexane ring, a cyclohexene ring and the like.

$Z_1$ represents an atomic group necessary to form a saturated or unsaturated carbocyclic ring. Moreover, the ring formed by $Z_1$ can be substituted with one or more substituents or can be condensed with another ring such as a saturated or unsaturated ring, e.g., a cyclohexene ring, a benzene ring or a naphthalene ring. Suitable examples of substituents which can be present on the ring formed by $Z_1$ include one or more of an alkyl group, an alkoxy group, an aryloxy group, a halogen atom (such as chlorine, bromine, fluorine and iodine), an aryl group, a hydroxy group, an amino group, an alkyl- or aryl-substituted amino group, an acylamino group, a sulfonylamino group, a carbamoyl group, a sulfamoyl group, a carboxyl group, an alkoxycarbonyl group, an acyloxy group, a heterocyclic ring (such as a pyrrole ring, a furan ring, a piperidine ring, a morpholine ring, a pyridine ring, etc.) a cyano group, a nitro group, a trifluoromethyl group and the like, and suitable examples of saturated or unsaturated rings condensed therewith include a cyclopentene ring, a cyclohexene ring, a benzene ring, a naphthalene ring, an anthracene ring, a phenanthrene ring, a thiophene ring, a pyridine ring, etc.

Specific examples of heterocyclic rings formed by $Z_1$ include 5- and 6-membered heterocyclic rings such as those including nuclei comprising those of the thiazole series (e.g., thiazole, 4-methylthiazole, 4-phenylthiazole, 4,5-diphenylthiazole, 4,5-dimethylthiazole, etc.), those of the benzothiazole series (e.g., benzothiazole, 5-chlorobenzothiazole, 5-methylbenzothiazole, 5-phenylbenzothiazole, 5-methoxybenzothiazole, 4-fluorobenzothiazole, 5,6-dioxymethylenebenzothiazole, 5-nitrobenzothiazole, 5-trifluoromethylbenzothiazole, 5-methoxycarbonylbenzothiazole, 5-hydroxybenzothiazole, 5-cyanobenzothiazole, 5-iodobenzothiazole, etc.), those of the naphthothiazole series (e.g., α-naphthothiazole, β-naphthothiazole, γ-naphthothiazole, 5-methoxy-β-naphthothiazole, 8-methoxy-α-naphthothiazole, 6-methoxy-8-acetyloxy-β-naphthothiazole, 8,9-dihydro-β-naphthothiazole, etc.), those of the oxazole series (e.g., 4-methyloxazole, 4,5-diphenyloxazole, 4-phenoxyoxazole, etc.), those of the benzoxazole series (e.g., benzoxazole, 5-chlorobenzoxazole, 5,6-dimethylbenzoxazole,, 6-hydroxybenzoxazole, 5-phenylbenzoxazole, etc.), those of the naphthoxazole series (e.g., α-naphthoxazole, β-naphthoxazole, etc.), those of the selenazole series (e.g., 4-methylselenazole, 4-phenylselenazole, etc.), those of the benzoselenazole series (e.g., benzoselenazole, 5-chlorobenzoselenazole, 5-methoxybenzoselenazole, 5-hydroxybenzoselenazole, etc.), those of the thiazoline series (e.g., thiazoline, 4,4-dimethylthiazoline, etc.), those of the 2-pyridine series (e.g., 2-pyridine, 5-methyl-2-pyridine, 5-methoxy-2-pyridine, 4-chloro-2-pyridine, 5-carbamoyl-2-pyridine, 5-methoxycarbonyl-2-pyridine, 4-acetylamino-2-pyridine, etc.), those of the 4-pyridine series (e.g., 4-pyridine, 3-methoxy-4-pyridine, 3,5-dimethyl-4-pyridine, 3-chloro-4-pyridine, 3-methyl-4-pyridine, etc.), those of the 2-quinoline series (e.g., 2-quinoline, 6-methyl-2-quinoline, 6-chloro-2-quinoline, 6-ethoxy-2-quinoline, 6-hydroxy-2- quinoline, 6-nitro-2-quinoline, 6-acetylamino-2-quinoline, 6-dimethylaminocarbonyl-2-quinoline, 8-fluoro-2-quinoline, etc.), those of the 4-quinoline series (e.g., 4-quinoline, 6-methoxy-4-quinoline, 6-acetylamino-4-quinoline, 8-chloro-4-quinoline, 6-trifluoromethyl-4-quinoline, etc.), those of the 1-isoquinoline series (e.g., 1-isoquinoline, 6-methoxy-1-isoquinoline, 6-chloro-1-isoquinoline, etc.), those of the 3,3-dialkylindolenine series (e.g., 3,3-dimethylindolenine, 3,3,7-trimethylindolenine, 5-chloro-3,3,-dimethylindolenine, 5-ethoxycarbonyl-3,3-dimethylindolenine, 5-nitro-3,3-dimethylindolenine, 3,3-dimethyl-4,5-phenyleneindolenine, 3,3-dimethyl-6,7-phenyleneindolenine, 5-acetylamino-3,3-dimethylindolenine, 5-diethylamino-3,3-dimethylindolenine, 5-methanesulfonylamino-3,3-dimethylindolenine, 5-benzoylamino-3,3-dimethylindolenine, etc.), those of the imidazole series (e.g., imidazole, 1-alkyl-4-phenylimidazole, 1-alkyl-4,5-dimethylimidazole, etc. ), those of the benzimidazole series (e.g., benzimidazole, 1-alkylbenzimidazole, 1-alkyl-5-trifluorobenzimidazole, 1-alkyl-5-chlorobenzimidazole, 1-alkyl-5-sulfamoylbenzimidazole, 1-aryl-5-methoxycarbonylbenzimidazole, 1-alkyl-5-acetylaminobenzimidazole, 1-alkyl-5-nitrobenzimidazole, 1-alkyl-5-diethylaminobenzimidazole, 1-alkyl-5-pentyloxybenzimidazole, etc. ), those of naphthimidazole series (e.g., 1-alkyl-α-naphthimidazole, 1-alkyl-5-methoxy-β-naphthimidazole, etc.) and like rings.

$Z_2$ as described above represents an atomic group necessary for the formation of a naphthalene ring, an anthracene ring or a phenanthrene ring, i.e., one of these rings fused with the ring shown containing $X_3$. The ring formed by $Z_2$ can be substituted and suitable examples of substituents include one or more of an alkyl group, an alkoxy group, an aryloxy group, a halogen atom (such as chlorine, bromine, fluorine and iodine), a hydroxy group, an acyloxy group, and the like.

Typical examples of substituted rings formed by $Z_2$ include hydroxynapthalene, methoxynaphthalene, trimethoxynaphthalene, acetoxynaphthalene, methylnaphthalene, bromonaphthalene, hydroxyphenanthrene, methoxyphenanthrene and like rings.

Suitable examples of substituents which can be present on the $L_1$, $L_2$ and $L_3$ substituted methine group include an alkyl group (e.g., methyl, ethyl, butyl, etc.), an aryl group (e.g., phenyl, tolyl, etc.), a halogen atom (e.g., chlorine, bromine, fluorine and iodine), or an alkoxy group (e.g., methoxy, ethoxy, etc.) and suitable rings formed by the combination of $L_1$ and $R_1$ and/or $L_3$ and $R_3$ include a 5-membered heterocyclic ring (e.g., a pyrroline ring, etc.) and a 6-membered heterocyclic ring (e.g., a tetrahydropyridine ring, an oxazine ring, etc.).

The term "pharmaceutically acceptable anion" for Q which is necessary for electrical charge balance in the compounds above is intended to mean an ion, when administered to the host subjected to the method of treatment of this invention, which is non-toxic and which renders the compounds above soluble in aqueous systems.

Suitable examples of pharmaceutically acceptable anions represented by Q include halides such as chloride, bromide and iodide, sulfonates such as aliphatic and aromatic sulfonates, e.g., methanesulfonate, trifluoromethanesulfonate, p-toluenesulfonate, naphthalenesulfonate, 2-hydroxyethanesulfonate, and the like, sulfamates such as cyclohexanesulfamate, sulfates such as methyl sulfate and ethyl sulfate, bisulfates, borates, alkyl and dialkyl phosphates such as diethyl phosphate and methylhydrogen phosphate, pyrophosphates such as trimethylpyrophosphate and diethyl hydrogen pyrophosphate, carboxylates, advantageously carboxy- and hydroxy-substituted carboxylates and carbonates. Preferred examples of pharmaceutically acceptable anions include chloride, acetate, propionate, valerate, citrate, maleate, fumarate, lactate, succinate, tartrate and benzoate.

In particular, cyanine compounds of the General Formula (1) to (6) where $Y_1$ is a sulfur atom are preferred. Particularly preferred cyanine compounds are compounds of the General Formula (1) to (6) where $Y_1$ is a sulfur atom, $=L_1-L_2=$ is $=CH-CH=$ and $L_3$ is $=CH-$.

Particularly preferable cyanine compounds of the General formulae (1) to (6) are as follows:

In the compounds of the General Formula (1), those where $X_1$ is O or S; $Y_1$ is O or S; $X_2$ is O, S, Se or $-CH=CH-$; $R_1$, $R_2$ and $R_3$ each is an unsubstituted or substituted alkyl group having from 1 to 8 carbon atoms; and $L_1$ and $L_2$ each is a methine group are preferred and, among these, those where $X_1$ is S; $Y_1$ is S; the ring formed by $Z_1$ is a benzoxazole ring series, a benzothiazole ring series or an α-naphthothiazole ring series; $R_2$ is an alkyl group having from 1 to 3 carbon atoms; $R_4$ is a hydrogen atom; and $R_5$ is a methyl group are more preferred. Most preferred compounds in the General Formula (1) are those represented by the following formulae (7) and (8):

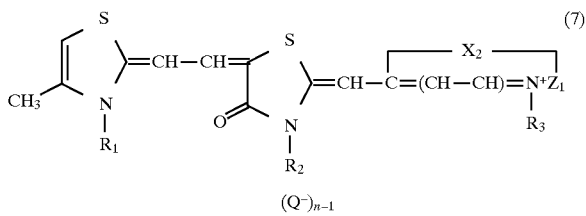

wherein

Q, n and 1 all have the same meanings as defined in the General formula (1);

$X_2$ is O or S;

$Z_1$ is an atomic group necessary to form a benzothiazole ring, an α-naphthothiazole ring, a 5,6-dimethylbenzothiazole ring and a 5,6-dimethoxybenzoxazole ring;

$R_1$ and $R_2$ each is a methyl group or an ethyl group; and $R_3$ is a methyl group, an ethyl group, a propyl group, a butyl group or a pentyl group.

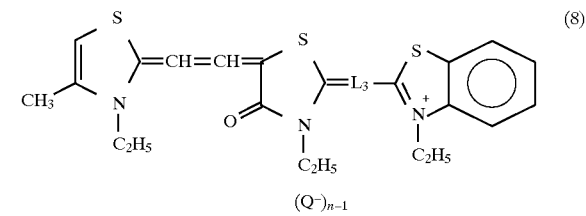

wherein $L_3$, Q and 1 have the same meanings as defined in the General formula (1); and $R_3$ is an ethyl group or a propyl group, and $L_3$ and $R_3$ may combine and form 5- and 6-membered ring.

In the compounds of the General Formula (2), those where $X_1$ is S; $Y_1$ is O or S; $X_2$ is O, S, Se, $CR_{16}R_{17}$ or $-CH=CH-$; $R_2$ is an unsubstituted or substituted alkyl group or an unsubstituted or substituted aryl group; $R_6$ and $R_7$ each is a hydrogen atom; $R_8$ and $R_9$ each is a hydrogen atom or an unsubstituted or substituted alkyl group; and $L_1$, $L_2$ and $L_3$ each is a methine group are preferred and, among these, those where $Y_1$ is S; $X_2$ is O, S, Se or —CH=CH—; the ring formed by $Z_1$ is a benzoxazole ring series, a naphthoxazole ring, a thiazoline ring series, a thiazole ring series, a benzothiazole ring series, a naphthothiazole ring series, a benzoselenazole ring series, an indolenine ring series, 2-quinoline ring series or a 4-quinoline ring series; $R_1$ is an alkyl group having from 1 to 2 carbon atoms ; $R_2$ is an alkyl group having from 1 to 3 carbon atoms or a phenyl group; $R_3$ is an alkyl group having from 1 to 6 carbon atoms; $R_6$ and $R_7$ each is a hydrogen atom; and $R_8$ and $R_9$ each is a hydrogen atom or methyl group are more preferred. Furthermore preferred compounds in the the General Formula (2) are those represented by the following formula (9):

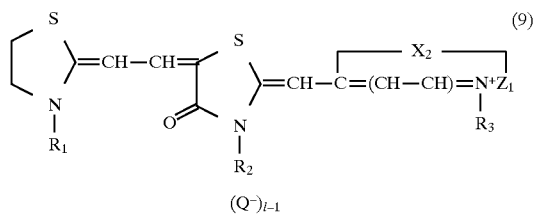

wherein

Q, n and l all have the same meanings as defined in the General formula (1);

$X_2$ is O, S, Se or —CH=CH—;

$Z_1$ is an atomic group necessary to form a benzoxazole ring series, a naphthoxazole ring, a thiazoline ring series, a benzothiazole ring series, a naphthothiazole ring series, a benzoselenazole ring series or a 4-quinoline ring series;

$R_1$ is a methyl group or an ethyl group;

$R_2$ is a methyl group, an ethyl group, $CH_3OCH_2CH_2$ or a phenyl group; and $R_3$ is a methyl group, an ethyl group, a propyl group, a butyl group, n-$C_5H_{11}$, $HOCH_2CH_2$, $HOCOCH_2CH_2$, $CH_3OCH_2CH_2$, $NH_2COCH_2CH_2$, $HOCH_2(HO)CH_2$, $CH_3SO_2NHCOCH_2$ or

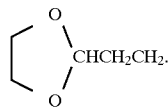

Most preferable compounds in the General Formula (2) are those where the ring formed by $Z_1$ is an α-naphthoxazole ring, a thiazoline ring, a benzothiazole ring, a 5-chlorobenzothiazole ring, a 5-methylbenzothiazole ring, a 5-methoxybenzothiazole ring, a 5,6-dimethoxy benzothiazole ring, a 4-methoxy benzothiazole ring, a 5,6-dichlorobenzothiazole ring, an α-naphthothiazole ring, a benzoselenazole ring, a 4-quinoline ring; $R_2$ is a methyl group or an ethyl group; and $R_3$ is a methyl group, an ethyl group or $CH_3OCH_2CH_2$ in the General Formula (9).

In the compounds of the General Formula (3), those where $X_2$ is O, S, Se or —C=C—; $X_3$ is O or S; $Y_1$ is S; the ring formed by $Z_2$ is a naphthalene-ring; $R_2$ is an unsubstituted or substituted alkyl group or an unsubstituted or substituted aryl group; and $L_1$ and $L_2$ each is a methine group are preferred and, among these, those where the ring formed by $Z_1$ is a benzoxazole ring series, a naphthoxazole ring series, a thiazole ring series, a benzothiazole ring series, a naphthothiazole ring series, a benzoselenazole ring series, a 2-pyridine ring or 2-quinoline ring series; the naphthalene ring formed by $Z_2$ fuses with the ring formed by $X_3$ to form an α-naphthothiazole ring, a β-naphthothiazole ring, an α-naphthoxazole ring, a β-naphthoxazole ring or a γ-naphthoxazole ring; $R_1$ and $R_3$ each is an alkyl group having from 1 to 8 carbon atoms; $R_2$ is an alkyl group having from 1 to 8 carbon atoms or an aryl group having from 6 to 8 carbon atoms; and $L_3$ is a methine group are more preferred. Furthermore preferred compound in these are those where $X_2$ is O or S; the ring formed by $Z_1$ is a naphthoxazole ring series or a naphthothiazole ring series (especially those where $X_2$ and $X_3$ each is S; the ring formed by $Z_1$ is a naphthothiazole ring series; $R_1$ is a methyl group or a ethyl group; $R_2$ is a methyl group, an ethyl group, a vinyl methyl group, a n-propyl group, $CH_3COOCH_2CH_2$ or a phenyl group; and $R_3$ is a methyl group, an ethyl group, a n-propyl group or a hydoxyethyl group), those where $X_2$ and $X_3$ each is S; the ring formed by $Z_1$ is an α-naphthothiazole ring, β-naphthothiazole ring or a benzothiazole ring; the naphthalene ring formed by $Z_2$ fuses with the ring formed by $X_3$ to form an α-naphthothiazole ring or a β-naphthothiazole ring; $R_1$ is a methyl group or an ethyl group; $R_2$ is a methyl group, an ethyl group, a vinyl methyl group, a n-propyl group, $CH_3COOCH_2CH_2$ or a phenyl group; and $R_3$ is a methyl group, an ethyl group, a n-propyl group or a hydoxyethyl group, those where $X_2$ is O; $X_3$ is O or S; the ring formed by $Z_1$ is an α-naphthoxazole ring, a β-naphthoxazole ring; the naphthalene ring formed by $Z_2$ fuses with the ring formed by $X_3$ to form an α-naphthothiazole ring, a β-naphthothiazole ring or a β-naphthoxazole ring; $R_1$ is a methyl group or an ethyl group; $R_2$ is a methyl group, an ethyl group, a vinyl methyl group, a n-propyl group, $CH_3COOCH_2CH_2$ or a phenyl group; and $R_3$ is a methyl group, an ethyl group, a n-propyl group or a hydoxyethyl group, and those where $X_2$ is —CH=CH—; $X_3$ is S; the ring formed by $Z_1$ is a 4-quinoline ring; the naphthalene ring formed by $Z_2$ fuses with the ring formed by $X_3$ to form an α-naphthothiazole ring or a β-naphthothiazole ring; $R_1$ is a methyl group or an ethyl group; $R_2$ is a methyl group, an ethyl group, a vinyl methyl group, a n-propyl group, $CH_3COOCH_2CH_2$ or a phenyl group; and $R_3$ is a methyl group, an ethyl group, a n-propyl group or a hydoxyethyl group.

In the compounds of the General Formula (4), those where $X_2$ is O, S or —CH=CH—; $X_4$ is

$Y_1$ is S; the ring formed by $Z_1$ is a benzoxazole ring series, a thiazole ring series, a benzothiazole ring series, a naphthothiazole ring series, 2-quinoline ring series or 4-quinoline ring series; $R_2$ is an unsubstituted or substituted alkyl group or an unsubstituted or substituted aryl group; $R_{11}$ and $R_{12}$ each is a hydrogen atom, a halogen atom or an unsubstituted or substituted alkyl group; $R_{10}$ and $R_{13}$ each is a hydrogen atom; and $L_1$, $L_2$ and $L_3$ each is a methine group and those where $X_2$ is O, S, —CH=CH—; $X_4$ is

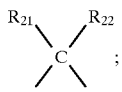

$Y_1$ is S; the ring formed by $Z_1$ is a benzoxazole ring series, a naphthoxazole ring, a thiazoline ring series, a thiazole ring series, a benzothiazole ring series, a naphthothiazole ring series, a benzoselenazole ring series, an indolenine ring, 2-quinoline ring series or a 4-quinoline ring series; $R_2$ is an unsubstituted or substituted alkyl group; $R_{10}$, $R_{12}$ and $R_{13}$ each is a hydrogen atom; $R_{11}$ is a hydrogen atom, a halogen atom, a nitro group, an unsubstituted or substituted alkylcarbonyl group, an unsubstituted or substituted acylamino group, an unsubstituted or substituted aminoalkyl group or an unsubstituted or substituted alkylsulfamido group; and $L_1$, $L_2$ and $L_3$ each is a methine group are preferred.

More preferred compounds in the General Formula (4) are those represented by the following formulae (10) and (11)

chlorine atom or a trifluoromethyl group are preferred and, in the compounds of the General Formula (11), those where the ring formed by $Z_1$ is a 4,5-diphenylthiazole ring, a benzothiazole ring, a 6-methylbenzothiazole ring, a 5-chlorobenzothiazole ring, a 5-ethoxy-6-methylbenzothiazole ring, a α-naphthothiazole ring, a α-naphthoxazole ring or a 4-quinoline ring; $R_1$, $R_2$ and $R_3$ each is a methyl group or an ethyl group; and $R_1$, is a hydrogen atom or a chlorine atom are preferred.

In the compounds of the General Formula (5), those represented by the following General Formula (12) are preferred.

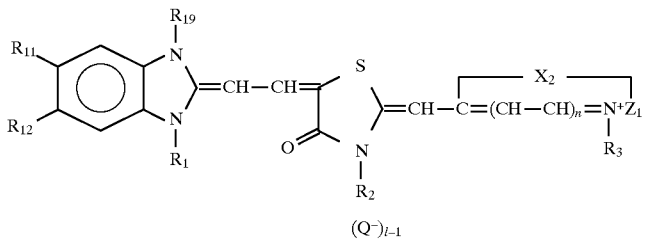

(10)

wherein
- Q, n and 1 all have the same meanings as defined in the General formula (1);
- $X_2$ is S;
- $Z_1$ is an atomic group necessary to form a naphthothiazole ring series;
- $R_1$, $R_2$, $R_3$ and $R_{19}$ each is an unsubstituted or substituted alkyl group having from 1 to 8 carbon atoms;
- $R_{11}$ is a hydrogen atom; and
- $R_{12}$ is a hydrogen atom, a halogen atom or a halogenated alkyl group.

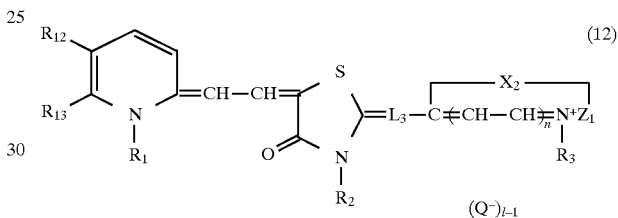

(12)

wherein
- $L_3$, Q, n and 1 all have the same meanings as defined in the General formula (1);

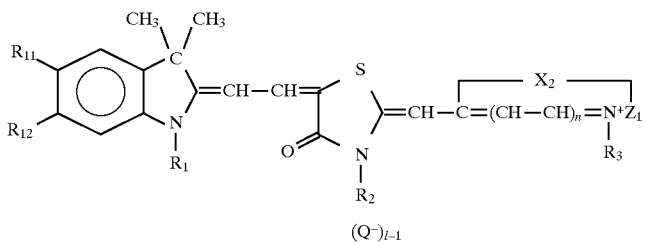

(11)

wherein
- Q, n and 1 all have the same meanings as defined in the General formula (1);
- $X_2$ is O, S or —CH=CH—;
- $Z_1$ is an atomic group necessary to form a thiazole ring series, a benzothiazole ring series, a naphthothiazole ring series, a naphthoxazole ring, a 2-quinoline ring series or a 4-quinoline ring series;
- $R_1$, $R_2$ and $R_3$ each is an unsubstituted or substituted alkyl group having from 1 to 8 carbon atoms;
- $R_{11}$ is a hydrogen atom or a halogen atom; and
- $R_{12}$ is a hydrogen atom.

Further, in the compounds of the General Formula (10), those where the ring formed by $Z_1$ is a α-naphthoxazole ring or a β-naphthoxazole ring; $R_1$ is a methyl group, an ethyl group or $CHF_2CF_2CH_2$; $R_2$, $R_3$ and $R_{19}$ each is a methyl group or an ethyl group; and $R_{12}$ is a hydrogen atom, $X_2$ is S or —CH=CH—;
$Z_1$ is an atomic group necessary to form a thiazoline ring series, a benzothiazole ring series, a naphthothiazole ring series or a 4-quinoline ring series;
$R_1$, $R_2$ and $R_3$ each is an unsubstituted or substituted alkyl group having from 1 to 8 carbon atoms; and
$R_{12}$ and $R_{13}$ each is a hydrogen atom or an unsubstituted or substituted alkyl group or $R_{12}$ and $R_{13}$ may combine and forma saturated or unsaturated 6-membered ring.

Further, among the compounds of the General Formula (12), more preferred are those where $X_2$ is S; the ring formed by $Z_1$ is a benzothiazole ring series or a naphthothiazole ring series; $R_{12}$ is a hydrogen atom, a methyl group or an ethyl group; $R_{13}$ is a hydrogen atom; and $L_3$ is a methine group and, most preferred are those where the ring formed by $Z_1$ is a 5,6-dimethylbenzothiazole ring or a β-naphthothiazole ring; $R_{12}$ is a hydrogen atom or a methyl group; $R_1$ and $R_3$ each is a methyl group or an ethyl group; $R_2$ is a methyl group, an ethyl group or a vinyl methyl group.

In the compounds of the General Formula (5), those represented by the General Formula (13) are also preferred.

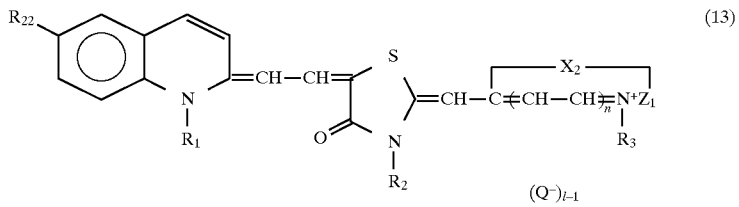

(13)

wherein

Q, n and 1 all have the same meanings as defined in General formula (1);

$X_2$ is S or —CH=CH—;

$Z_1$ is an atomic group necessary to form a thiazoline ring series, a benzothiazole ring series, a naphthothiazole ring series or a 4-quinoline ring series;

$R_1$, $R_2$ and $R_3$ each is an unsubstituted or substituted alkyl group having from 1 to 8 carbon atoms;

$R_{22}$ is a hydrogen atom, an unsubstituted or substituted alkyl group, an unsubstituted or substituted alkoxy group or a halogen atom.

Further, among the compounds of the General Formula (13), more preferred are those where the ring formed by $Z_1$ is a thiazoline ring, a α-naphthothiazole ring or a 4-quinoline ring; $R_1$ and $R_3$ each is a methyl group or an ethyl group; $R_2$ is an ethyl group or a vinyl methyl group; and $R_{22}$ is a hydrogen atom, a methyl group, an ethoxy group or a chlorine atom.

In the compounds of the General Formula (6), those represented by the General Formula (14) are preferred.

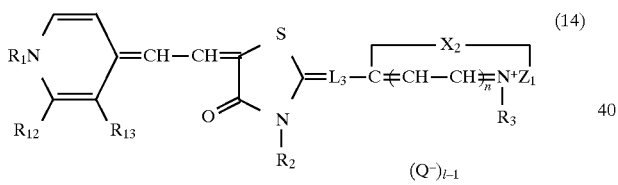

(14)

wherein $R_1$, $R_3$, $L_3$, Q, n and 1 all have the same meanings as defined in the General formula (1);

$X_2$ is S or —CH=CH—;

$Z_1$ is an atomic group necessary to form benzothiazole ring series, a naphthothiazole ring series or a 4-quinoline ring series;

$R_2$ is an unsubstituted or substituted alkyl group; and $R_{12}$ and $R_{13}$ each is a hydrogen atom or an unsubstituted or substituted alkyl group, and $R_{12}$ and $R_{13}$ may combine and form an unsaturated or saturated 6-membered ring.

Further, among the compounds of the General Formula (14), those where $X_2$ is S; the ring formed by $Z_1$ is a benzothiazole ring series or a naphthothiazole ring series; $R_1$, $R_2$ and $R_3$ each is an alkyl group having from 1 to 8 carbon atoms; $R_{12}$ and $R_{13}$ each is a hydrogen atom; and $L_3$ is a methine group and most preferred are those where the ring formed by $Z_1$ is a benzothiazole ring series; and $R_1$, $R_2$ and $R_3$ each is a methyl group or an ethyl group are more preferred.

In the compounds of the General Formula (6), those represented by the General Formula (15) are also preferred.

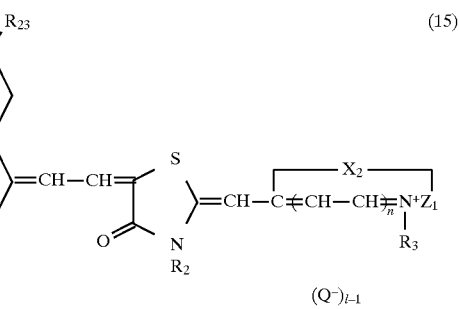

(15)

wherein

Q, n, and 1 all have the same meanings as defined in the General formula (1);

$X_2$ is S or —CH=CH—;

$Z_1$ is an atomic group necessary to form a benzothiazole ring series, a naphthothiazole ring series or a 4-quinoline ring series;

$R_1$, $R_2$ and $R_3$ each is an unstbstituted or substituted alkyl group having from 1 to 8 carbon atoms; and $R_{23}$ is a hydrogen atom, an unsubstituted or substituted alkoxy group, an unsubstituted or substituted acylamino group, a halogen atom or a halogenated alkyl group.

Among the compounds of the General Formula (15), those where $X_2$ is S; the ring formed by $Z_1$ is an α-naphthothiazole ring or a β-naphthothiazole ring; $R_1$ and $R_3$ each is a methyl group or an ethyl group; $R_2$ is a methyl group, an ethyl group or a vinyl methyl group; and $R_{23}$ is a hydrogen atom are more preferred.

The compounds of the General Formulas (1)–(6) described above can be easily produced from known starting materials in accordance with the methods disclosed in British Patent Nos. 487,051 and 489,335 and U.S. Pat. Nos. 2,536,986, 2,454,629, 2,961,318, 2,388,963 and 2,504,468, the disclosures of which are incorporated herein by reference.

Typical examples of compounds of General Formula (1) to (6) which can be employed in this invention include the following compounds; however, the present invention is not to be construed as being limited to these compounds.

| Compound No. | Structure |
|---|---|
| 1 | 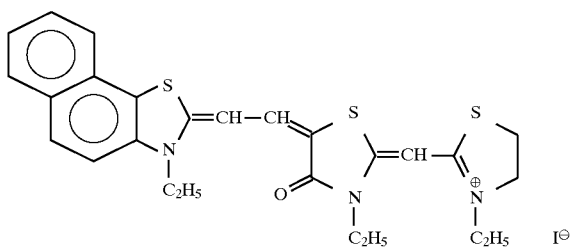 |
| 2 | 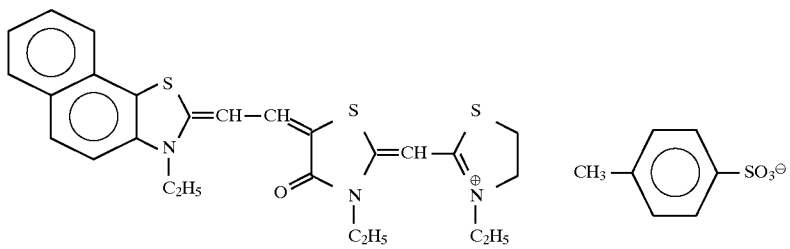 |
| 3 | 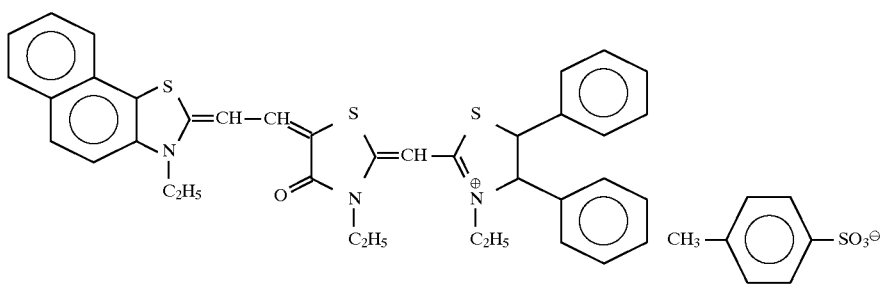 |
| 4 | 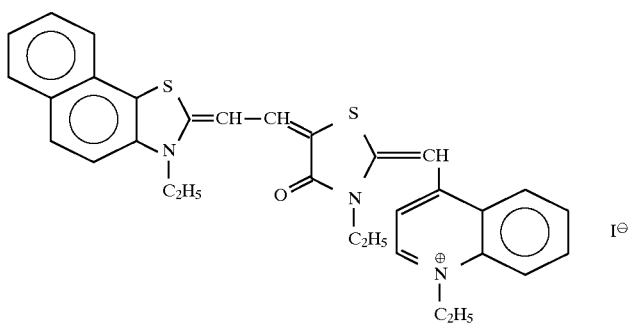 |
| 5 | 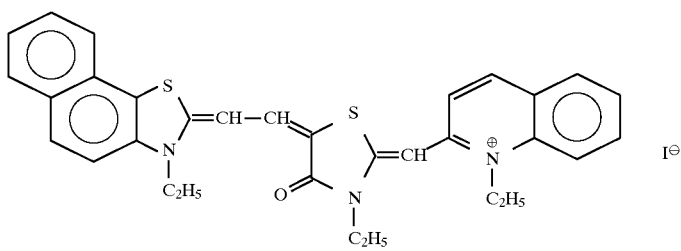 |
| 6 | 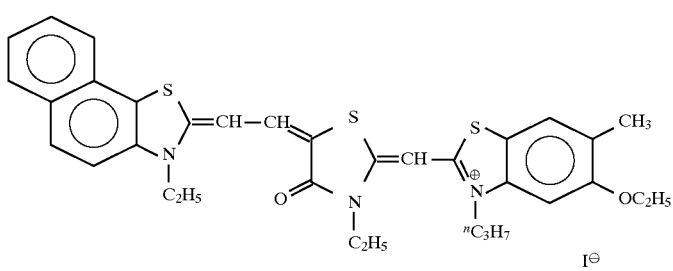 |

| Compound No. | Structure |
|---|---|
| 7 | 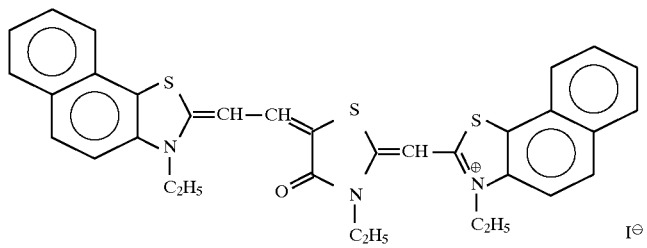 |
| 8 | 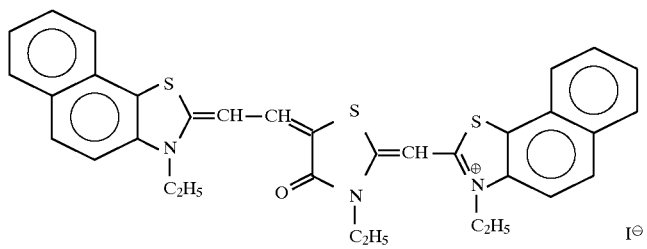 |
| 9 | 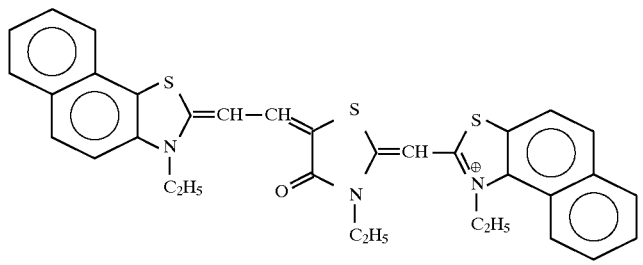 |
| 10 | 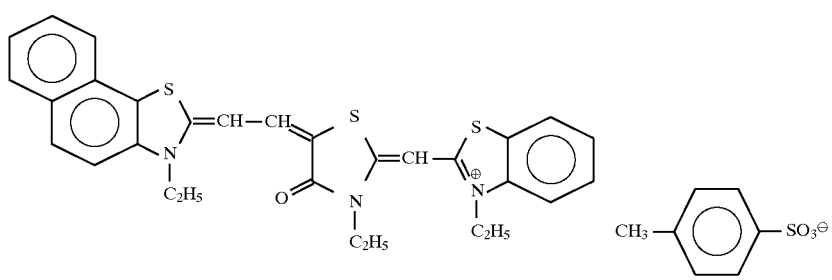 |
| 11 | 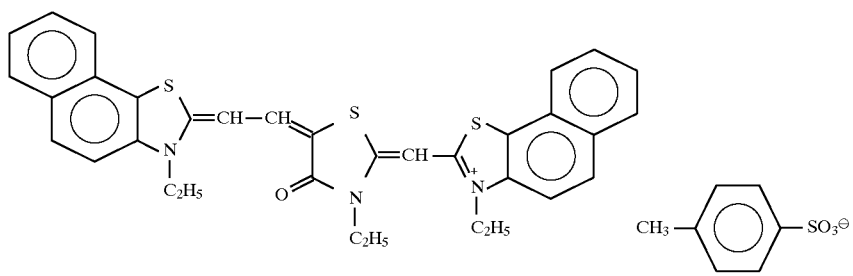 |
| 12 | 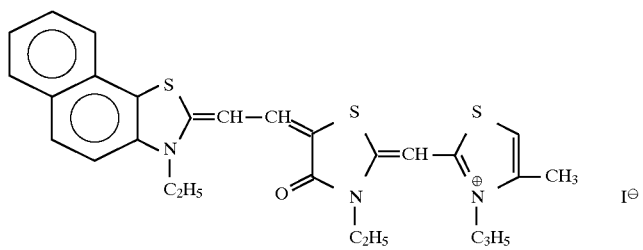 |

| Compound No. | Structure |
|---|---|
| 13 | 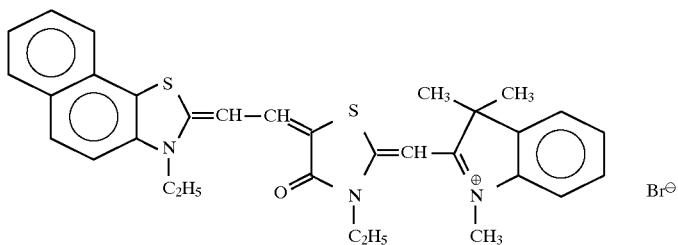 |
| 14 | 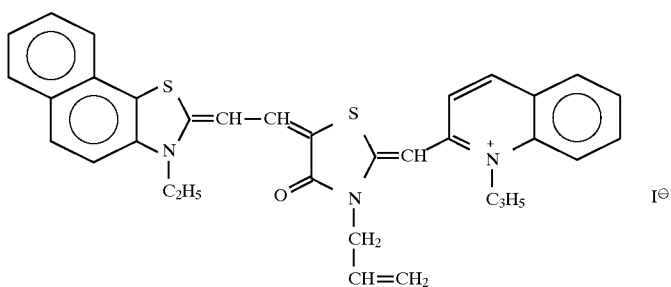 |
| 15 | 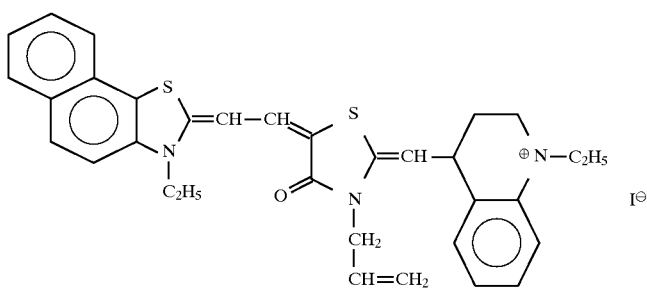 |
| 16 | 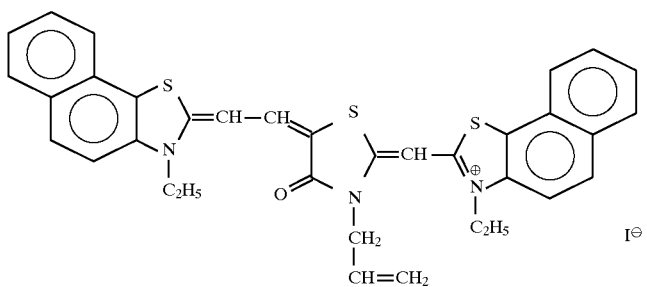 |
| 17 | 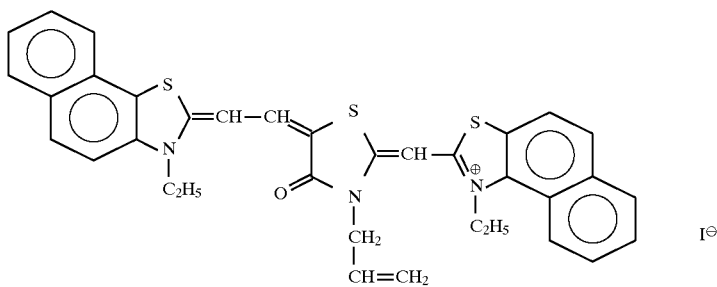 |

-continued
| Compound No. | Structure |
|---|---|
| 18 | 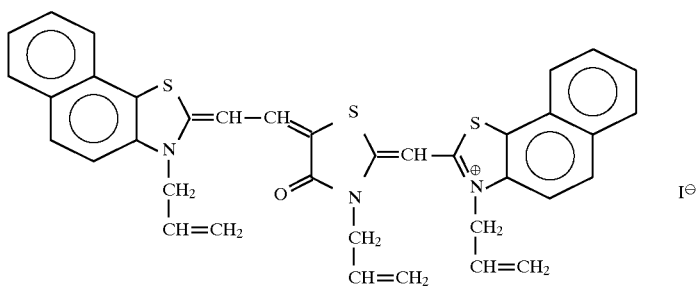 |
| 19 | 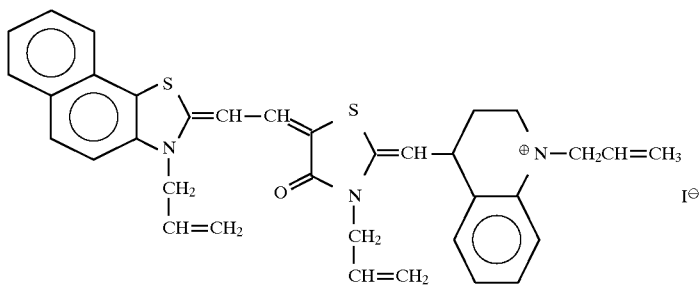 |
| 20 | 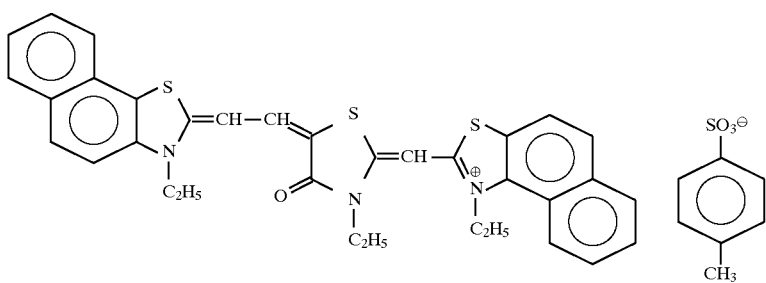 |
| 21 | 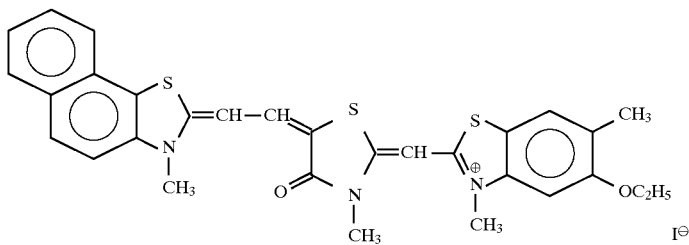 |
| 22 | 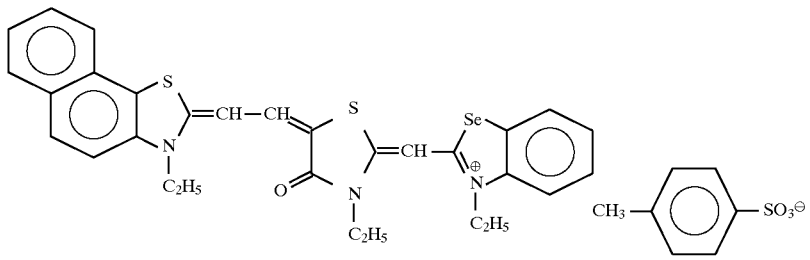 |
| 23 | 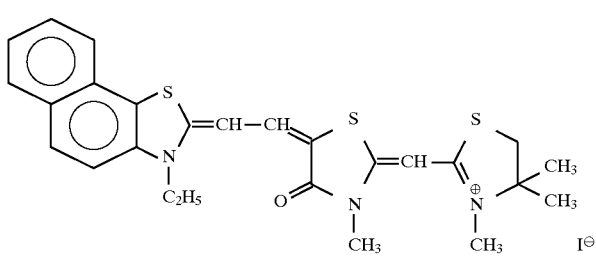 |

-continued
| Compound No. | Structure |
|---|---|
| 24 | 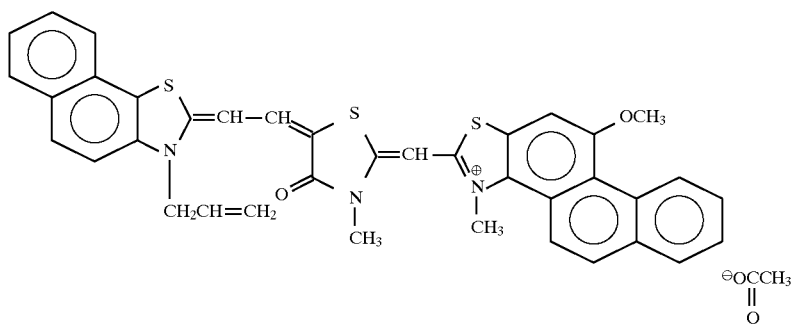 |
| 25 | 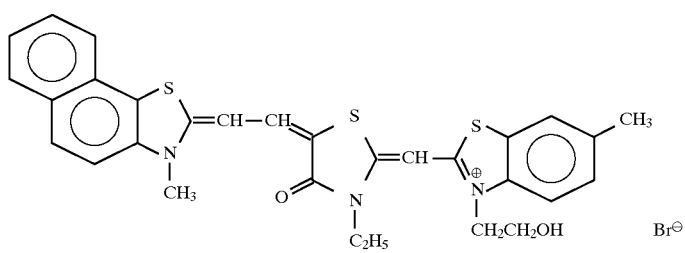 |
| 26 | 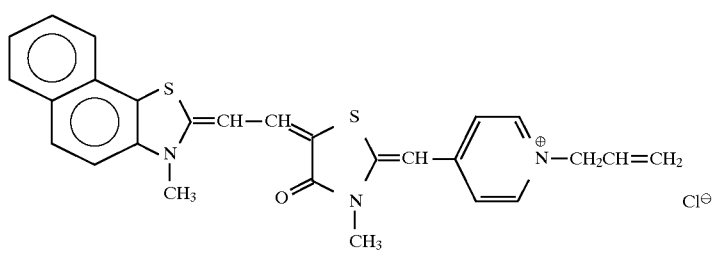 |
| 27 | 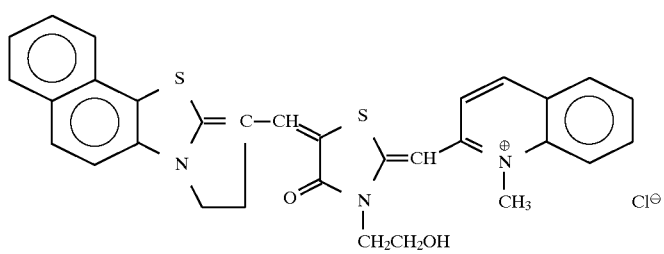 |
| 28 | 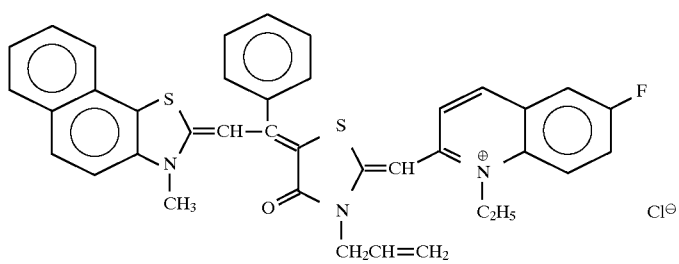 |
| 29 | 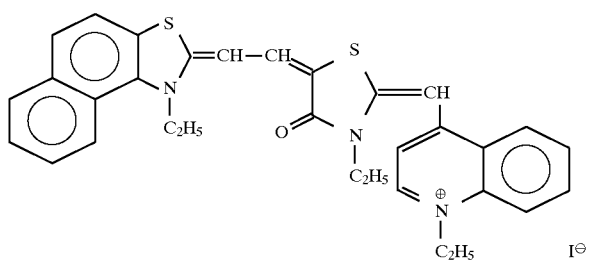 |

-continued
| Compound No. | Structure |
|---|---|
| 30 | 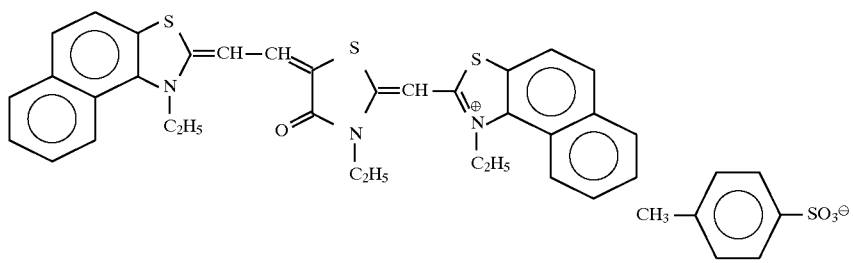 |
| 31 | 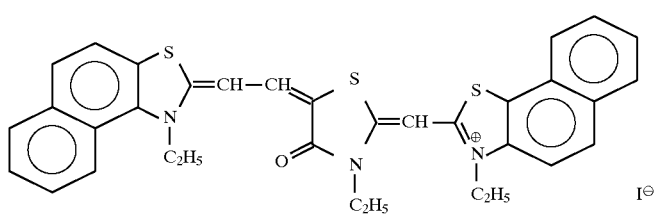 |
| 32 | 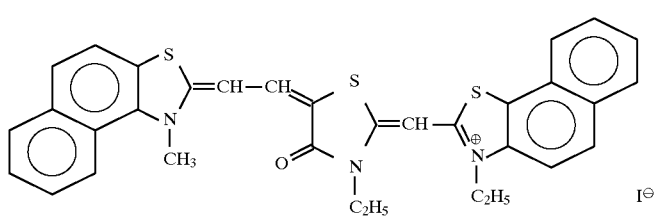 |
| 33 | 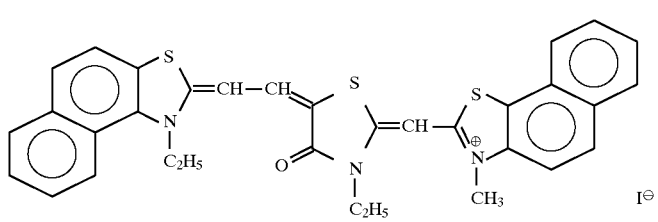 |
| 34 | 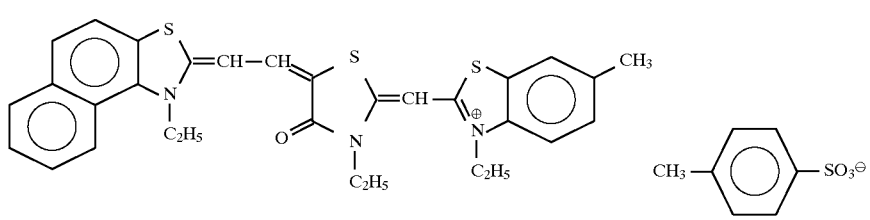 |
| 35 | 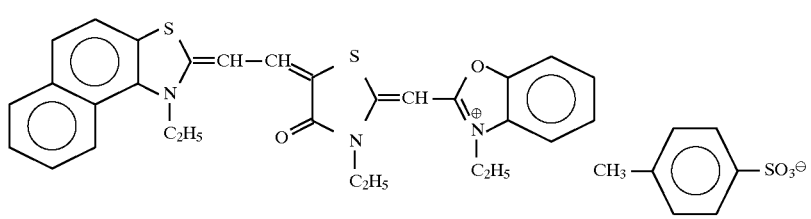 |
| 36 | 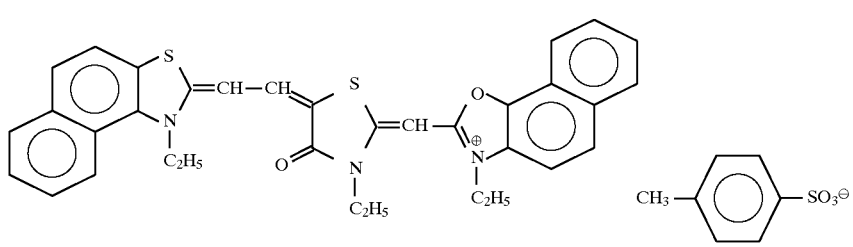 |

-continued
| Compound No. | Structure |
|---|---|
| 37 | 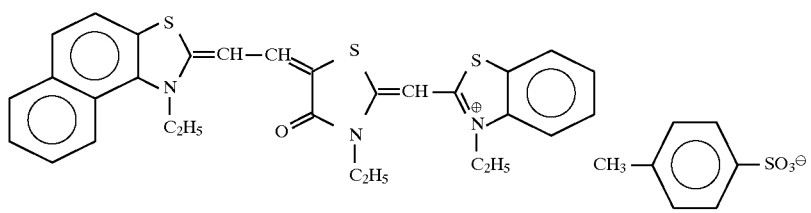 |
| 38 | 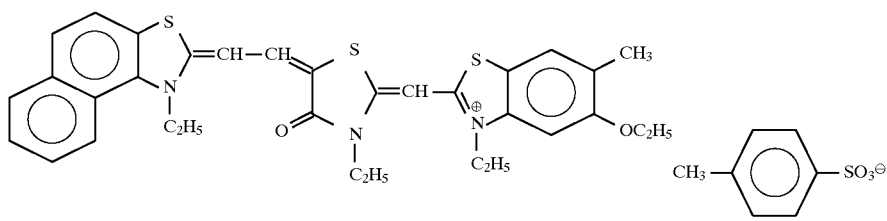 |
| 39 | 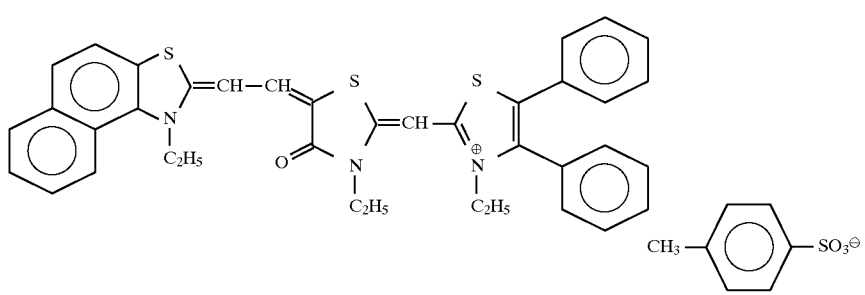 |
| 40 | 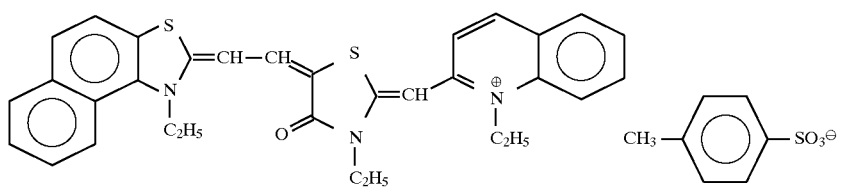 |
| 41 | 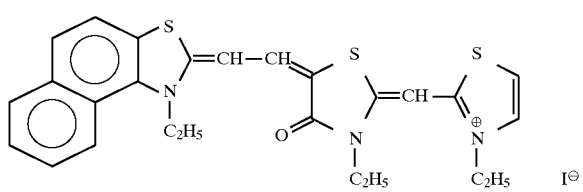 |
| 42 | 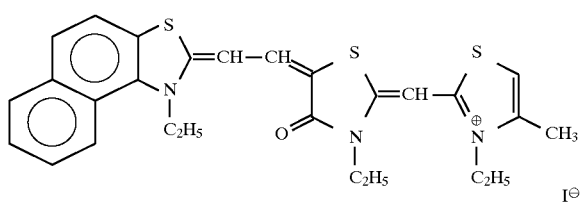 |
| 43 | 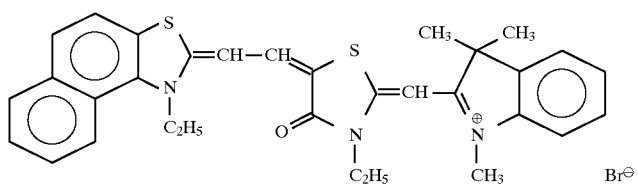 |

| Compound No. | Structure |
|---|---|
| 44 | 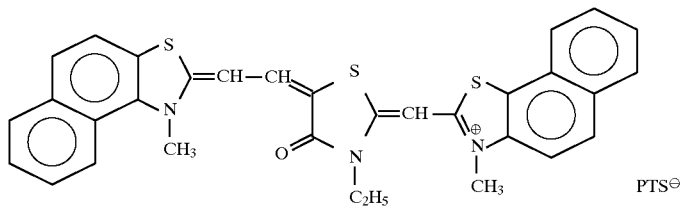 PTS<sup>⊖</sup> |
| 45 | 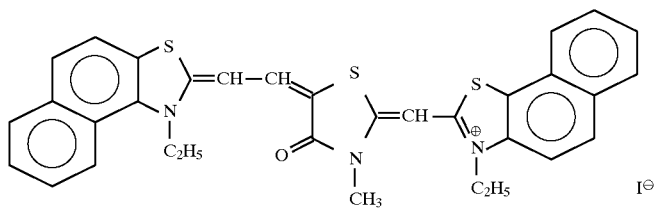 I<sup>⊖</sup> |
| 46 | 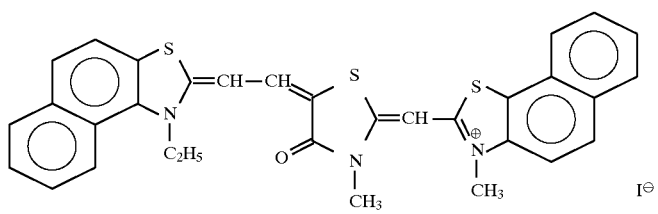 I<sup>⊖</sup> |
| 47 | 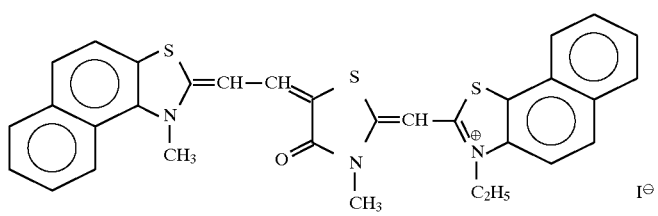 I<sup>⊖</sup> |
| 48 | 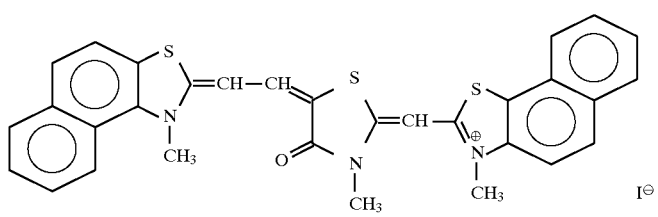 I<sup>⊖</sup> |
| 49 | 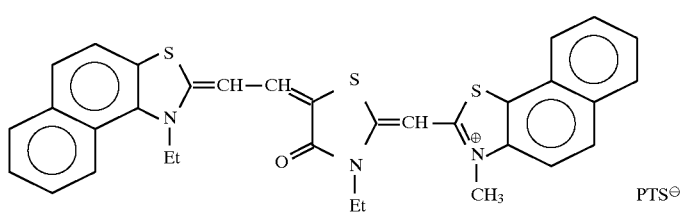 PTS<sup>⊖</sup> |
| 50 | 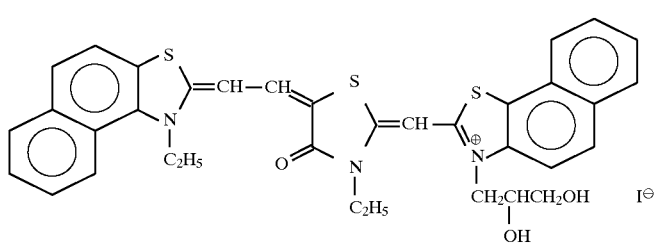 I<sup>⊖</sup> |

5,861,424
-continued
| Compound No. | Structure |
|---|---|
| 51 | 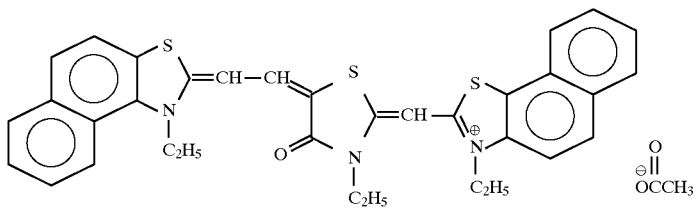 |
| 52 | 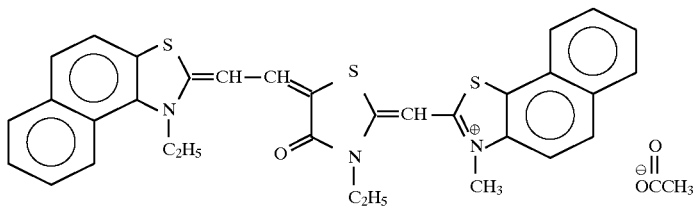 |
| 53 | 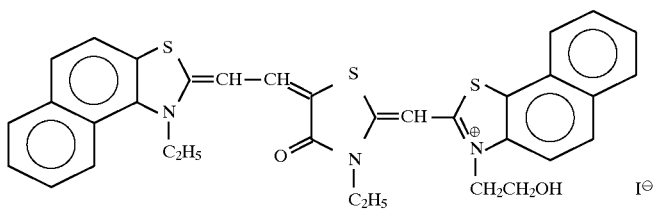 |
| 54 | 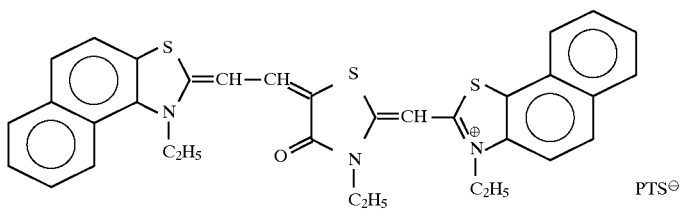 |
| 55 | 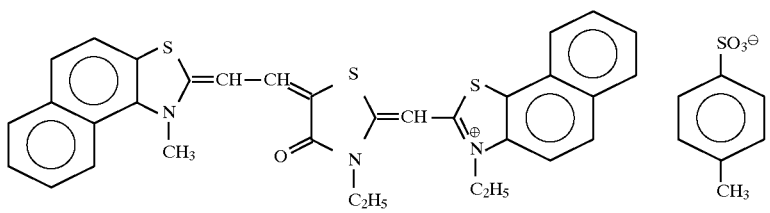 |
| 56 | 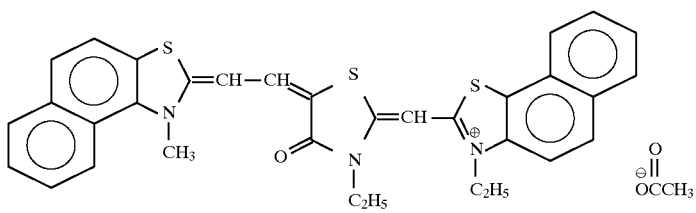 |
| 57 | 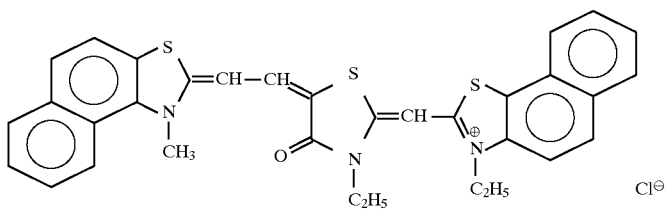 |

| Compound No. | Structure |
|---|---|
| 58 | 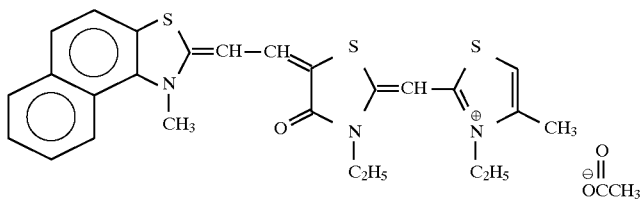 |
| 59 | 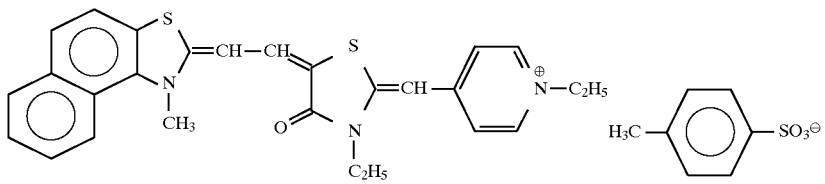 |
| 60 | 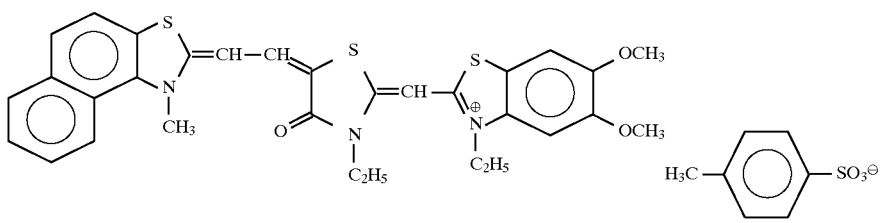 |
| 61 | 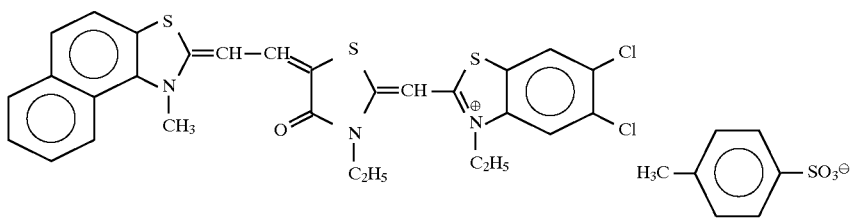 |
| 62 | 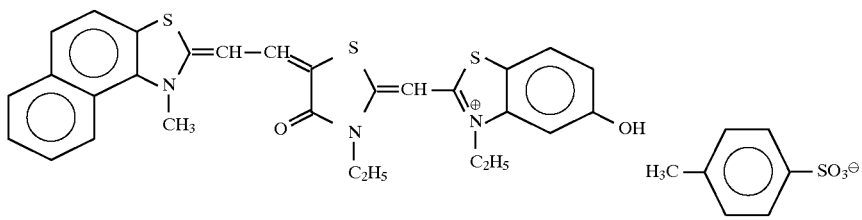 |
| 63 | 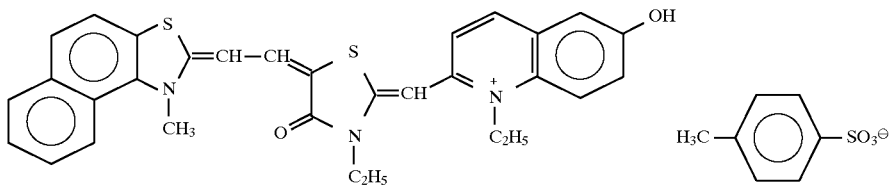 |
| 64 | 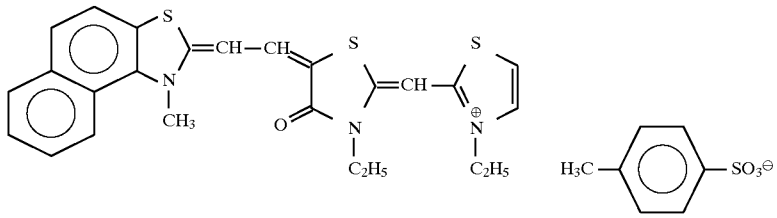 |

| Compound No. | Structure |
|---|---|
| 65 | 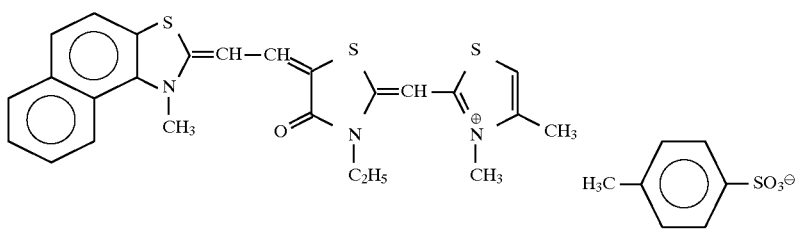 |
| 66 | 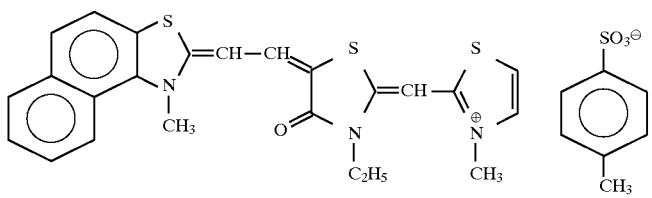 |
| 67 | 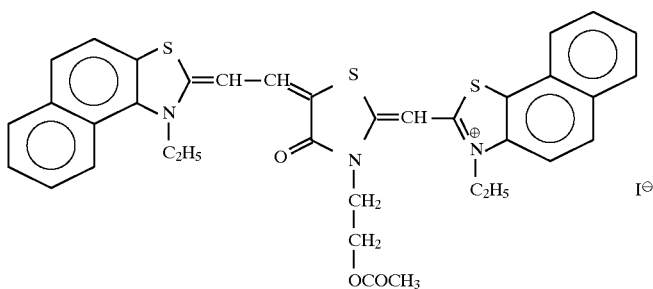 |
| 68 | 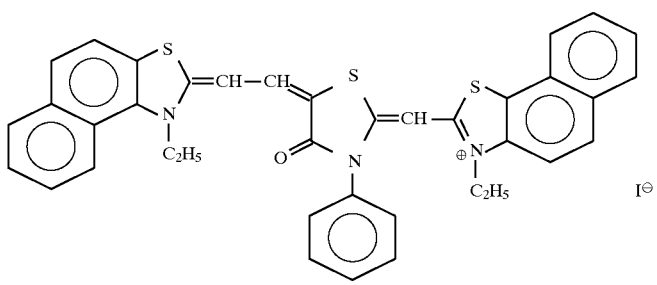 |
| 69 | 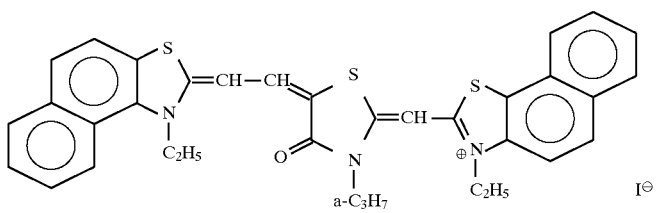 |
| 70 | 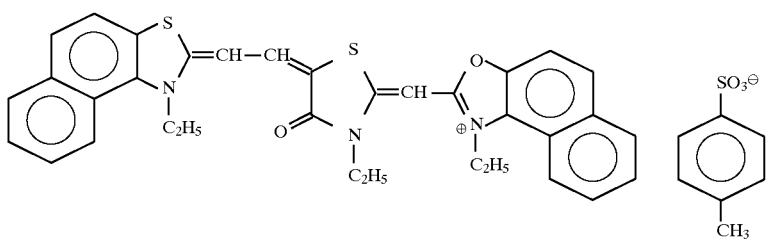 |

| Compound No. | Structure |
|---|---|
| 71 | 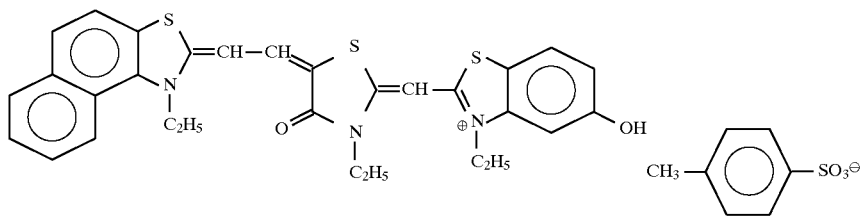 |
| 72 | 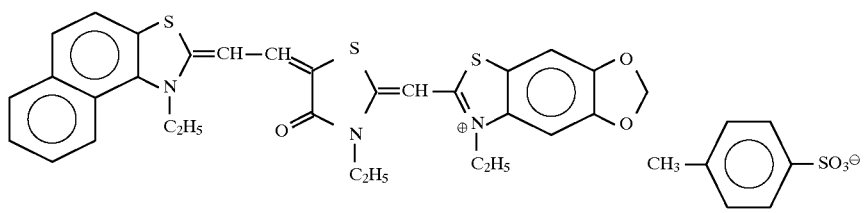 |
| 73 | 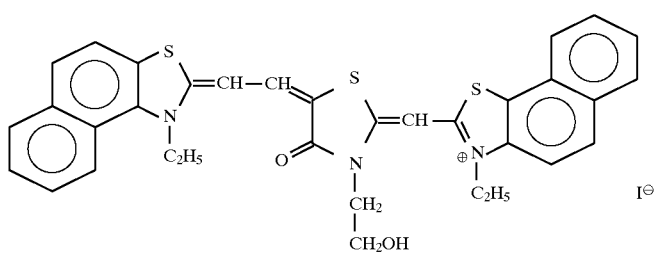 |
| 74 | 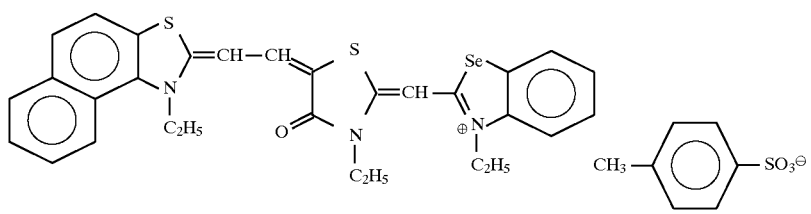 |
| 75 | 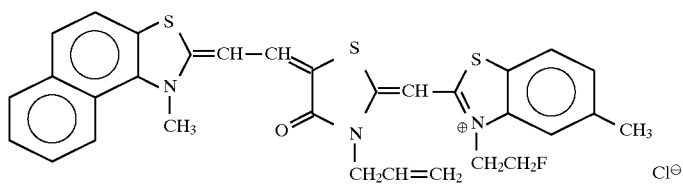 |
| 76 | 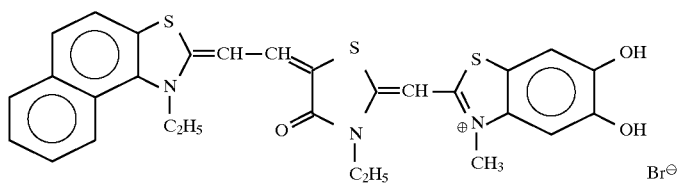 |
| 77 | 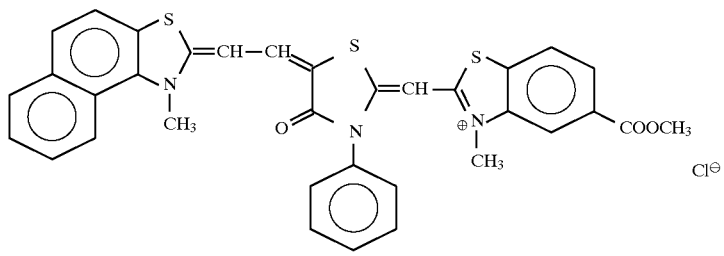 |

-continued
| Compound No. | Structure |
|---|---|
| 78 | 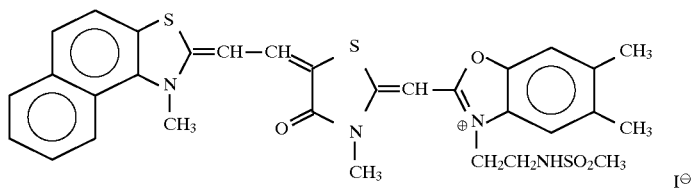 |
| 79 | 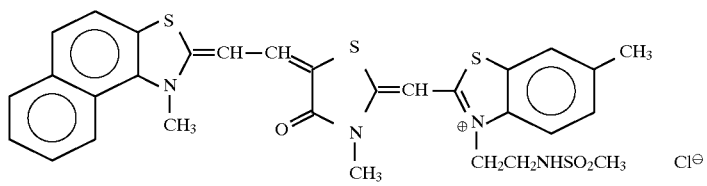 |
| 80 | 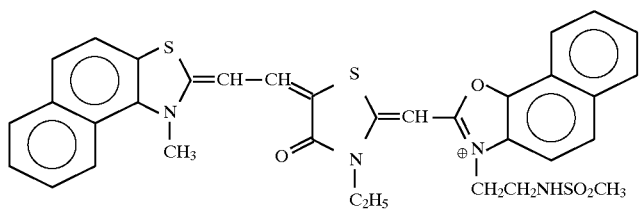 |
| 81 | 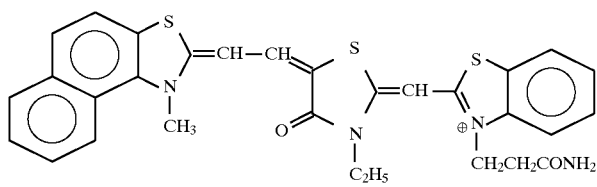 |
| 82 | 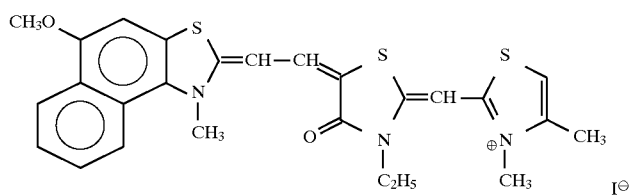 |
| 83 | 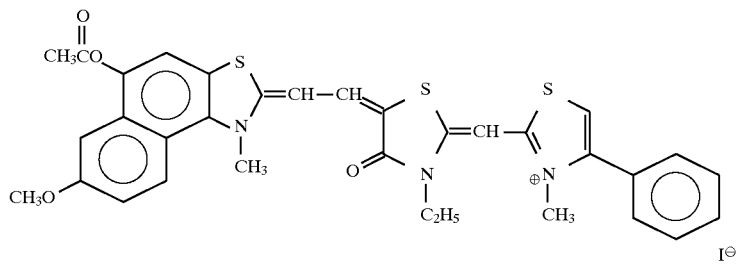 |
| 84 | 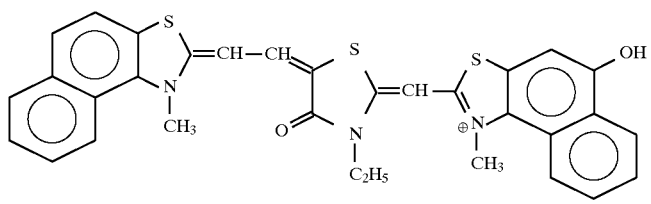 |

| Compound No. | Structure |
|---|---|
| 85 | 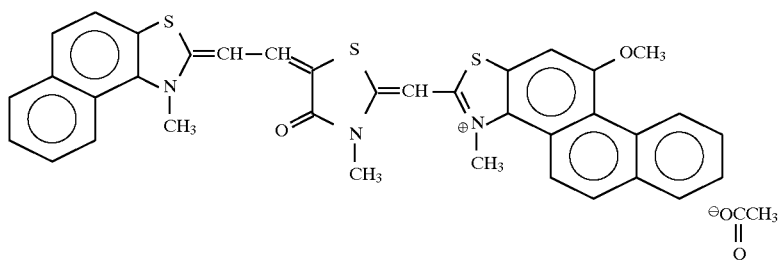 |
| 86 | 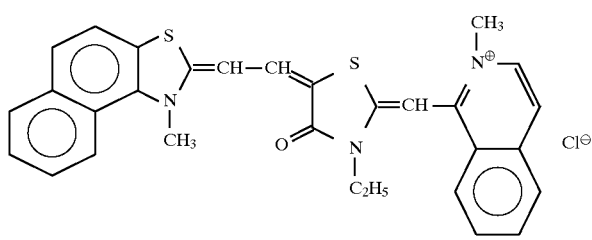 |
| 87 | 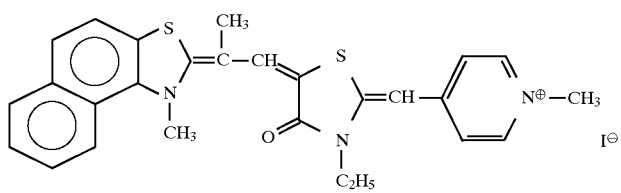 |
| 88 | 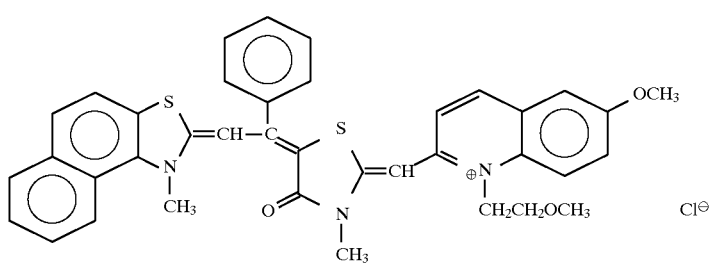 |
| 89 | 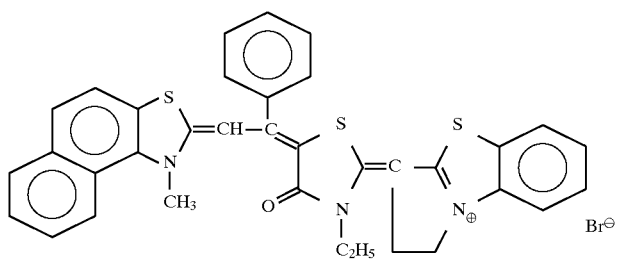 |
| 90 | 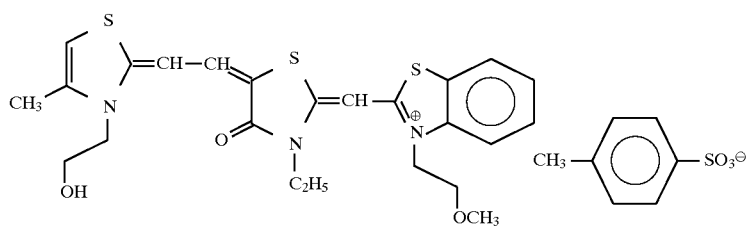 |

| Compound No. | Structure |
|---|---|
| 91 | 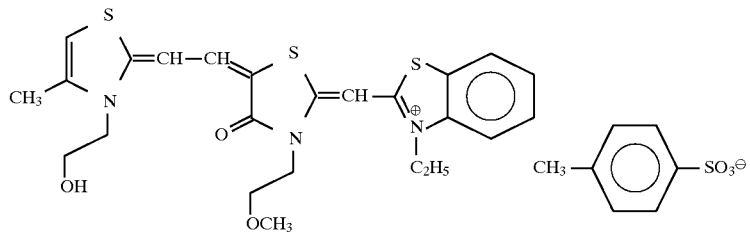 |
| 92 | 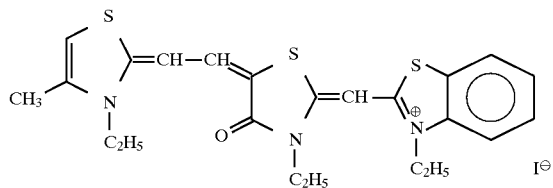 |
| 93 | 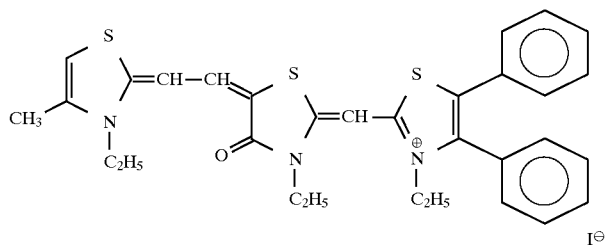 |
| 94 | 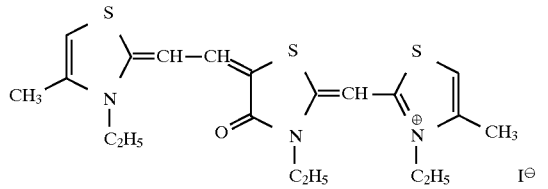 |
| 95 | 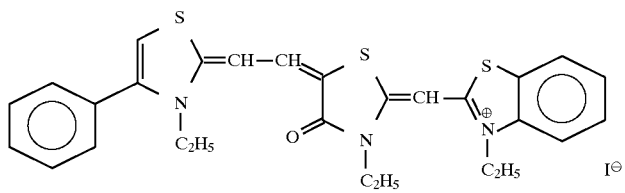 |
| 96 | 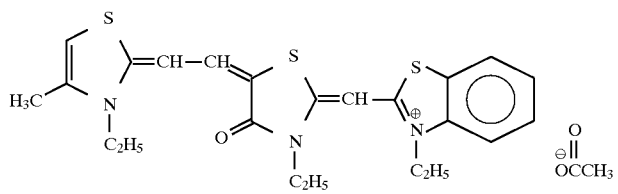 |
| 97 | 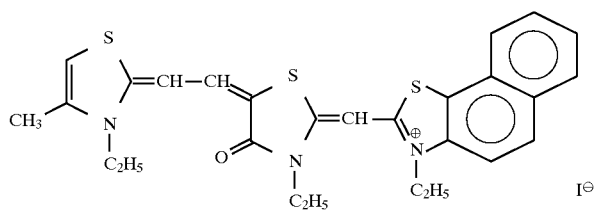 |

5,861,424
47                                                                                        48
                                    -continued
| Compound No. | Structure |
|---|---|
| 98  | 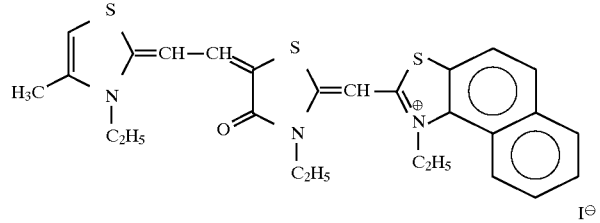 |
| 99  | 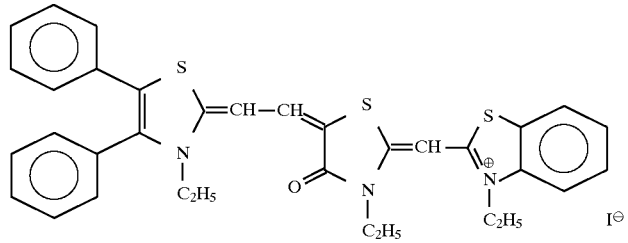 |
| 100 | 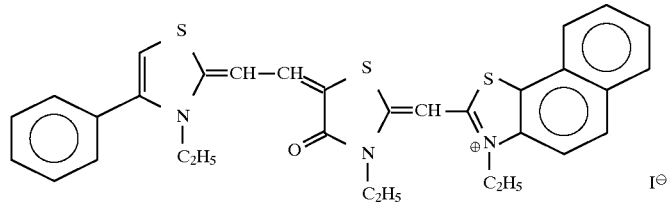 |
| 101 | 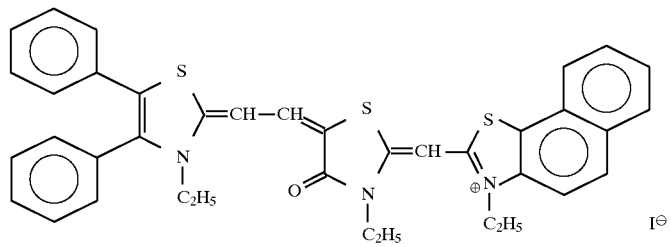 |
| 102 | 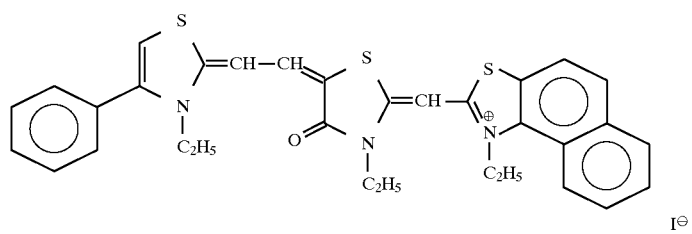 |
| 103 | 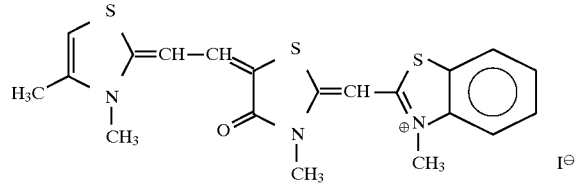 |
| 104 | 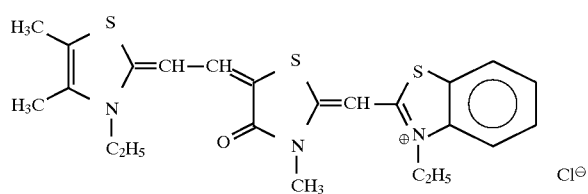 |

| Compound No. | Structure |
|---|---|
| 105 | 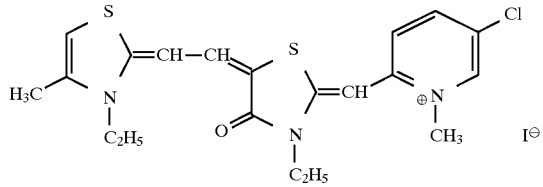 |
| 106 | 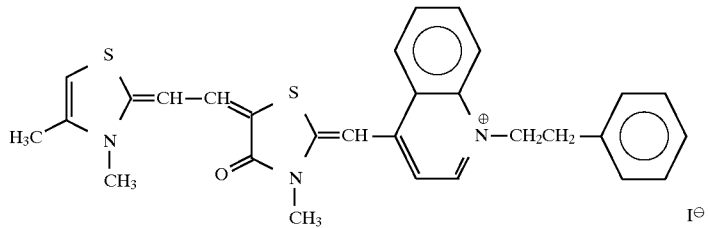 |
| 107 | 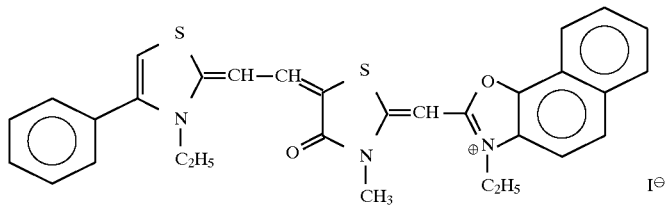 |
| 108 | 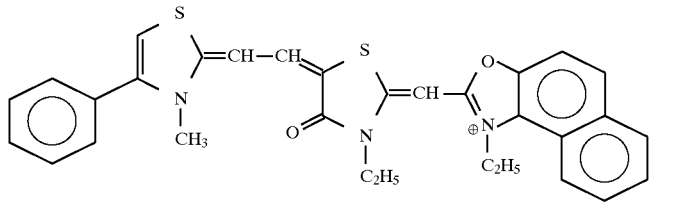 |
| 109 | 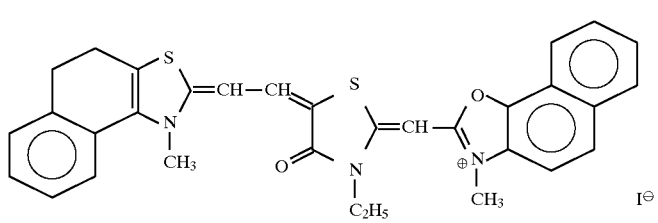 |
| 110 | 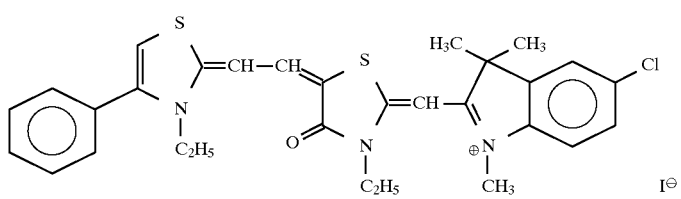 |
| 111 | 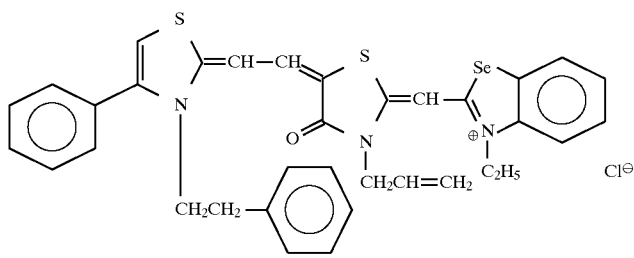 |

| Compound No. | Structure |
|---|---|
| 112 | 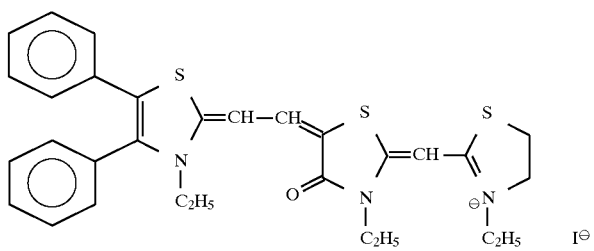 |
| 113 | 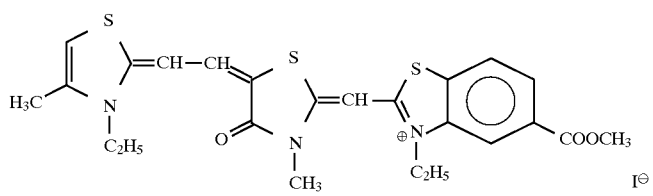 |
| 114 | 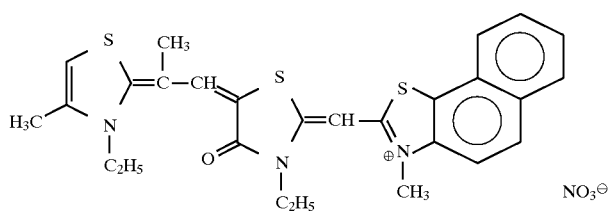 |
| 115 | 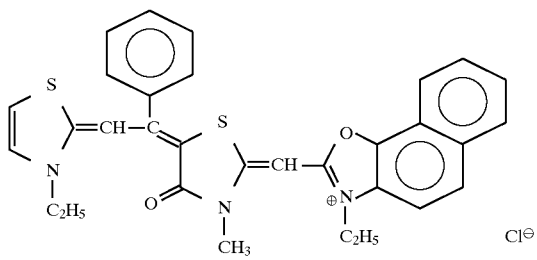 |
| 116 | 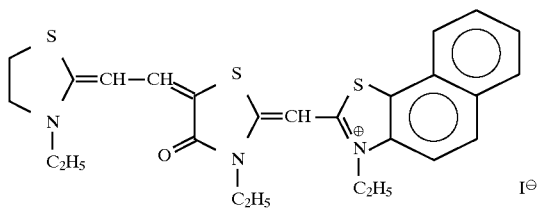 |
| 117 | 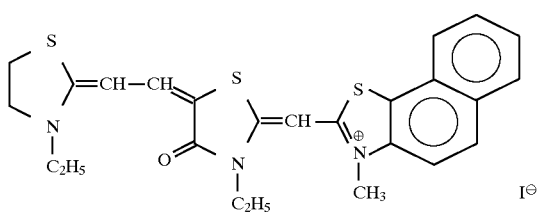 |
| 118 | 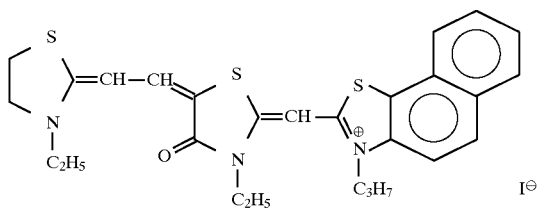 |

| Compound No. | Structure |
|---|---|
| 119 | 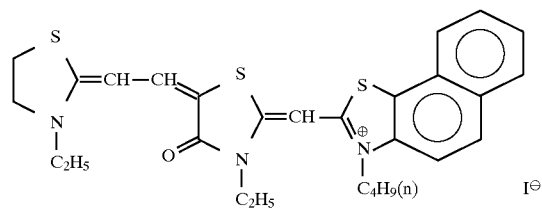 |
| 120 | 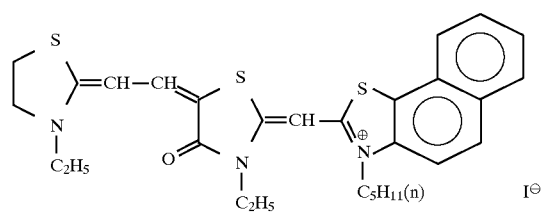 |
| 121 | 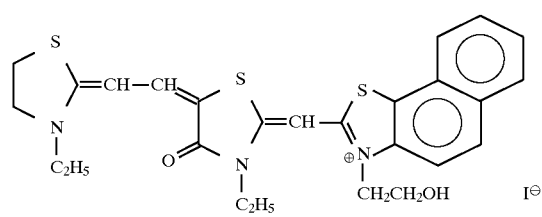 |
| 122 | 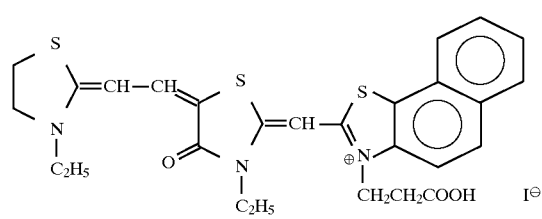 |
| 123 | 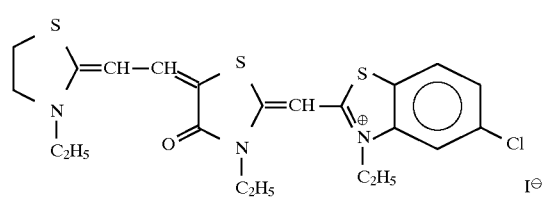 |
| 124 | 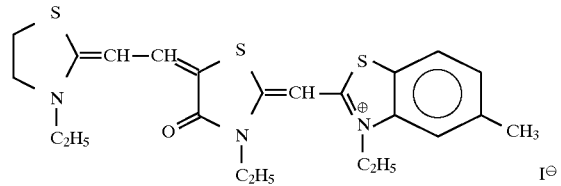 |
| 125 | 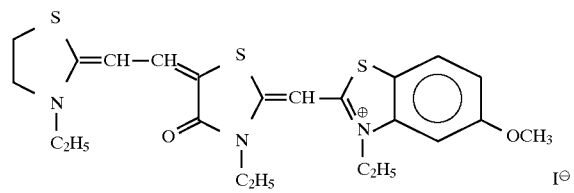 |

-continued

| Compound No. | Structure |
|---|---|
| 126 | (structure with 5-OH benzothiazole) |
| 127 | (structure with 5-CO₂CH₃ benzothiazole) |
| 128 | (structure with 5-Br benzothiazole) |
| 129 | (structure with 5-phenyl benzothiazole) |
| 130 | (structure with 5-NHCOCH₃ benzothiazole) |
| 131 | (structure with 6-CH₃ benzothiazole) |
| 132 | (structure with 6-OH benzothiazole) |
| 133 | (structure with 6-CH₃, 5-OC₂H₅ benzothiazole) |

| Compound No. | Structure |
|---|---|
| 134 | 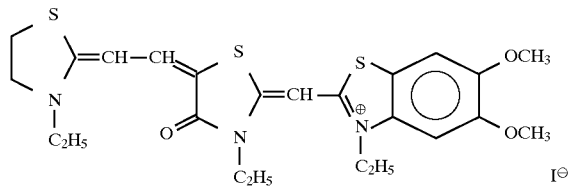 |
| 135 | 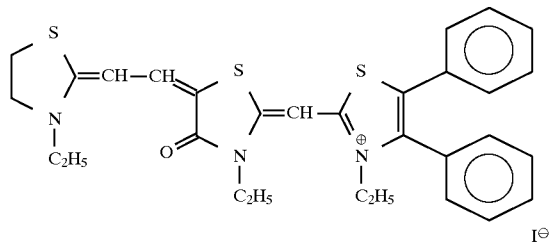 |
| 136 | 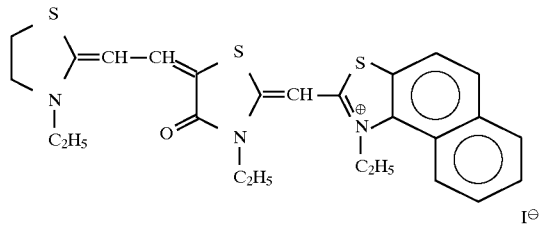 |
| 137 | 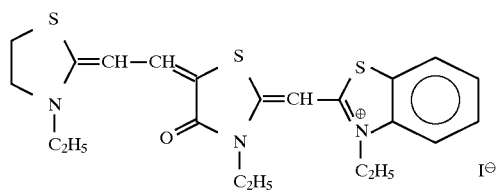 |
| 138 | 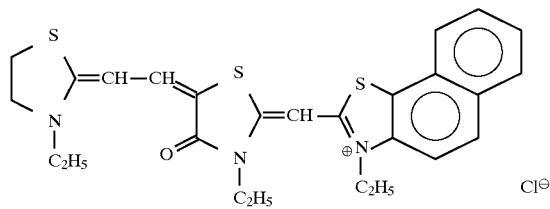 |
| 139 | 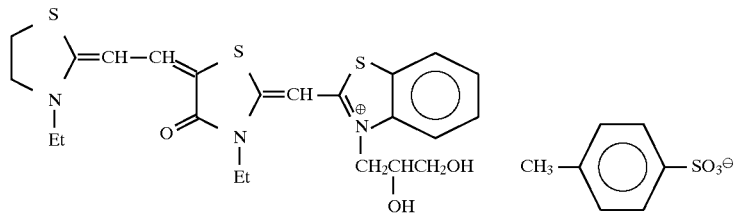 |
| 140 | 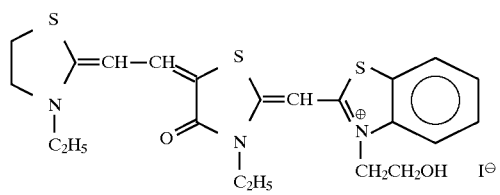 |

| Compound No. | Structure |
|---|---|
| 141 | 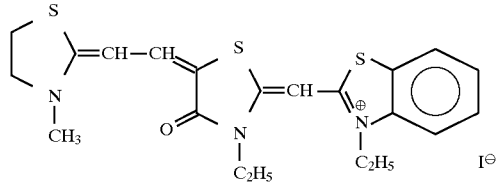 |
| 142 | 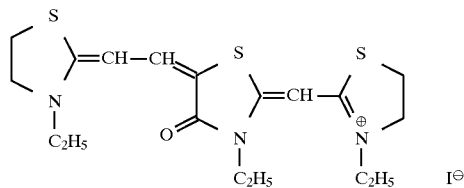 |
| 143 | 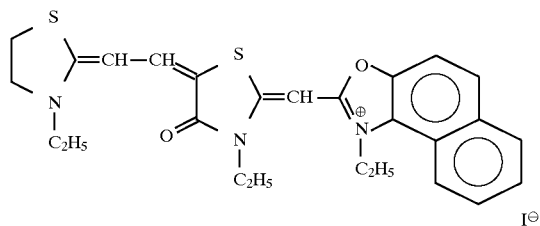 |
| 144 | 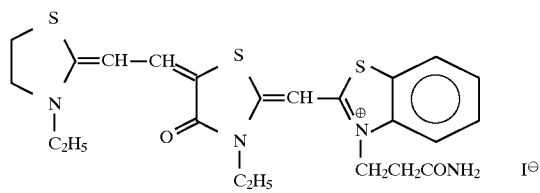 |
| 145 | 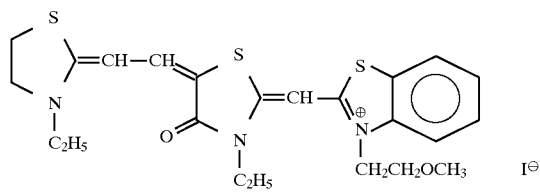 |
| 146 | 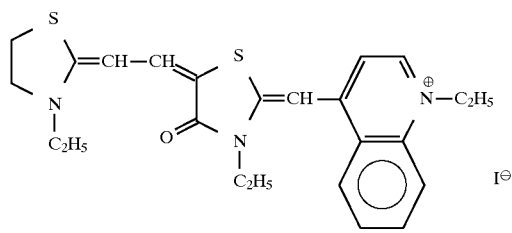 |
| 147 | 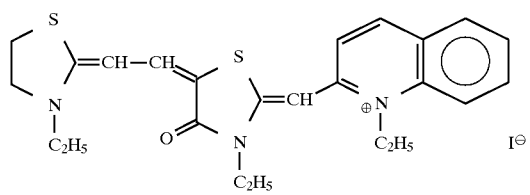 |

| Compound No. | Structure |
|---|---|
| 148 | 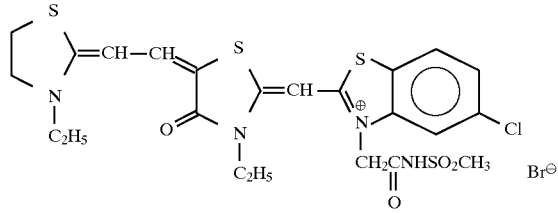 |
| 149 | 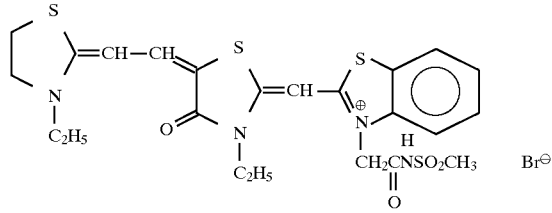 |
| 150 | 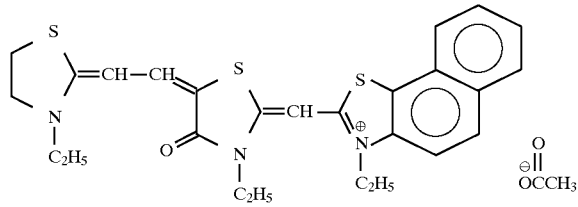 |
| 151 | 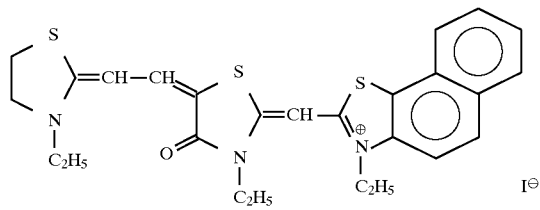 |
| 152 | 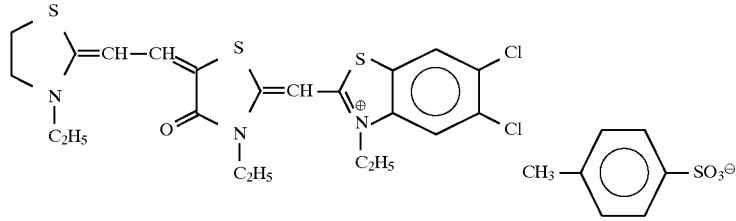 |
| 153 | 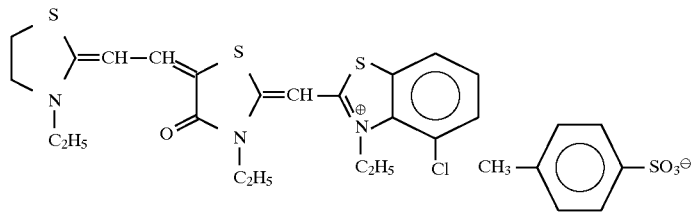 |
| 154 | 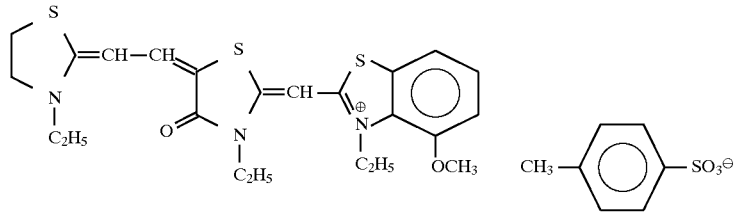 |

| Compound No. | Structure |
|---|---|
| 155 | 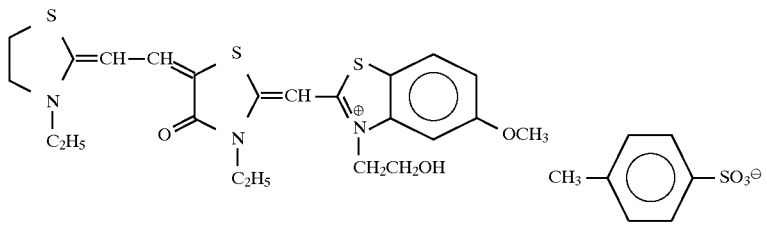 |
| 156 | 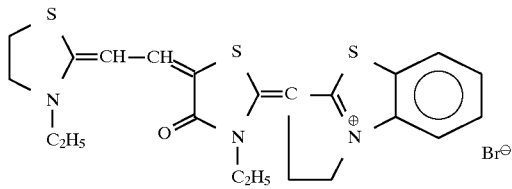 |
| 157 | 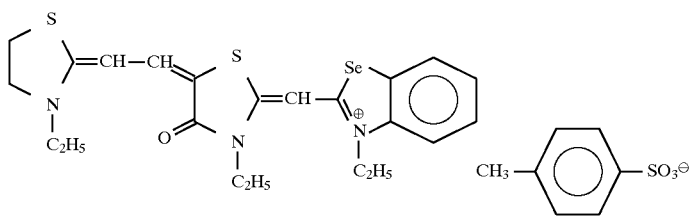 |
| 158 | 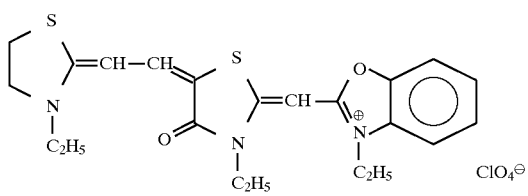 |
| 159 | 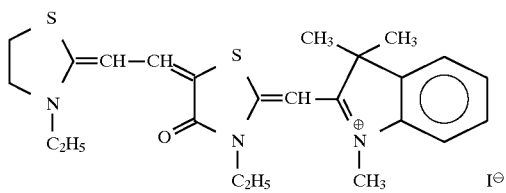 |
| 160 | 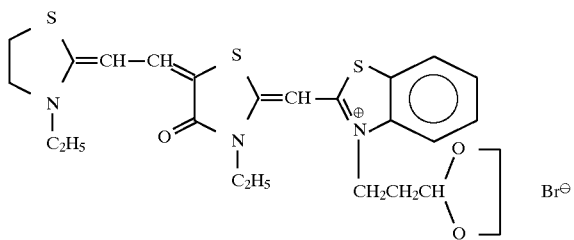 |
| 161 | 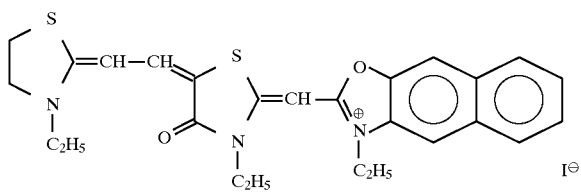 |

| Compound No. | Structure |
|---|---|
| 162 | 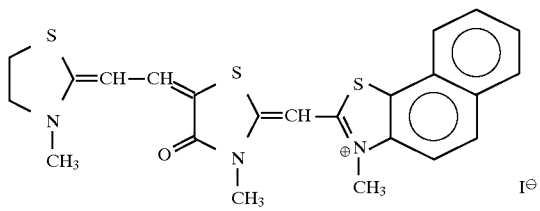 |
| 163 | 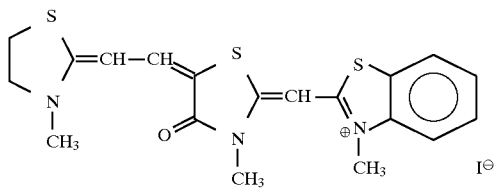 |
| 164 | 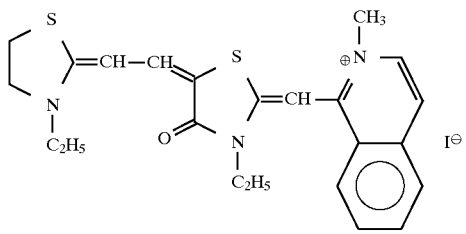 |
| 165 | 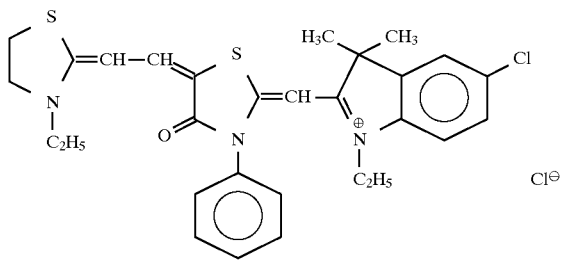 |
| 166 | 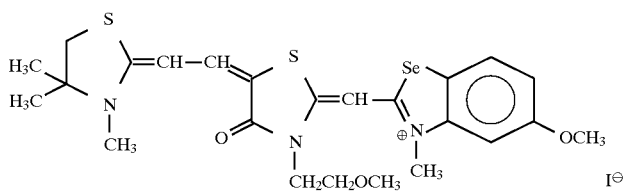 |
| 167 | 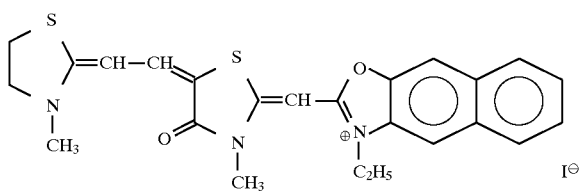 |
| 168 | 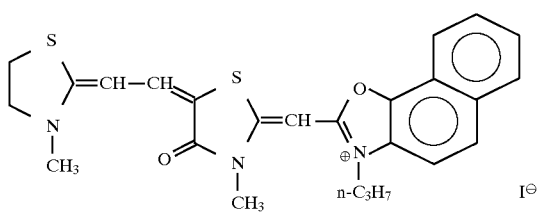 |

| Compound No. | Structure |
|---|---|
| 169 | 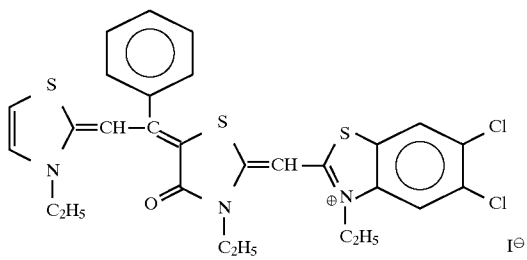 |
| 170 | 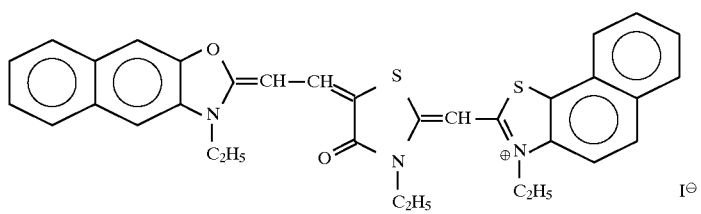 |
| 171 | 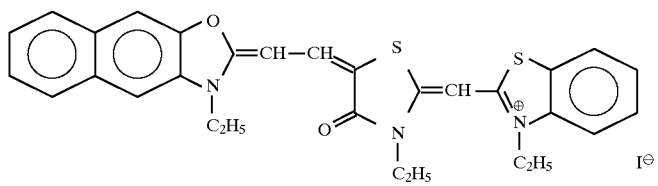 |
| 172 | 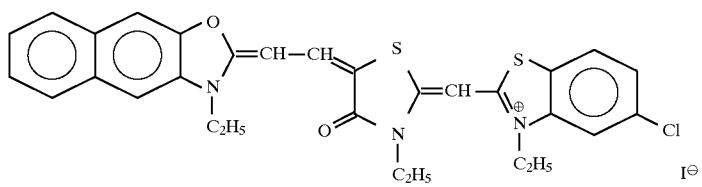 |
| 173 | 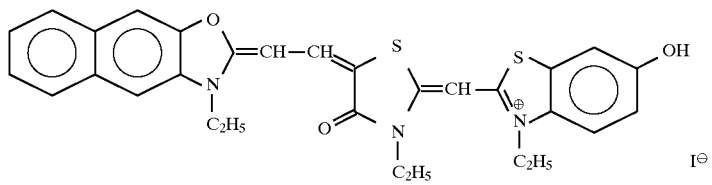 |
| 174 | 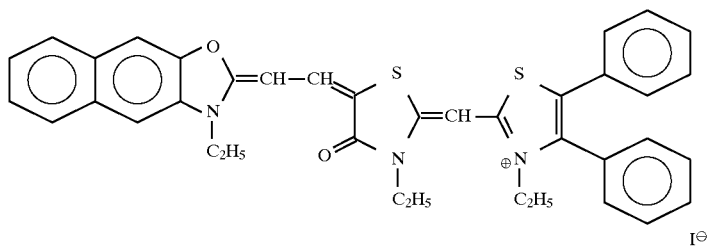 |
| 175 | 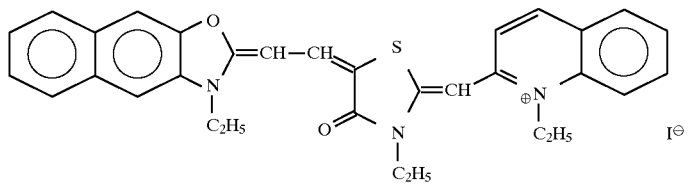 |

| Compound No. | Structure |
|---|---|
| 176 | 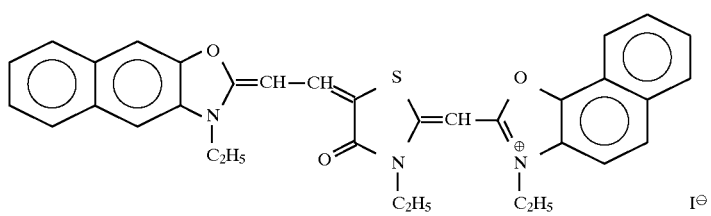 |
| 177 | 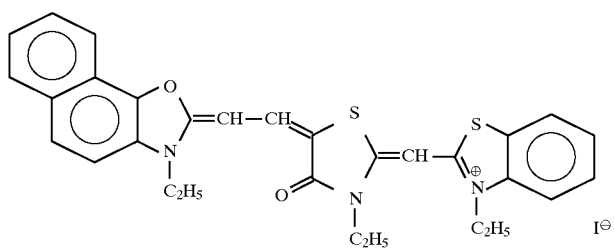 |
| 178 | 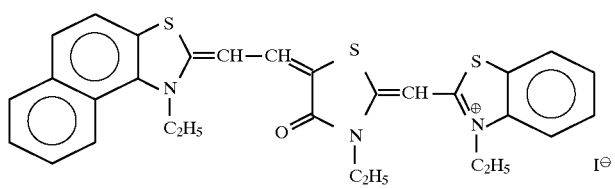 |
| 179 | 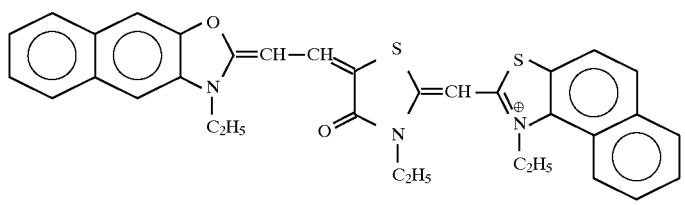 |
| 180 | 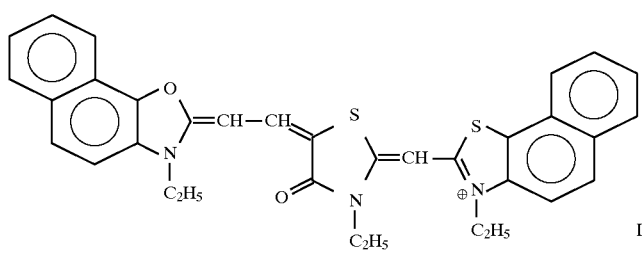 |
| 181 | 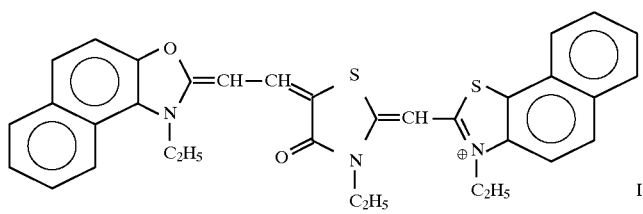 |
| 182 | 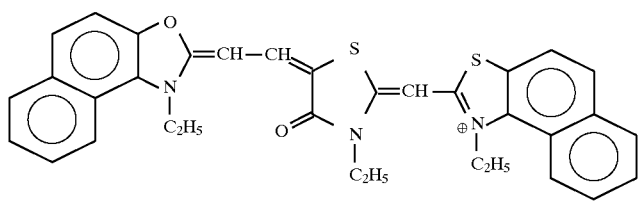 |

| Compound No. | Structure |
|---|---|
| 183 | 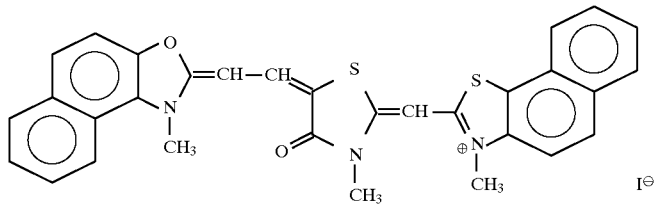 |
| 184 | 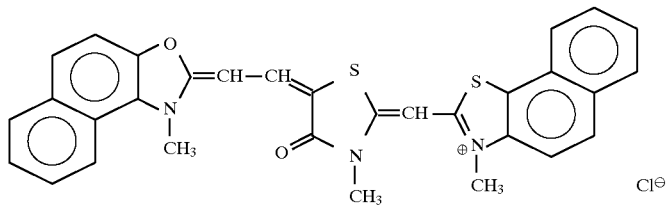 |
| 185 | 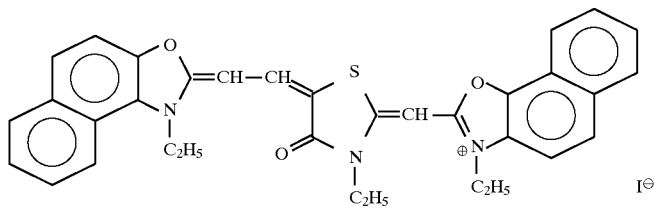 |
| 186 | 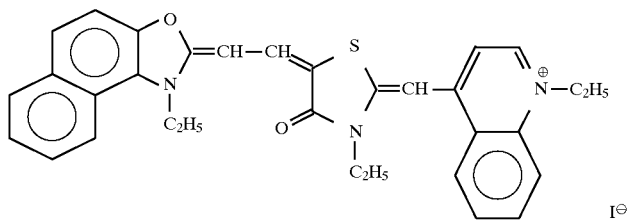 |
| 187 | 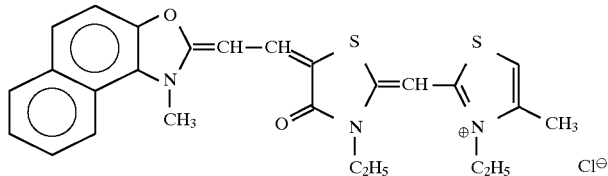 |
| 188 | 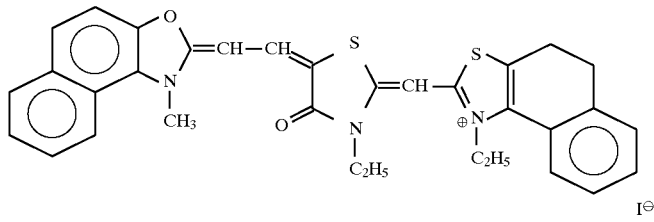 |
| 189 | 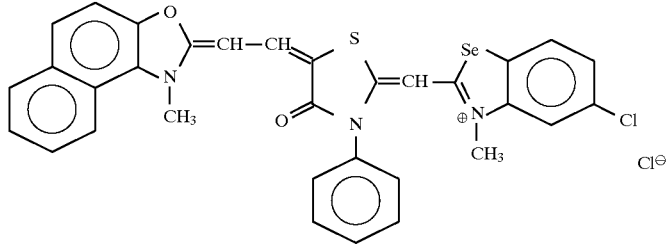 |

-continued

| Compound No. | Structure |
| --- | --- |
| 190 | |
| 191 | |
| 192 | |
| 193 | |
| 194 | |
| 195 | |
| 196 | |

| Compound No. | Structure |
|---|---|
| 197 | 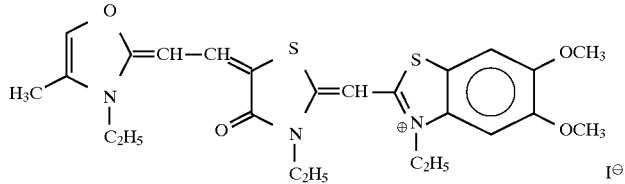 |
| 198 | 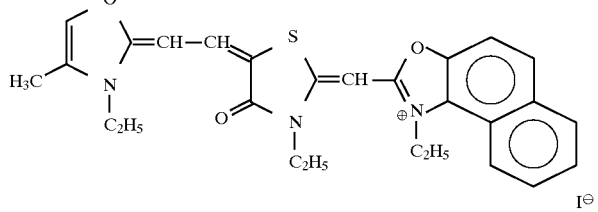 |
| 199 | 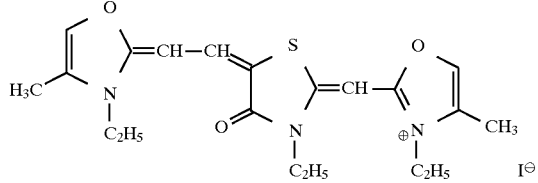 |
| 200 | 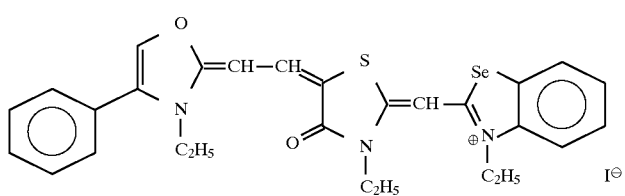 |
| 201 | 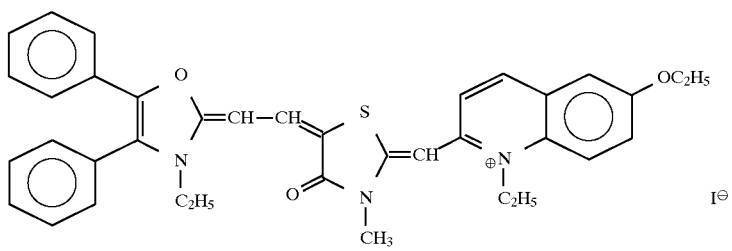 |
| 202 | 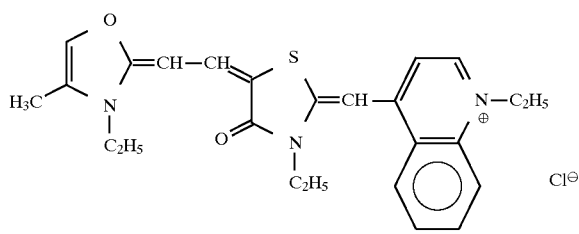 |
| 203 | 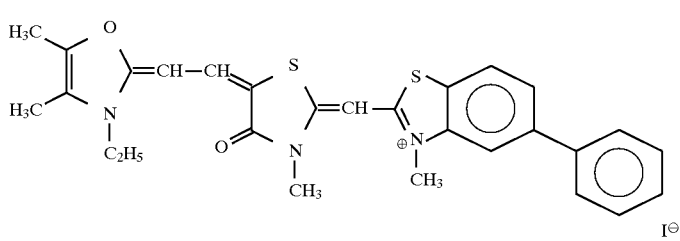 |

| Compound No. | Structure |
|---|---|
| 204 | 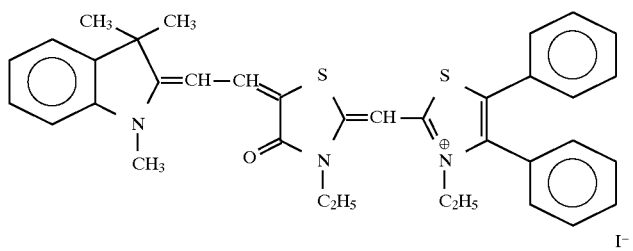 |
| 205 | 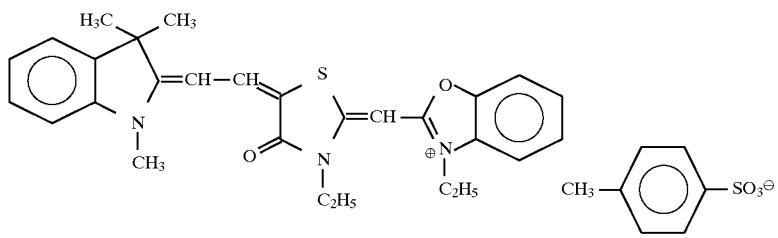 |
| 206 | 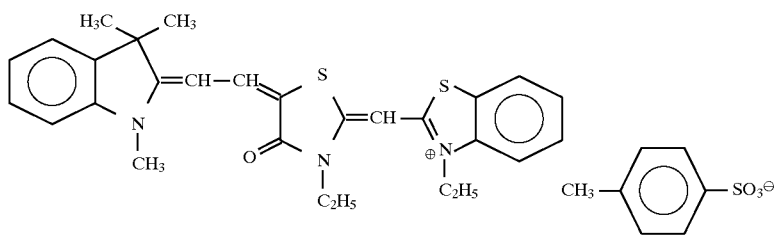 |
| 207 | 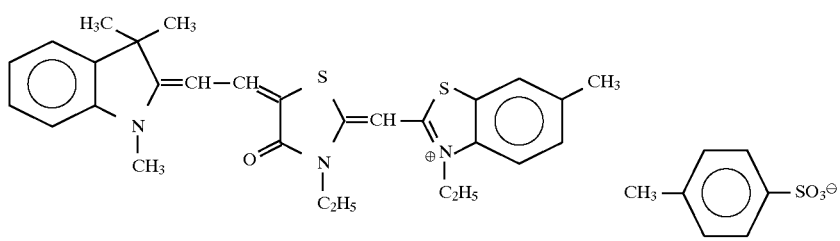 |
| 208 | 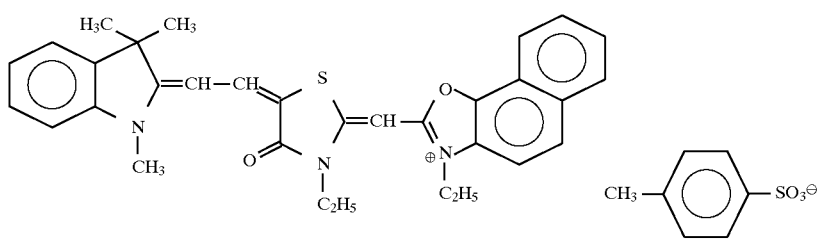 |
| 209 | 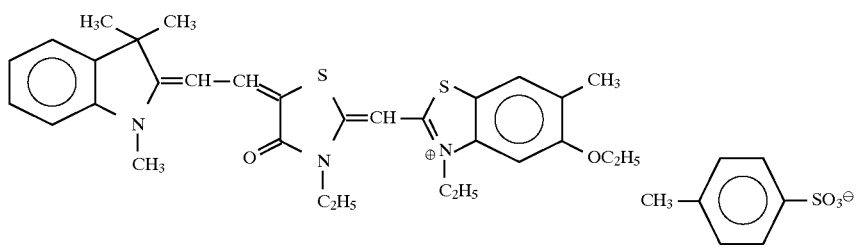 |

| Compound No. | Structure |
|---|---|
| 210 | 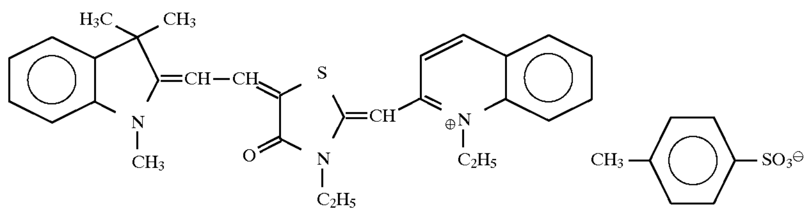 |
| 211 | 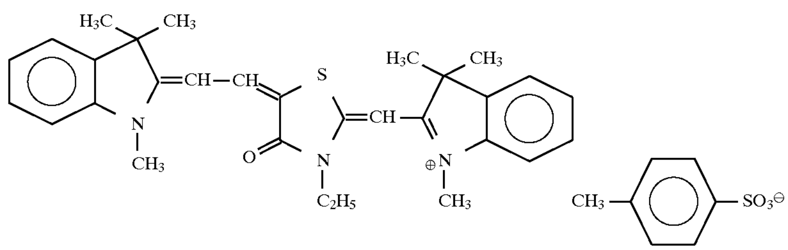 |
| 212 | 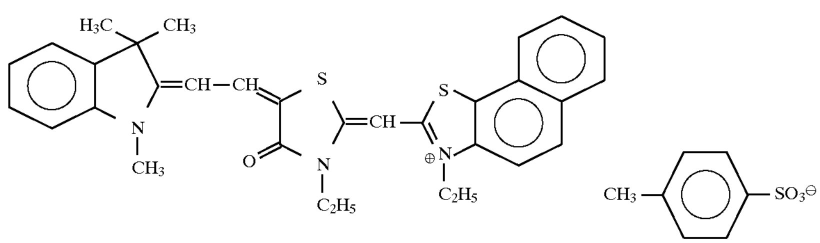 |
| 213 | 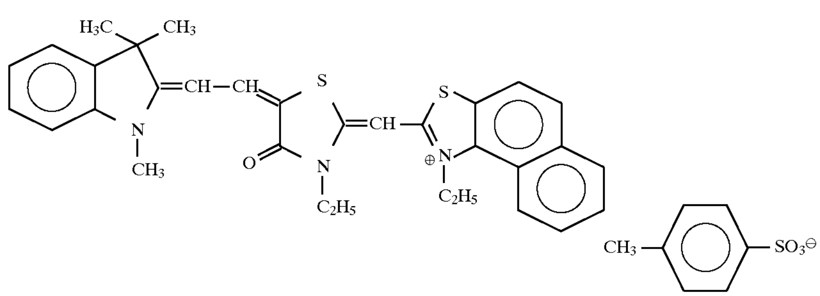 |
| 214 | 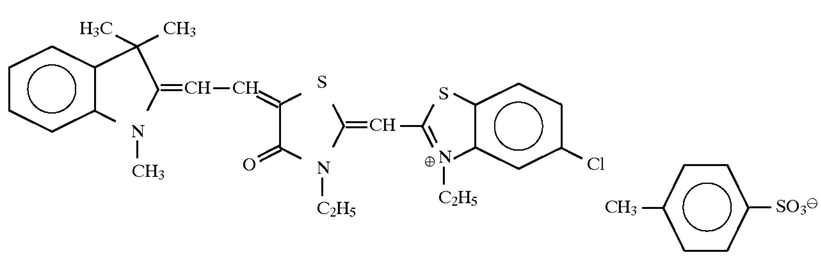 |
| 215 | 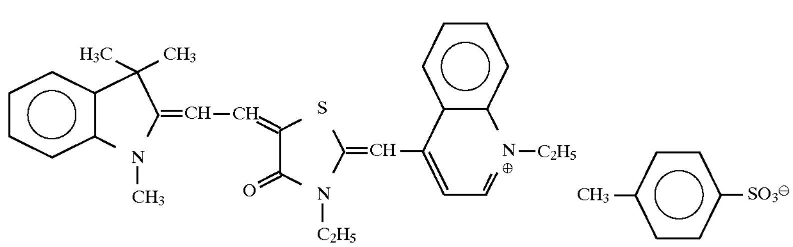 |
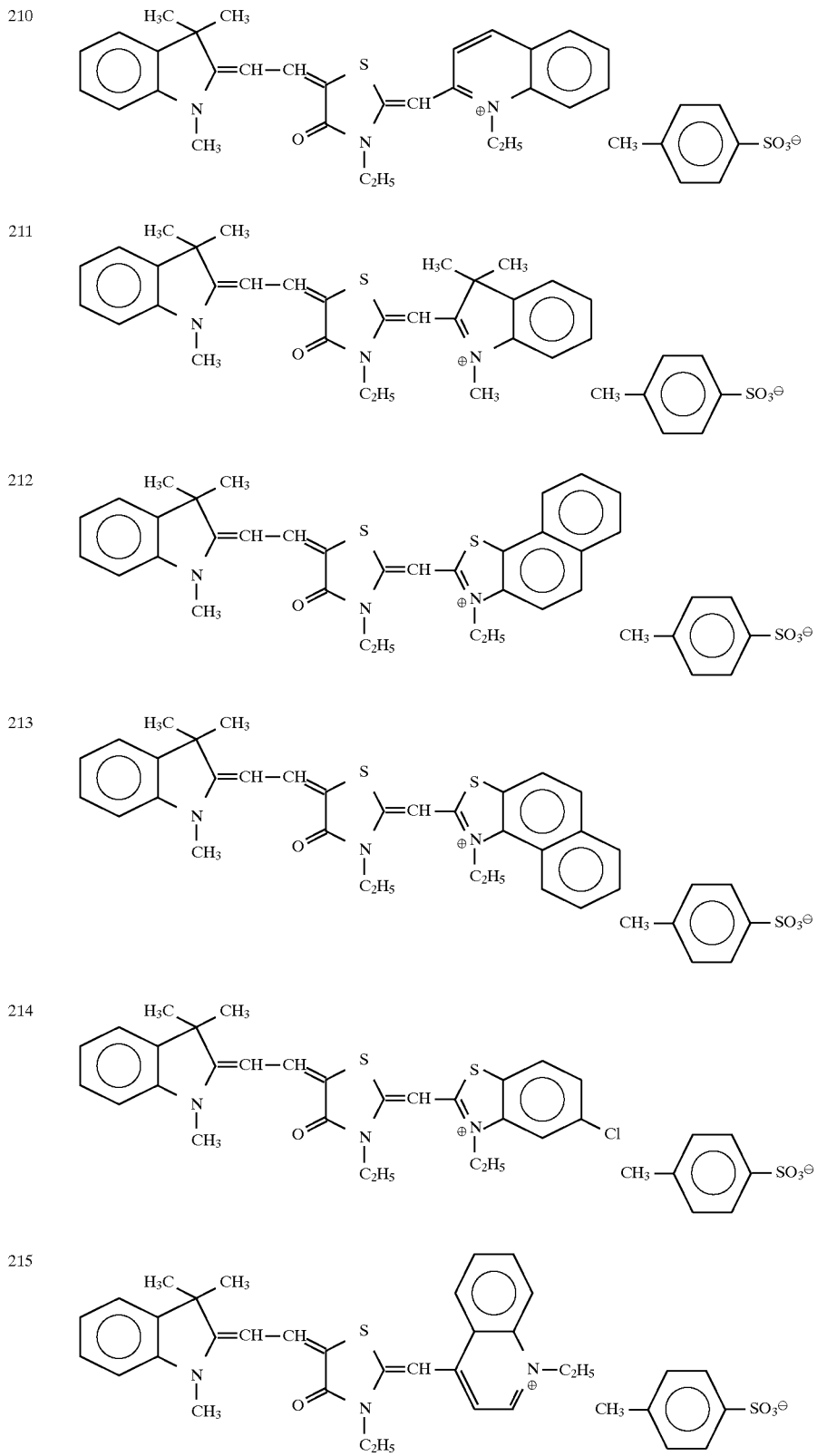

| Compound No. | Structure |
|---|---|
| 216 | 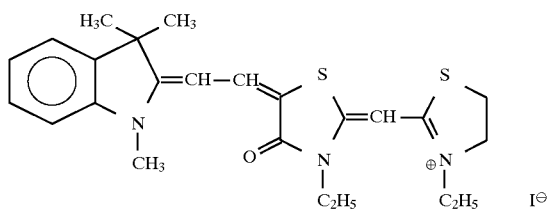 |
| 217 | 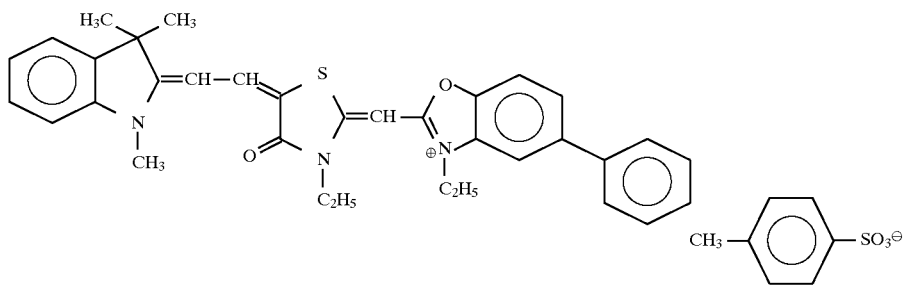 |
| 218 | 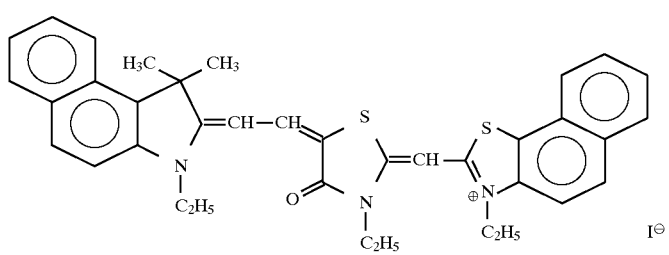 |
| 219 | 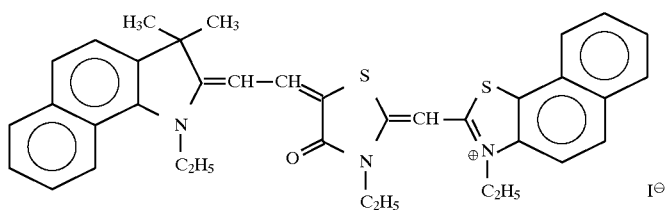 |
| 220 | 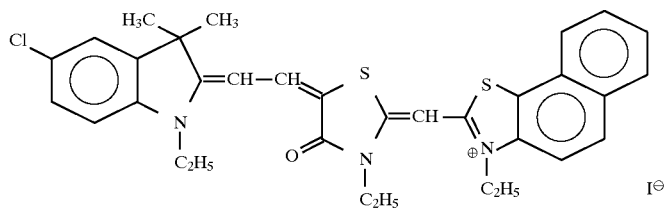 |
| 221 | 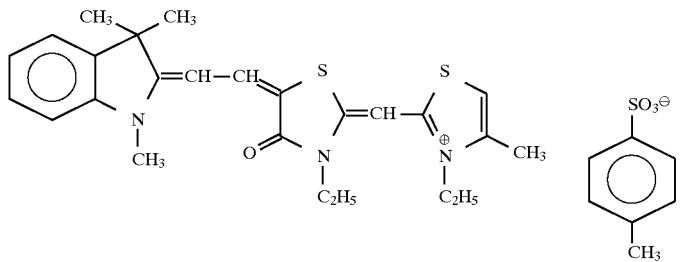 |

-continued

| Compound No. | Structure |
|---|---|
| 222 | 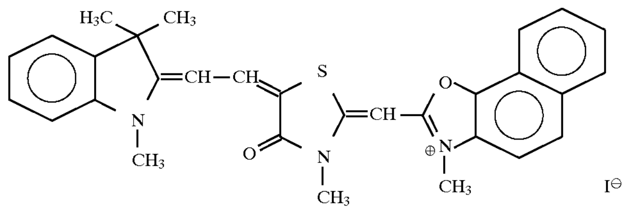 |
| 223 | 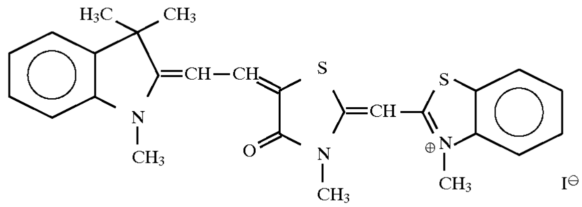 |
| 224 | 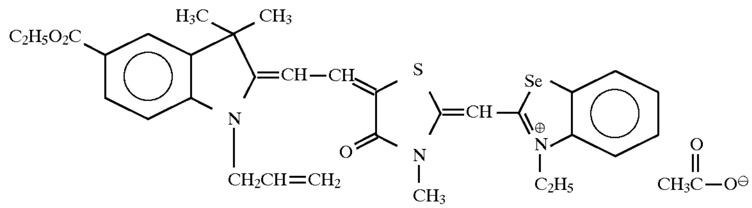 |
| 225 | 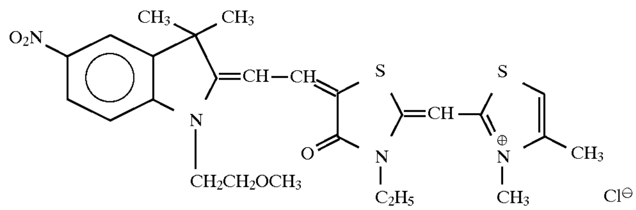 |
| 226 | 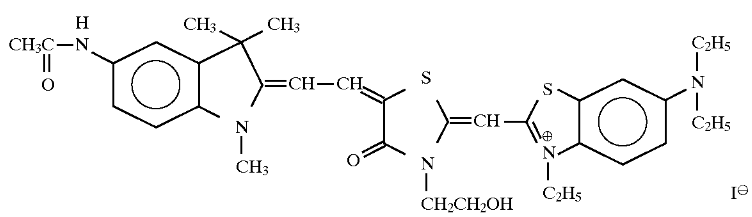 |
| 227 | 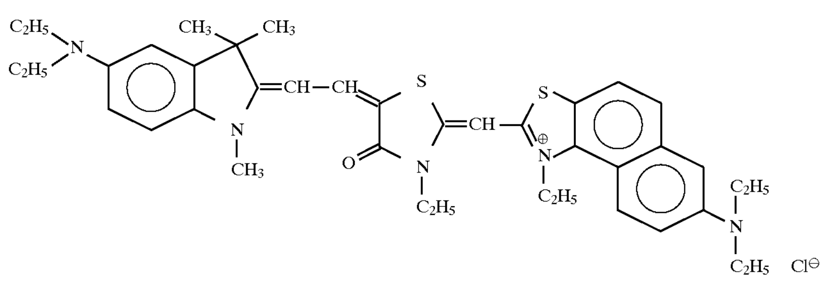 |
| 228 | 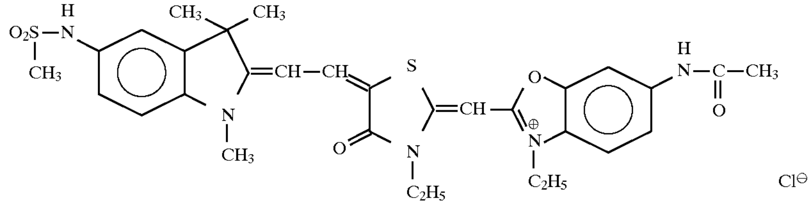 |

| Compound No. | Structure |
|---|---|
| 229 | 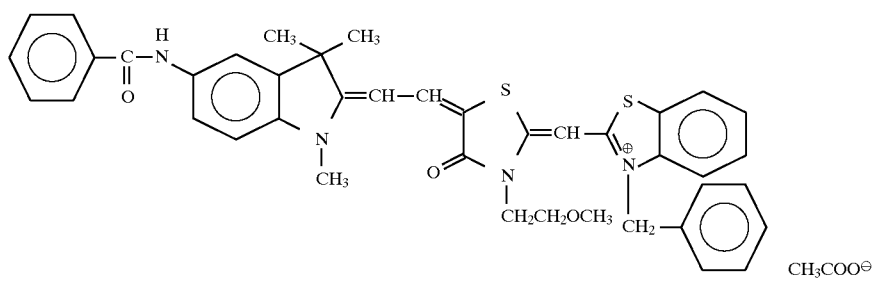 |
| 230 | 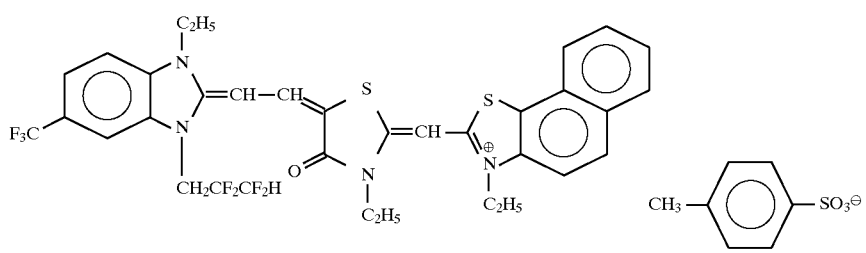 |
| 231 | 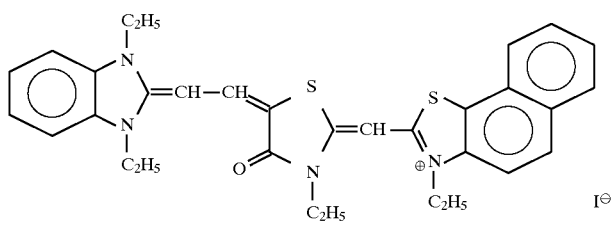 |
| 232 | 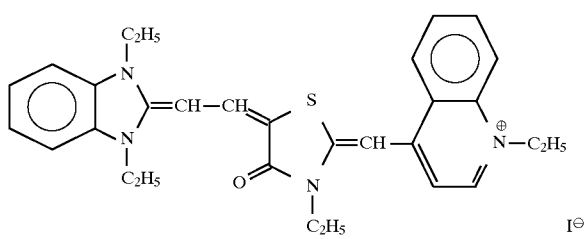 |
| 233 | 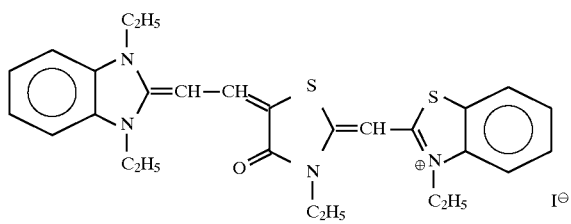 |
| 234 | 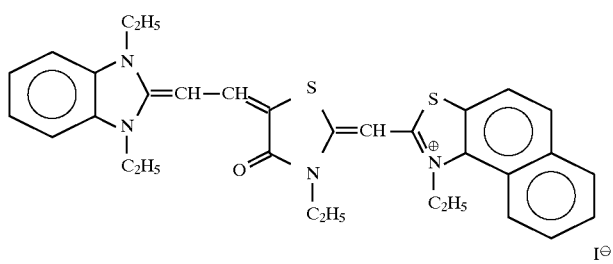 |

-continued
| Compound No. | Structure |
|---|---|
| 235 | 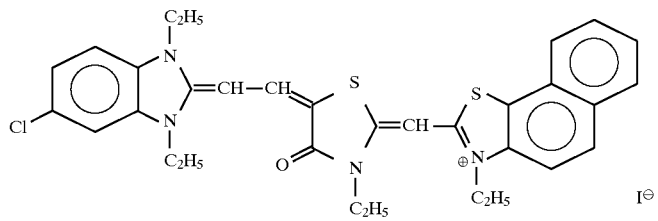 |
| 236 | 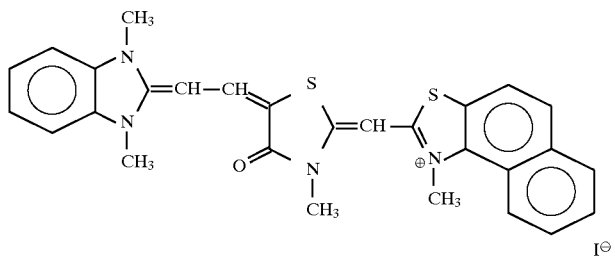 |
| 237 | 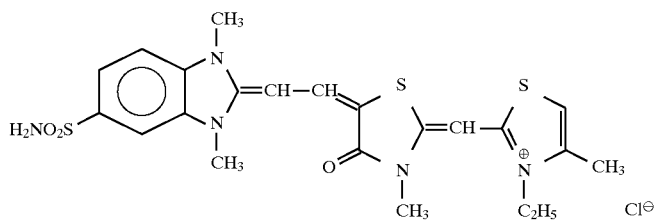 |
| 238 | 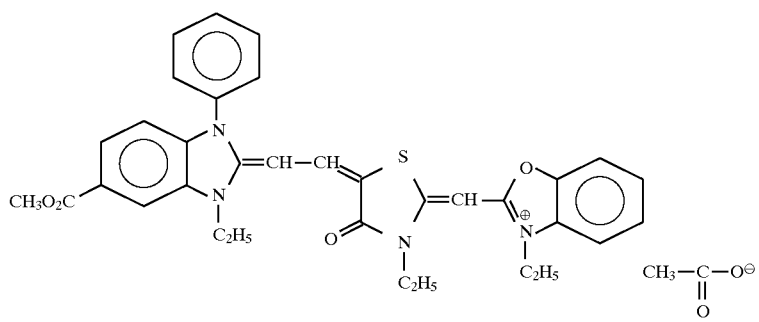 |
| 239 | 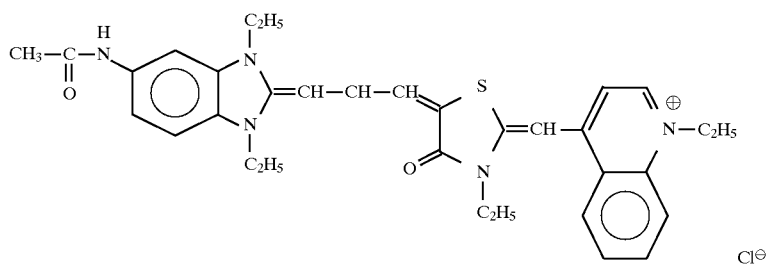 |
| 240 | 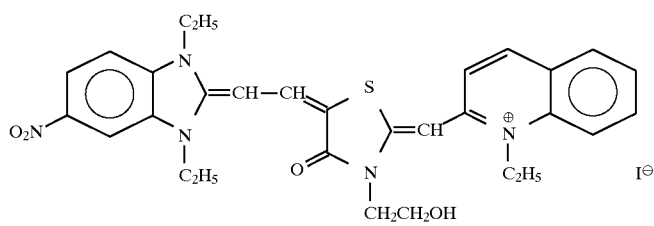 |

| Compound No. | Structure |
|---|---|
| 241 | 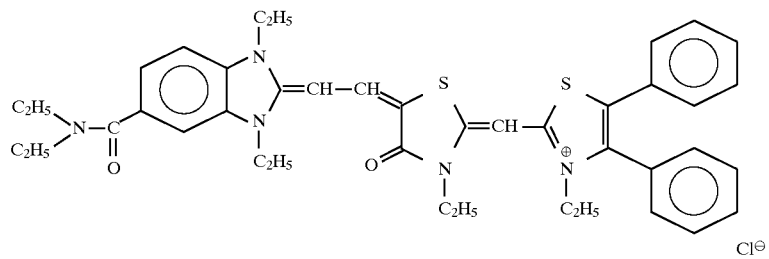 |
| 242 | 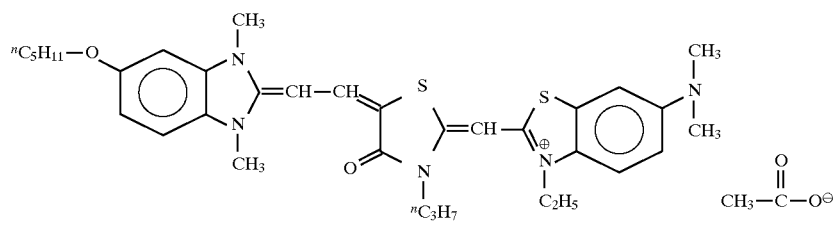 |
| 243 | 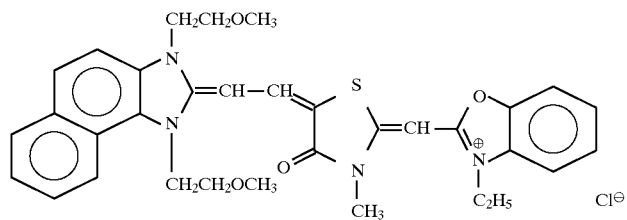 |
| 244 | 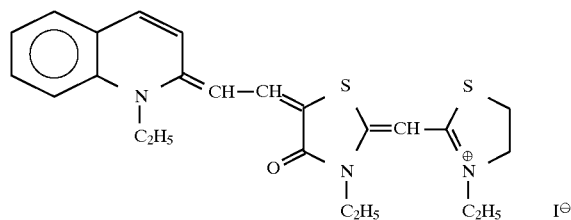 |
| 245 | 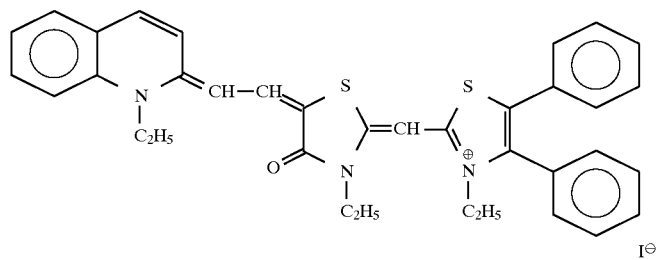 |
| 246 | 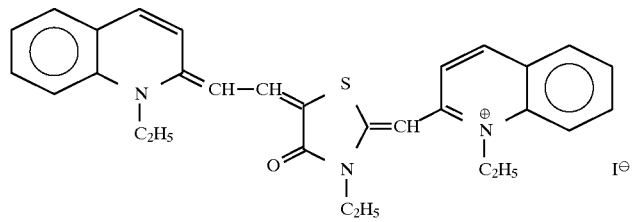 |

| Compound No. | Structure |
|---|---|
| 247 | 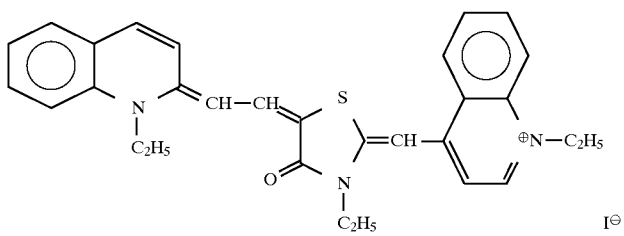 |
| 248 | 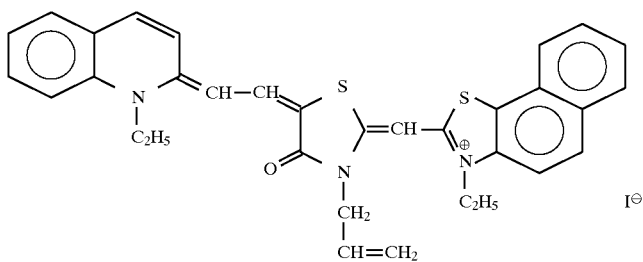 |
| 249 | 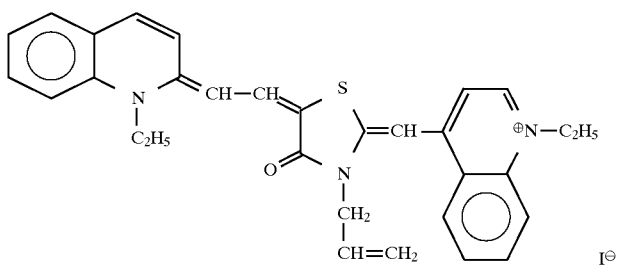 |
| 250 | 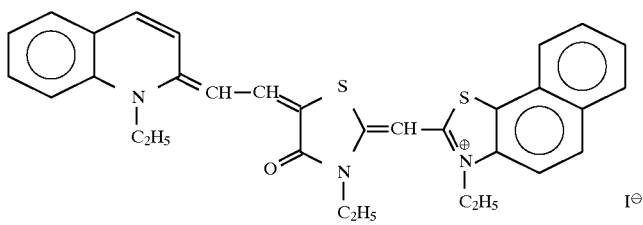 |
| 251 | 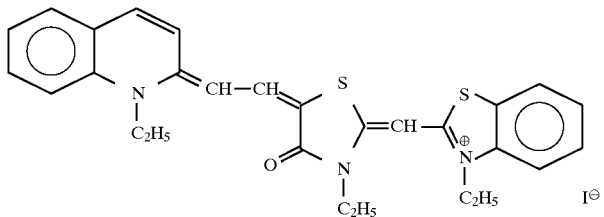 |
| 252 | 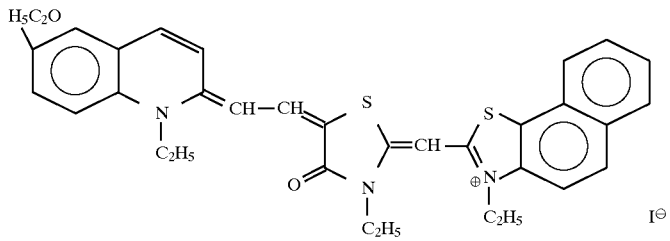 |

| Compound No. | Structure |
|---|---|
| 253 | 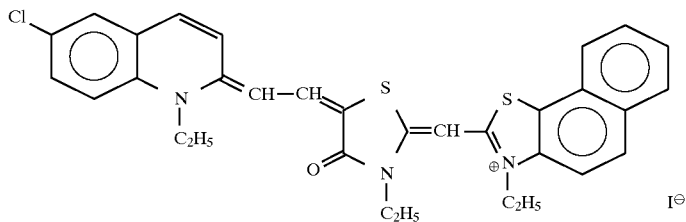 |
| 254 | 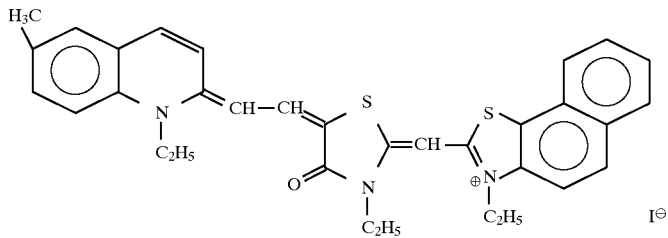 |
| 255 | 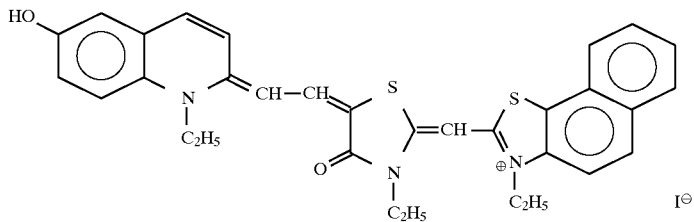 |
| 256 | 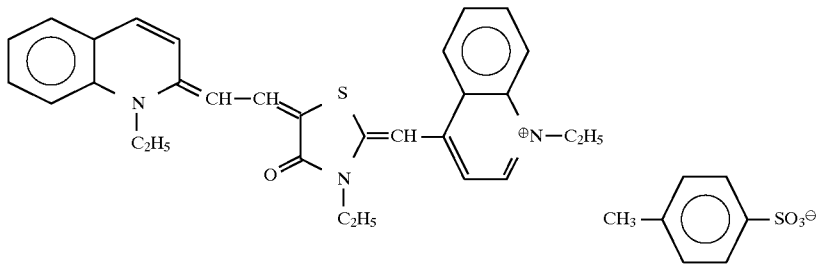 |
| 257 | 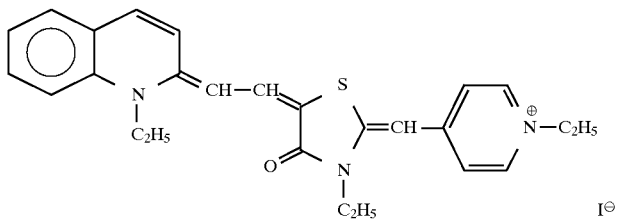 |
| 258 | 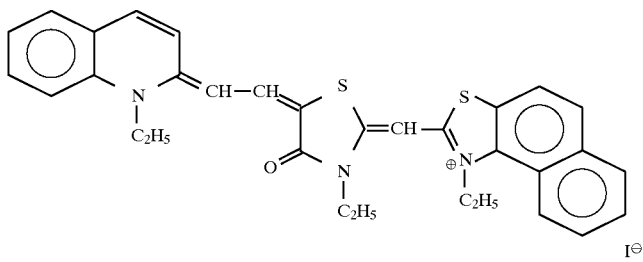 |

| Compound No. | Structure |
|---|---|
| 259 | 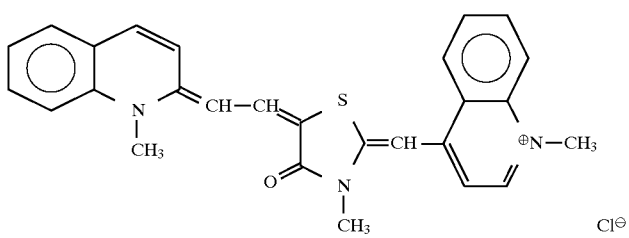 |
| 260 | 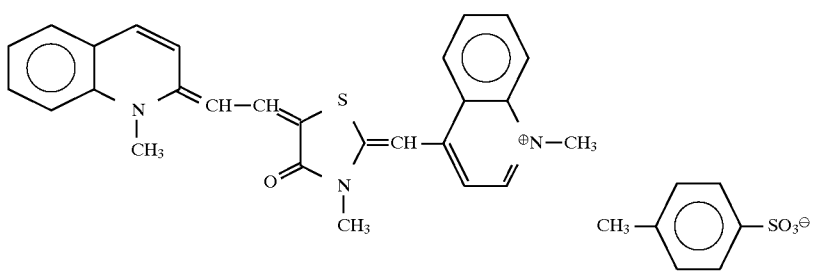 |
| 261 | 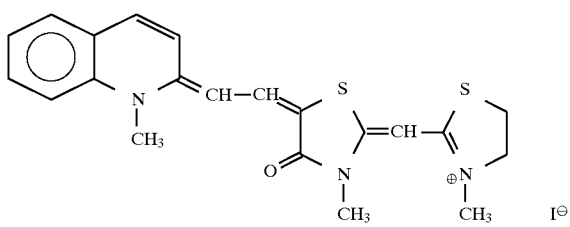 |
| 262 | 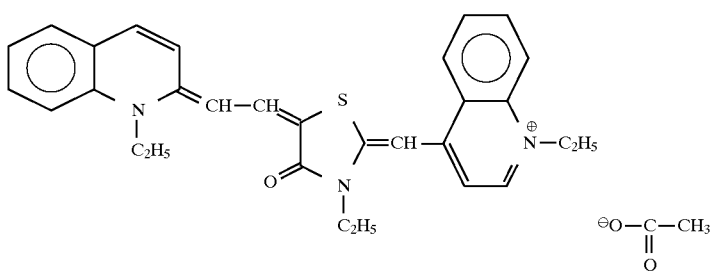 |
| 263 | 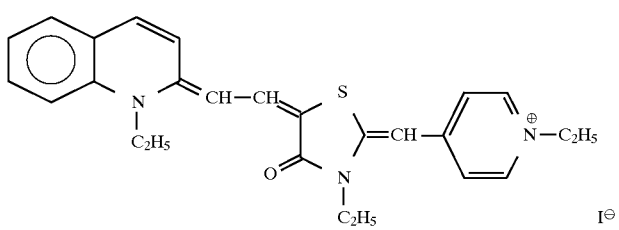 |
| 264 | 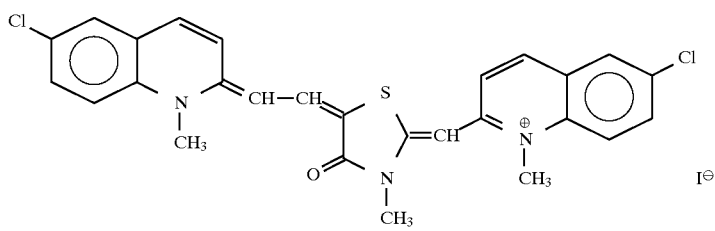 |

| Compound No. | Structure |
|---|---|
| 265 | 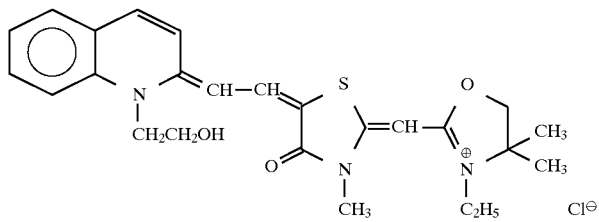 |
| 266 | 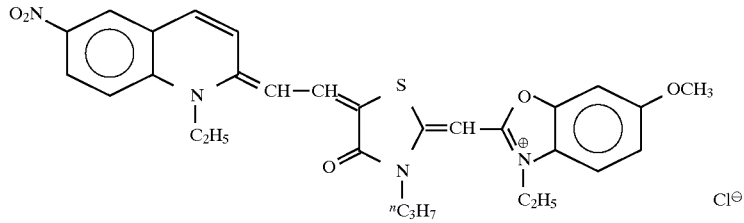 |
| 267 | 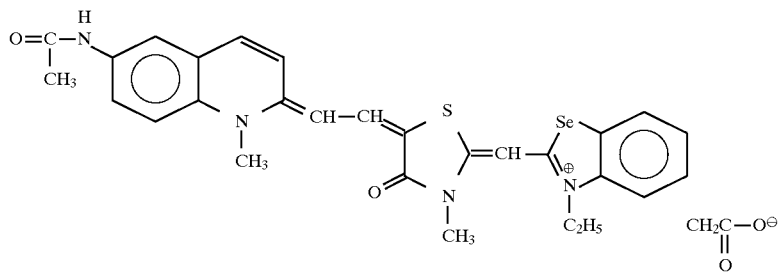 |
| 268 | 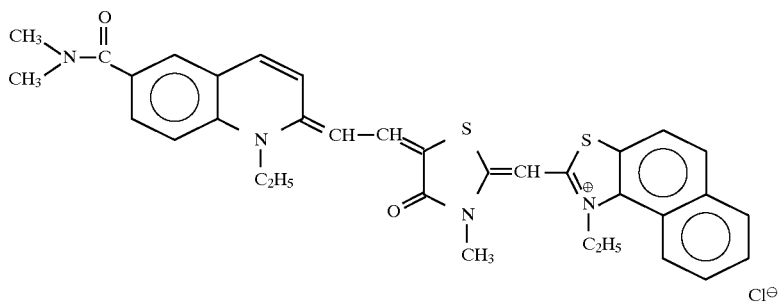 |
| 269 | 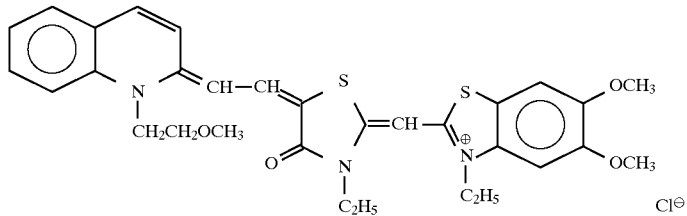 |
| 270 | 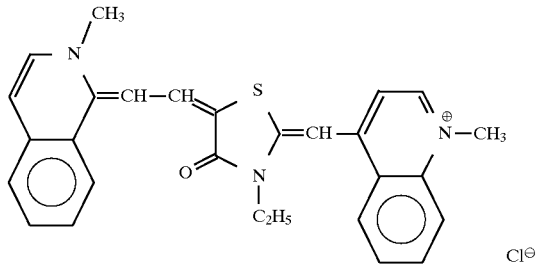 |

| Compound No. | Structure |
|---|---|
| 271 | 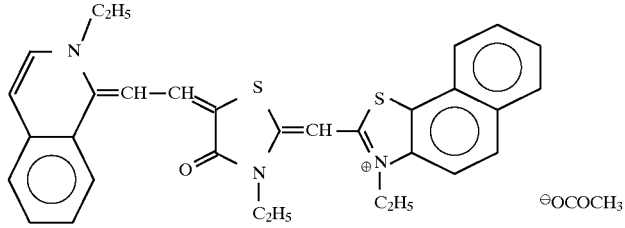 |
| 272 | 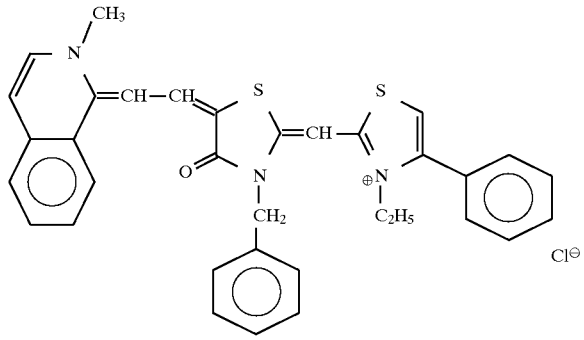 |
| 273 | 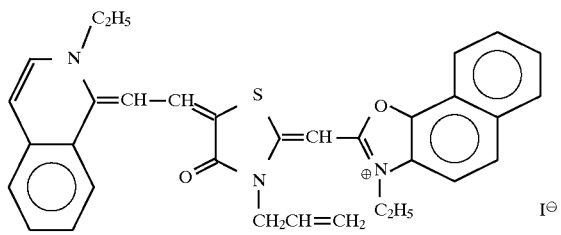 |
| 274 | 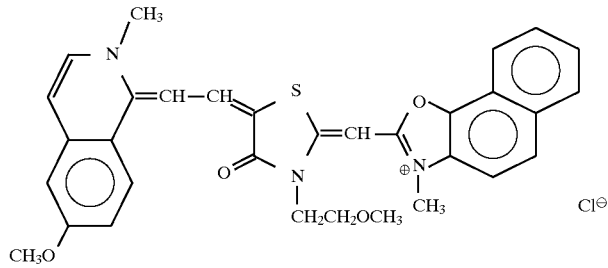 |
| 275 | 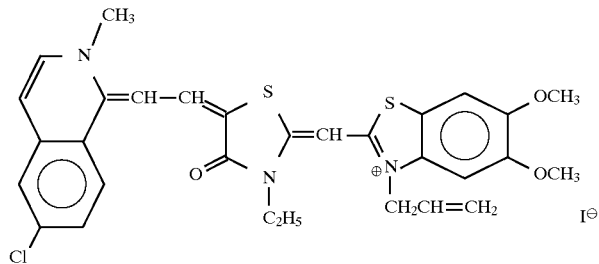 |
| 276 | 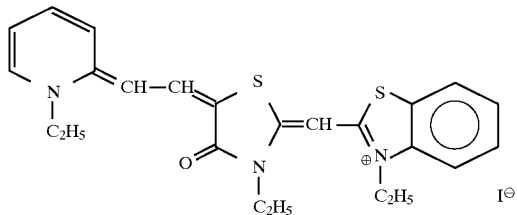 |

| Compound No. | Structure |
|---|---|
| 277 | 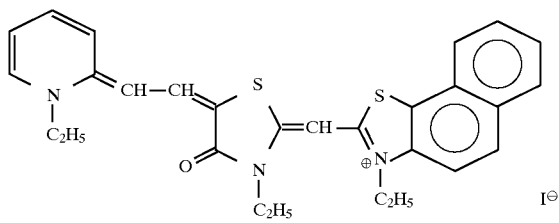 |
| 278 | 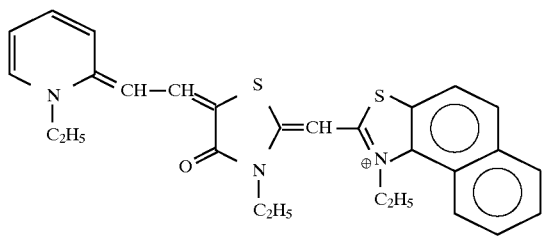 |
| 279 | 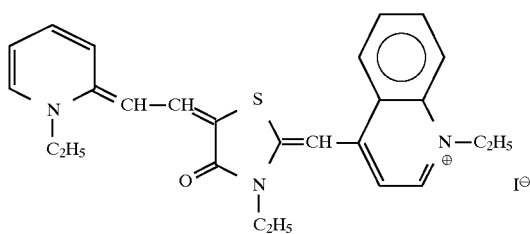 |
| 280 | 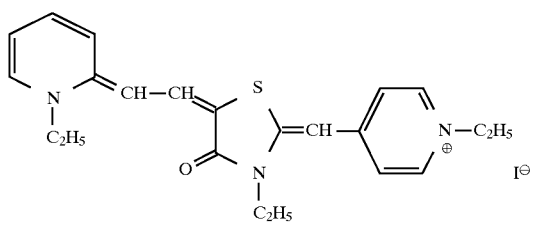 |
| 281 | 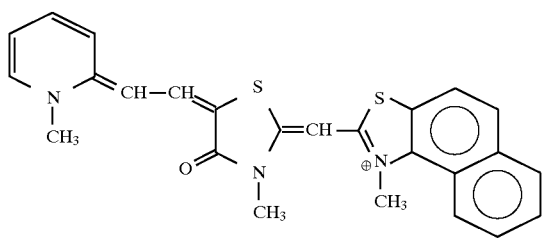 |
| 282 | 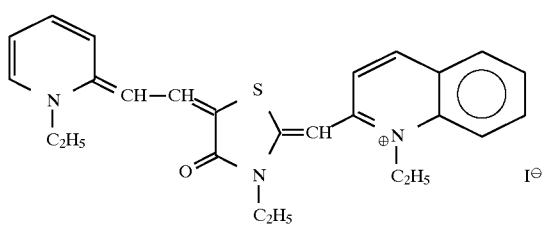 |

-continued
| Compound No. | Structure |
|---|---|
| 283 | 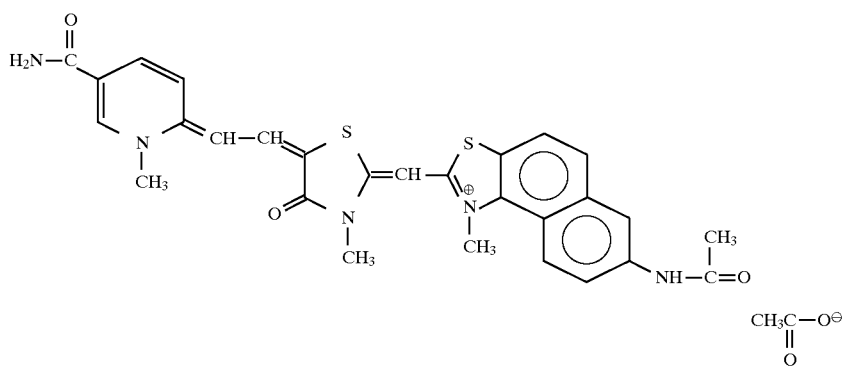 |
| 284 | 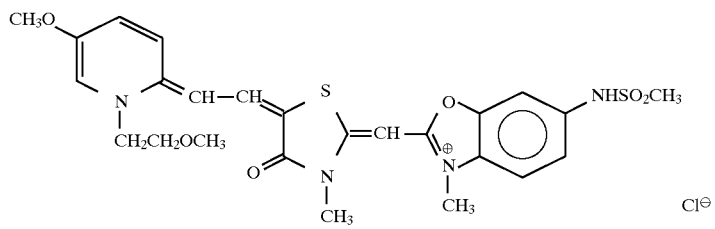 |
| 285 | 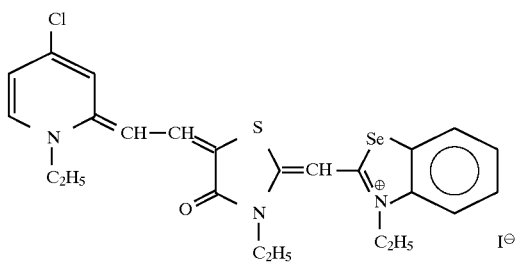 |
| 286 | 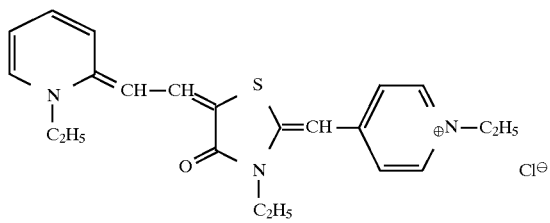 |
| 287 | 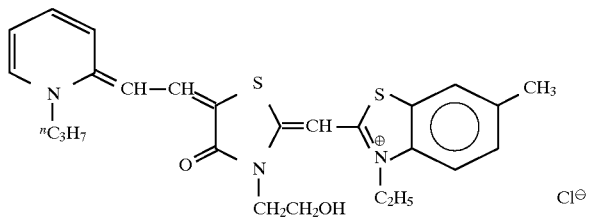 |
| 288 | 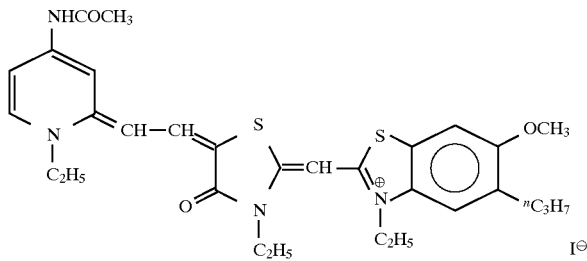 |

-continued

| Compound No. | Structure |
|---|---|
| 289 | (structure image) |
| 290 | (structure image) |
| 291 | (structure image) |
| 292 | (structure image) |
| 293 | (structure image) |
| 294 | (structure image) |
| 295 | (structure image) |

| Compound No. | Structure |
|---|---|
| 296 | 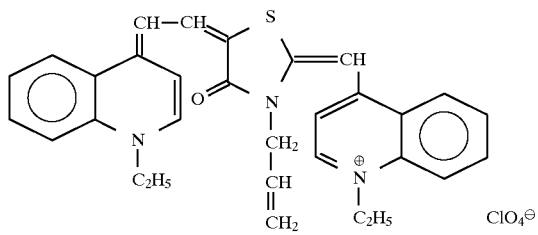 |
| 297 | 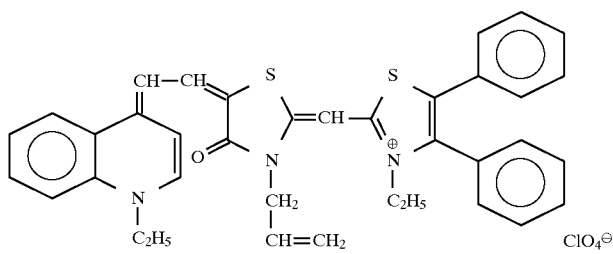 |
| 298 | 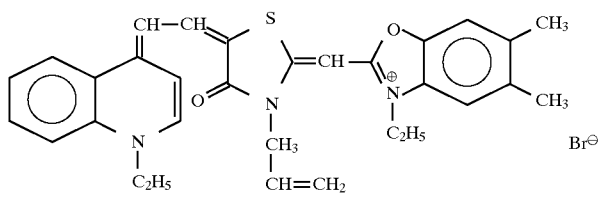 |
| 299 | 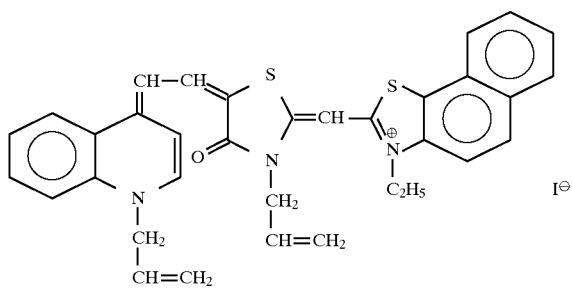 |
| 300 | 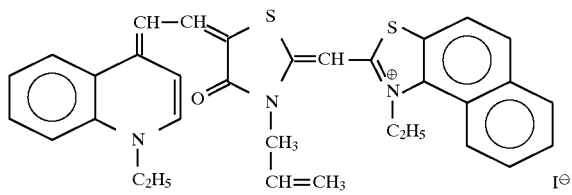 |
| 301 | 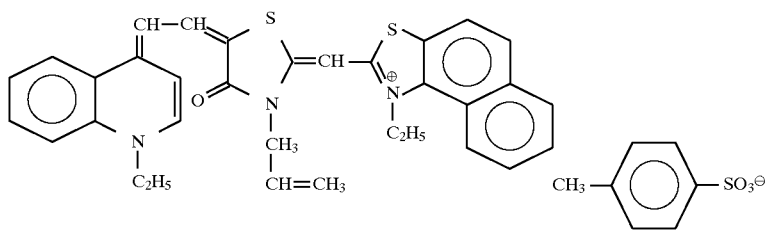 |

| Compound No. | Structure |
|---|---|
| 302 | 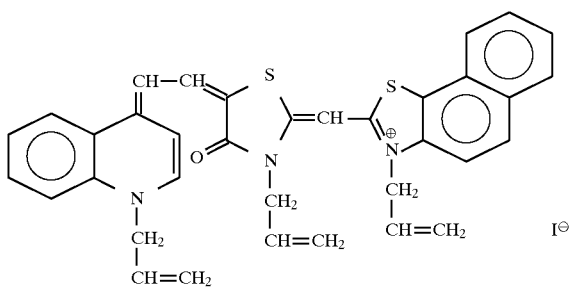 |
| 303 | 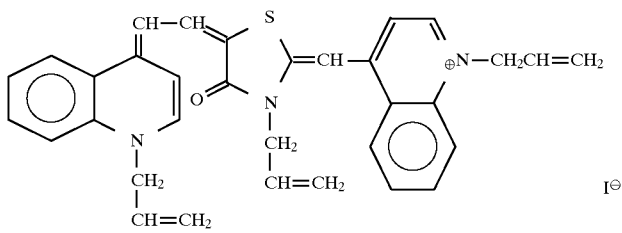 |
| 304 | 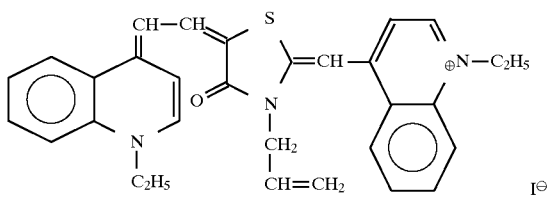 |
| 305 | 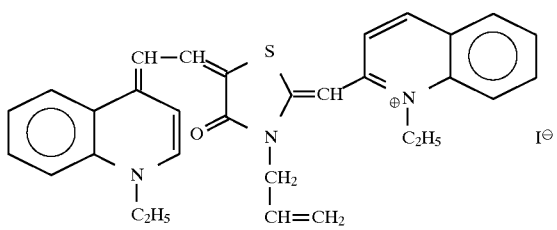 |
| 306 | 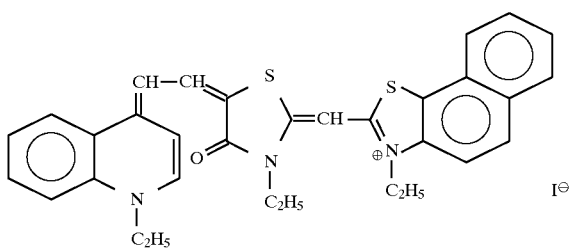 |
| 307 | 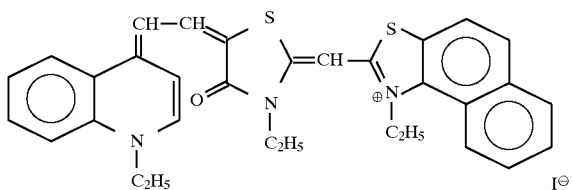 |

| Compound No. | Structure |
|---|---|
| 308 | 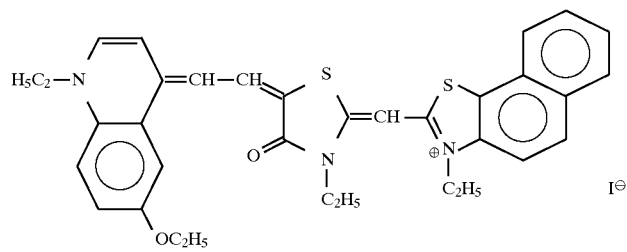 |
| 309 | 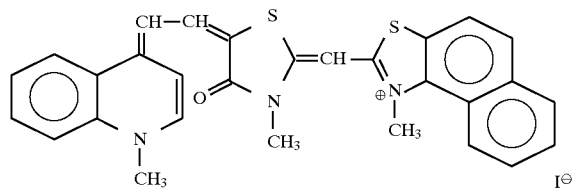 |
| 310 | 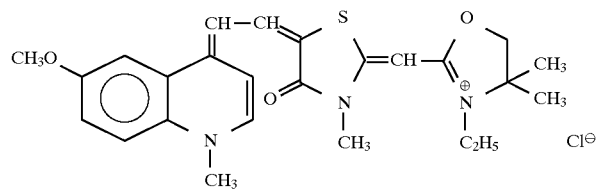 |
| 311 | 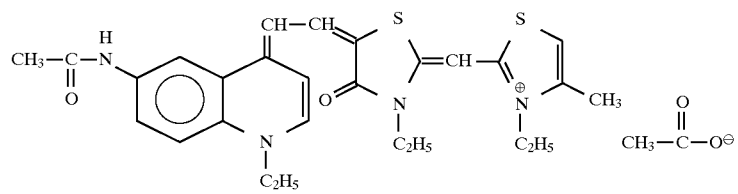 |
| 312 | 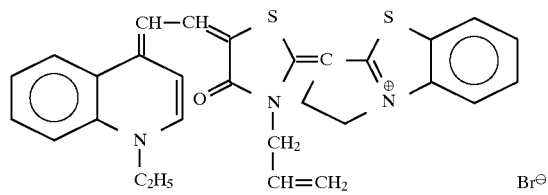 |
| 313 | 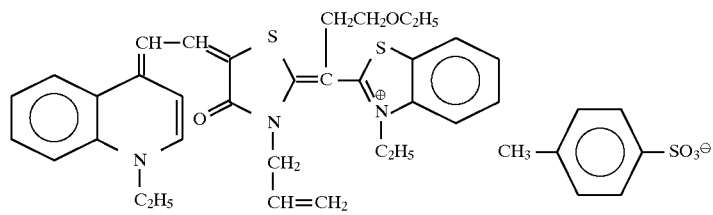 |
| 314 | 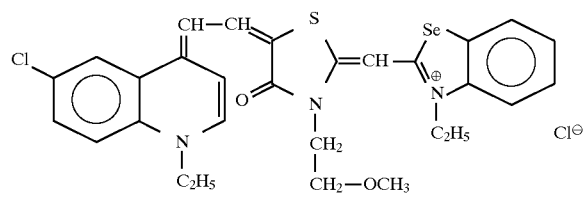 |

| Compound No. | Structure |
|---|---|
| 315 | 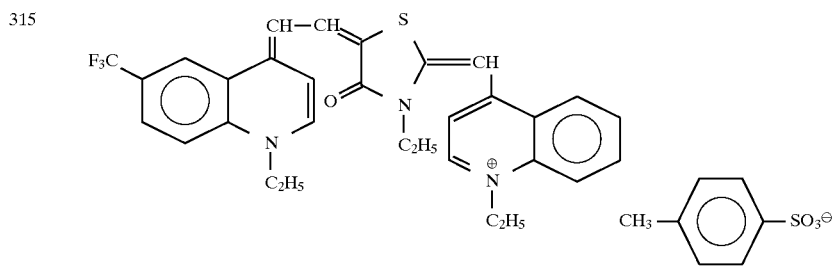 |
| 316 | 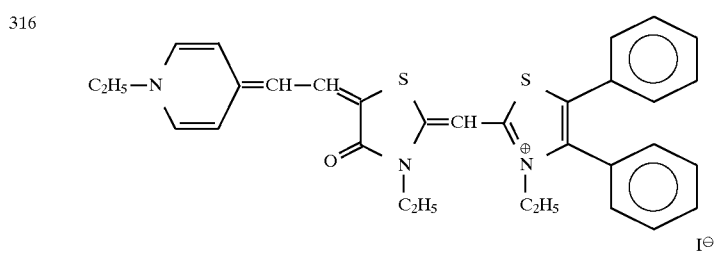 |
| 317 | 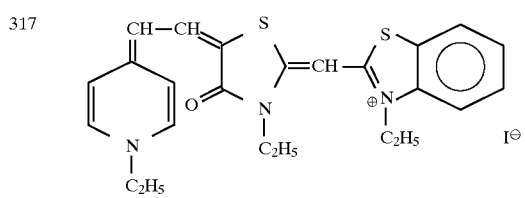 |
| 318 | 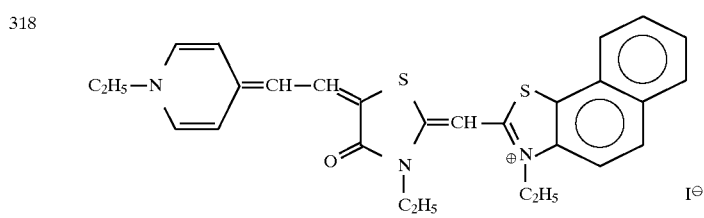 |
| 319 | 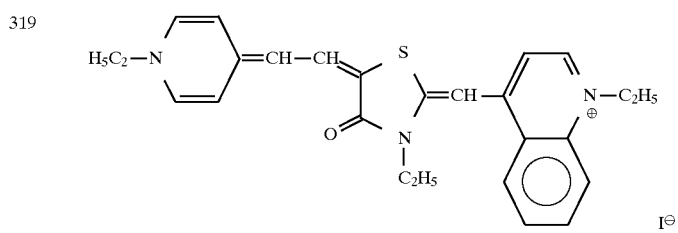 |
| 320 | 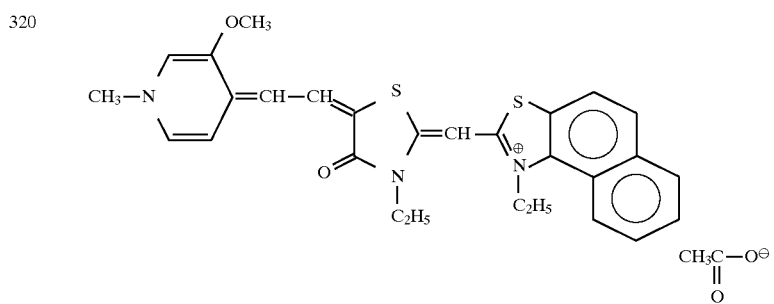 |

-continued
| Compound No. | Structure |
|---|---|
| 321 | 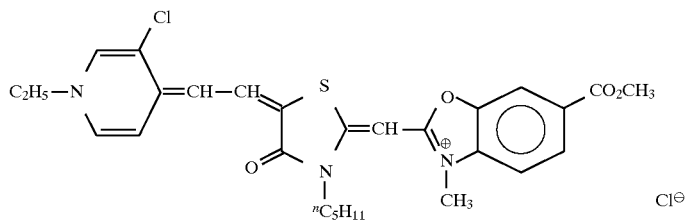 |
| 322 | 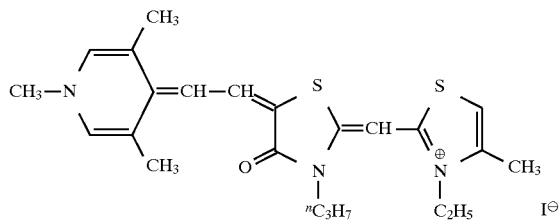 |
| 323 | 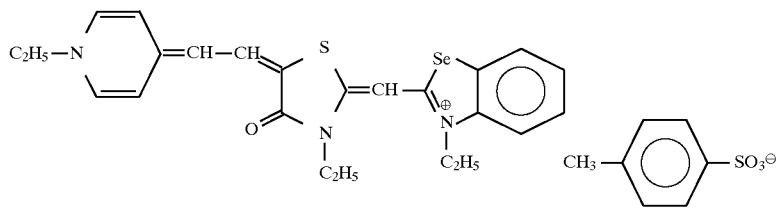 |
| 324 | 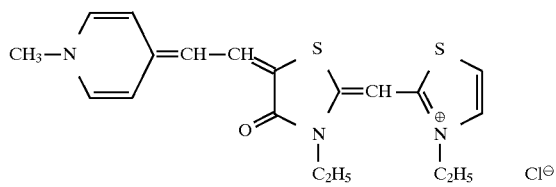 |
| 325 | 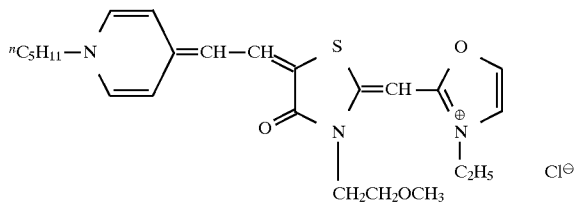 |
| 326 | 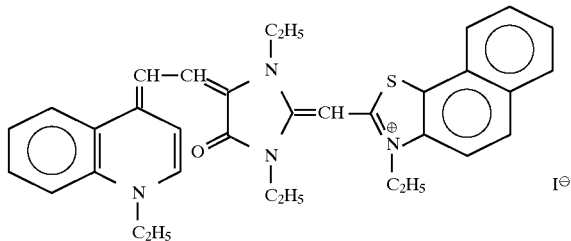 |
| 327 | 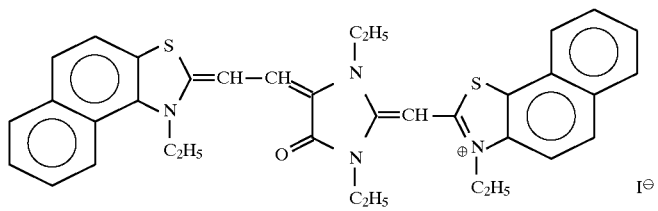 |

| Compound No. | Structure |
|---|---|
| 328 | 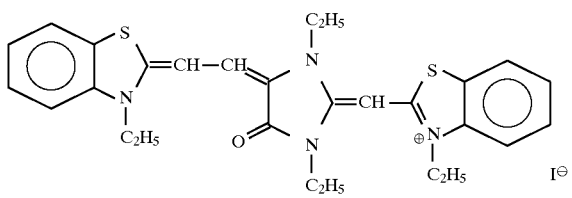 |
| 329 | 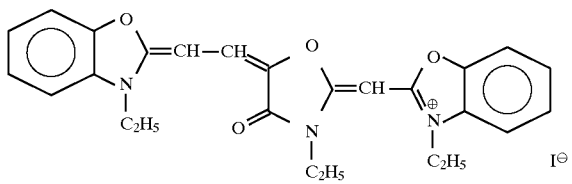 |
| 330 | 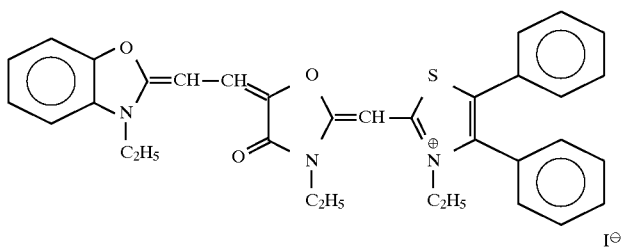 |
| 331 | 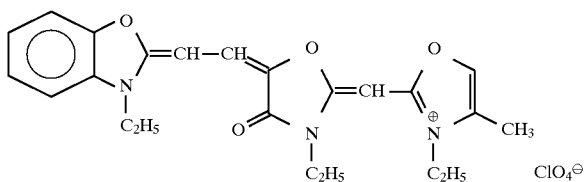 |
| 332 | 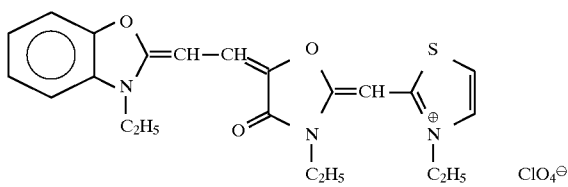 |
| 333 | 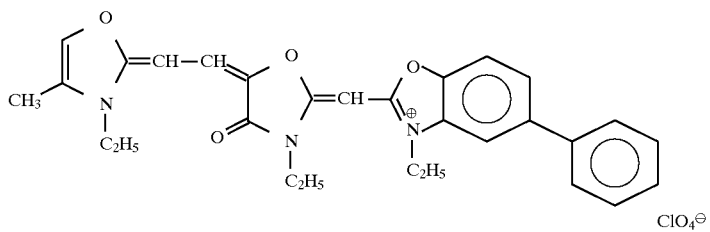 |
| 334 | 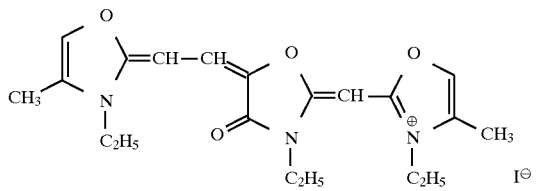 |

-continued
| Compound No. | Structure |
|---|---|
| 335 | 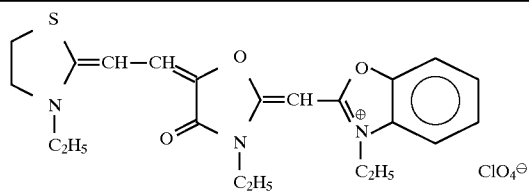 |
| 336 | 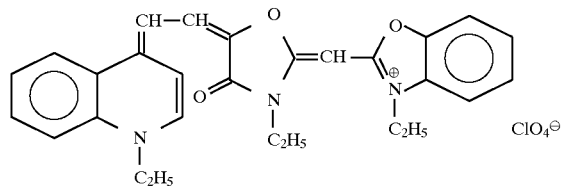 |
| 337 | 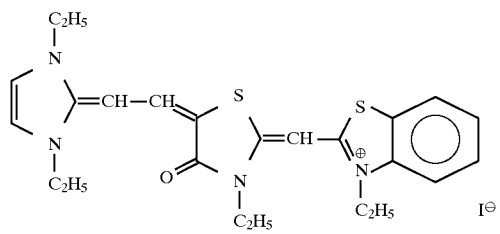 |
| 338 | 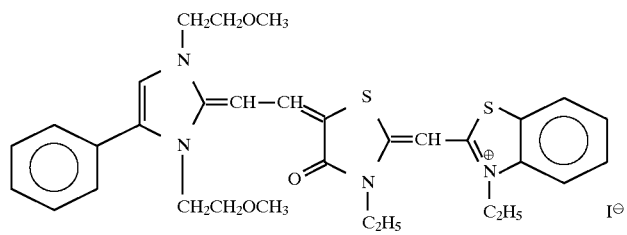 |
| 339 | 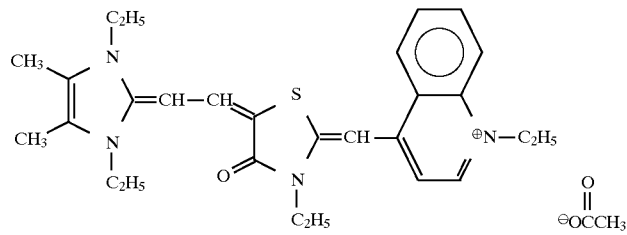 |
| 340 | 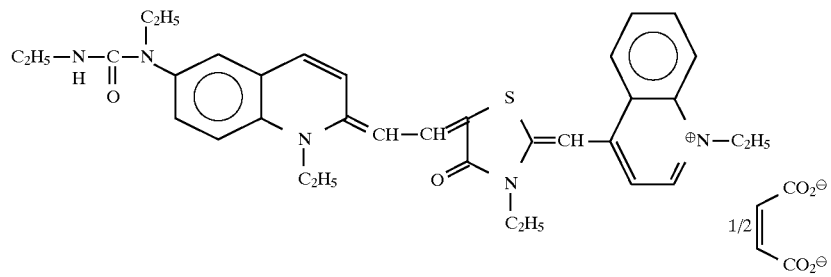 |
| 341 | 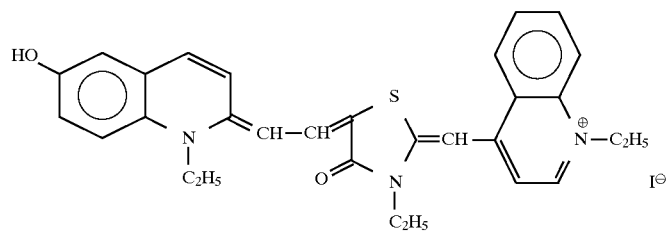 |

| Compound No. | Structure |
|---|---|
| 342 | 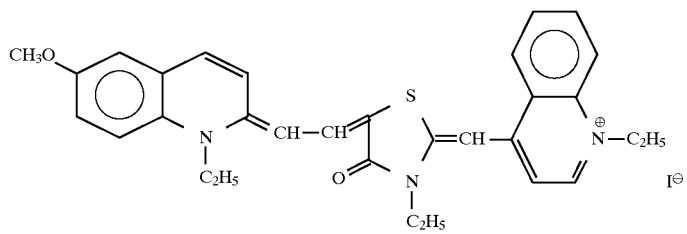 |
| 343 | 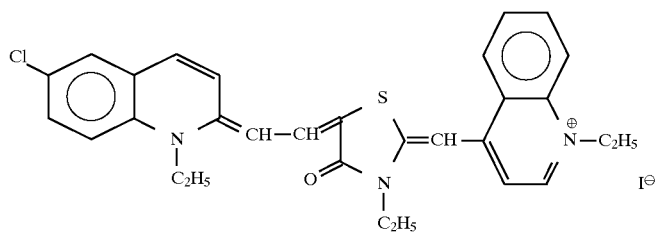 |
| 344 | 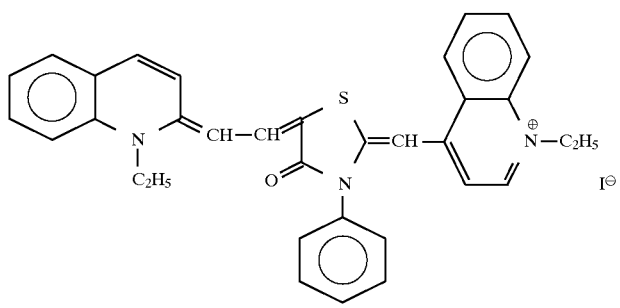 |
| 345 | 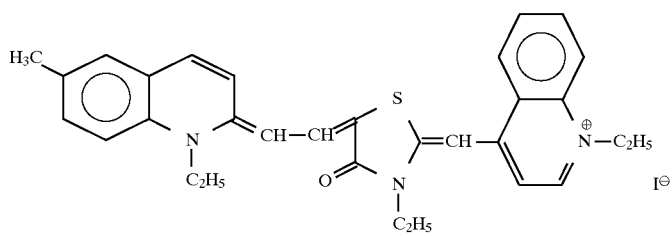 |
| 346 | 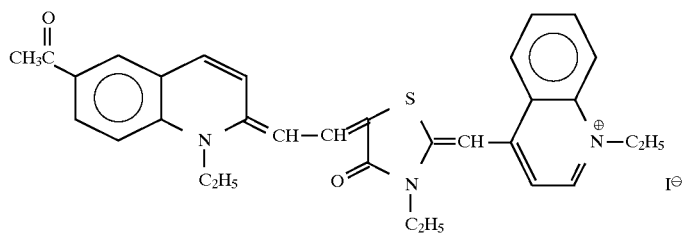 |
| 347 | 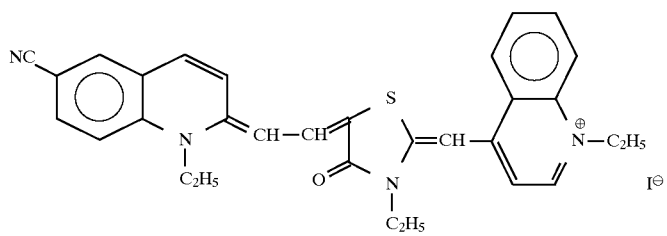 |

| Compound No. | Structure |
|---|---|
| 348 | 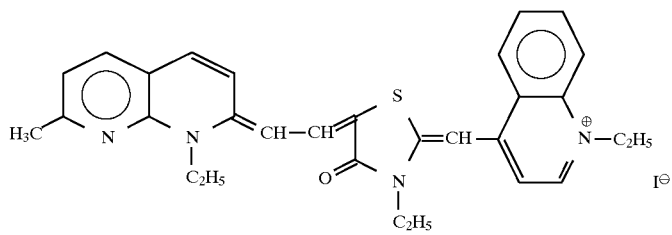 |
| 349 | 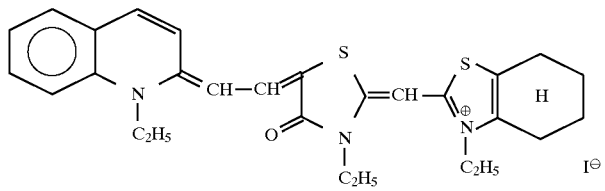 |
| 350 | 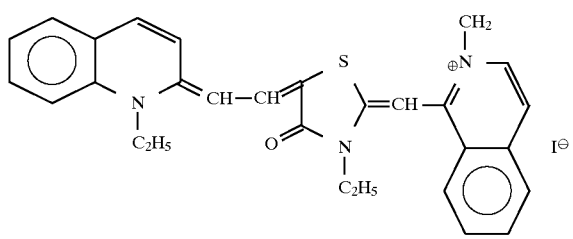 |
| 351 | 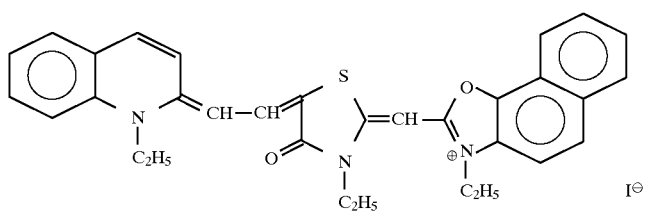 |
| 352 | 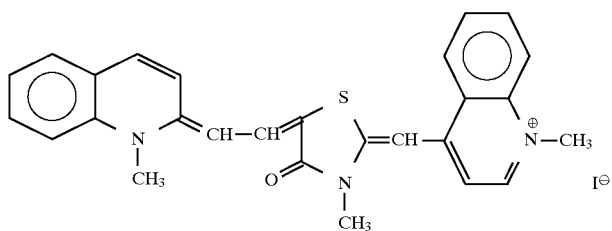 |
| 353 | 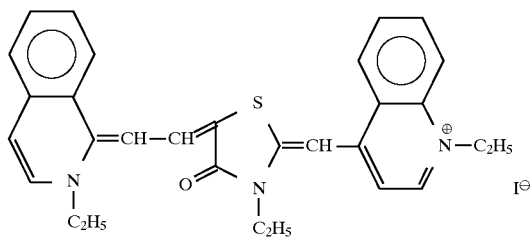 |
| 354 | 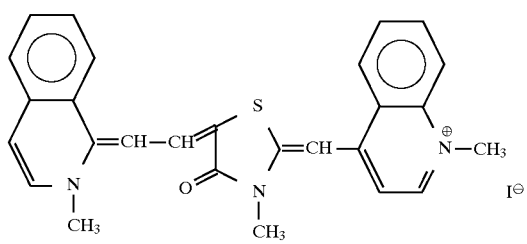 |

| Compound No. | Structure |
|---|---|
| 355 | 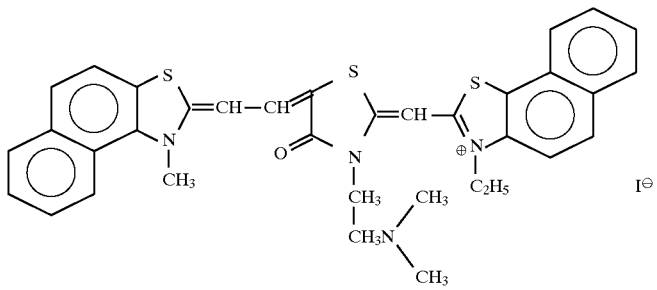 |
| 356 | 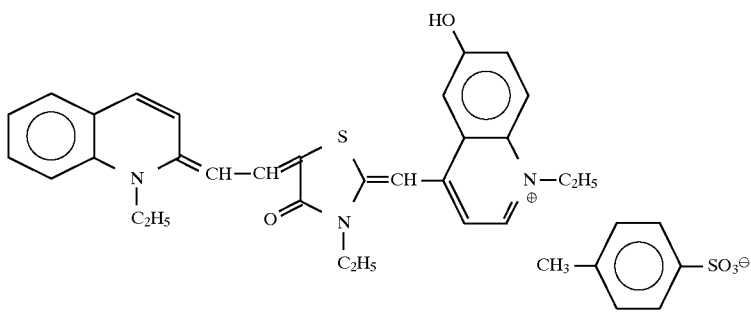 |
| 357 | 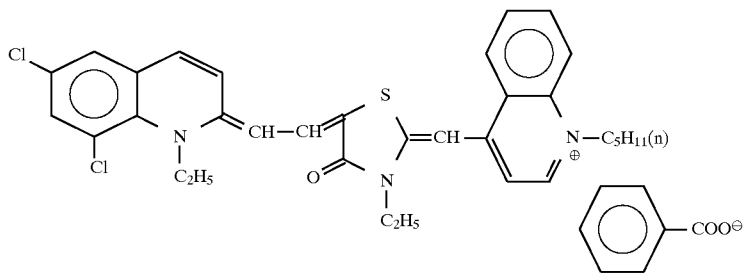 |
| 358 | 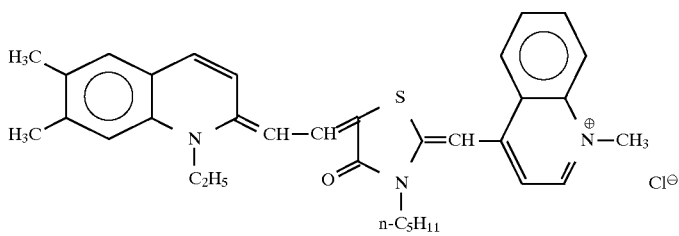 |
| 359 | 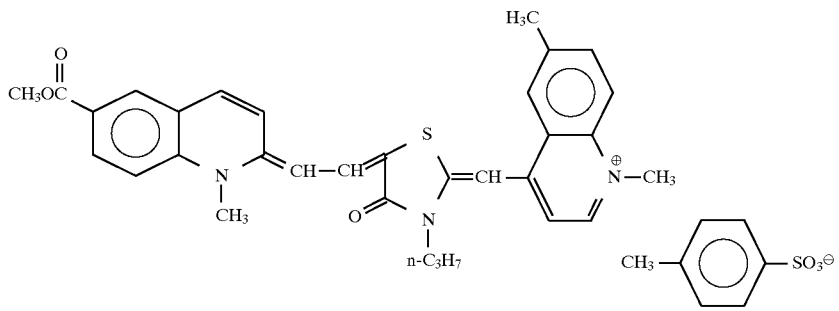 |

| Compound No. | Structure |
|---|---|
| 360 | 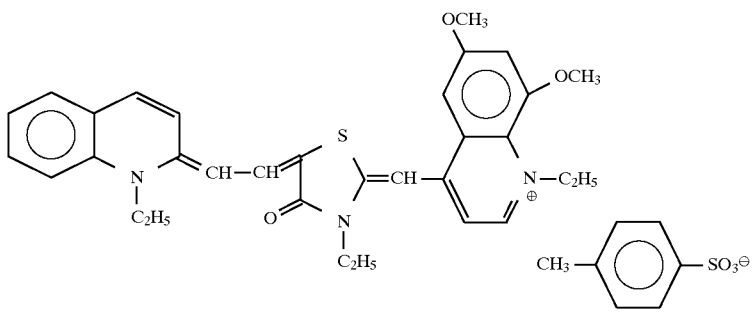 |
| 361 | 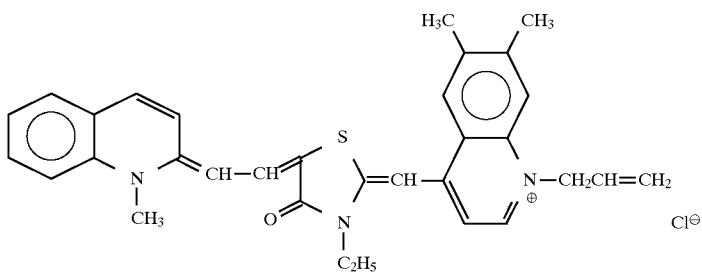 |
| 362 | 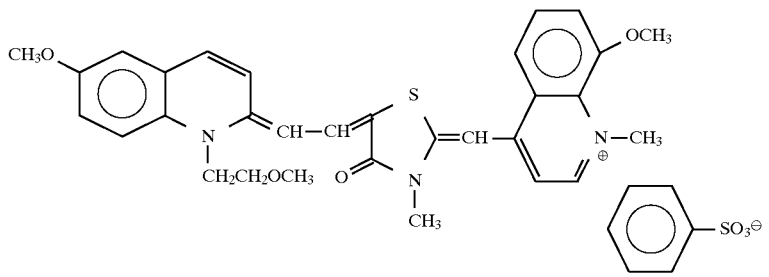 |
| 363 | 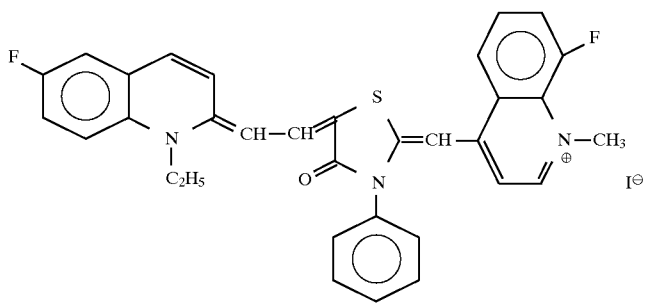 |
| 364 | 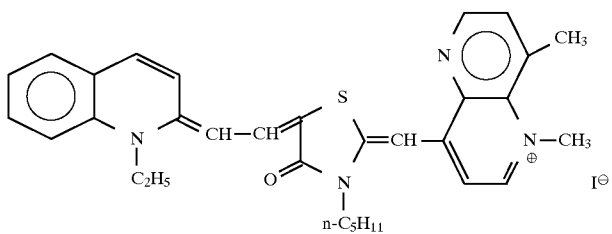 |

| Compound No. | Structure |
|---|---|
| 365 | 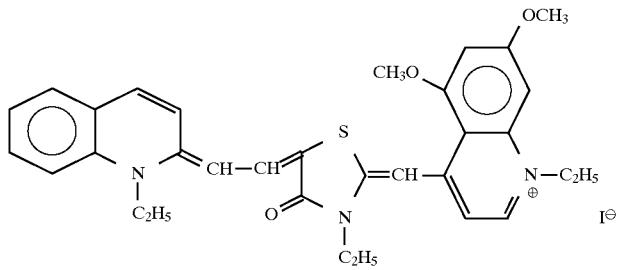 |
| 366 | 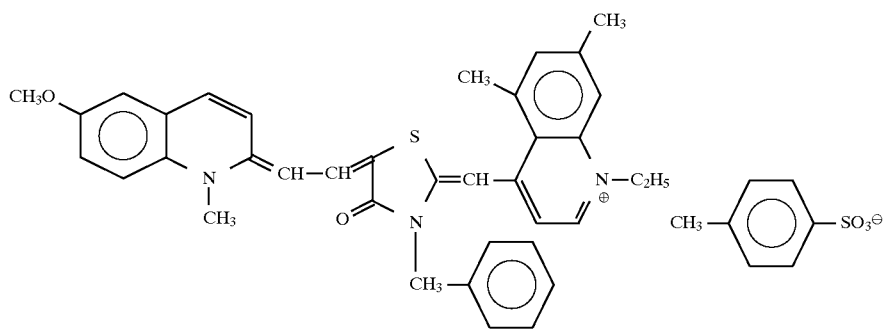 |
| 367 | 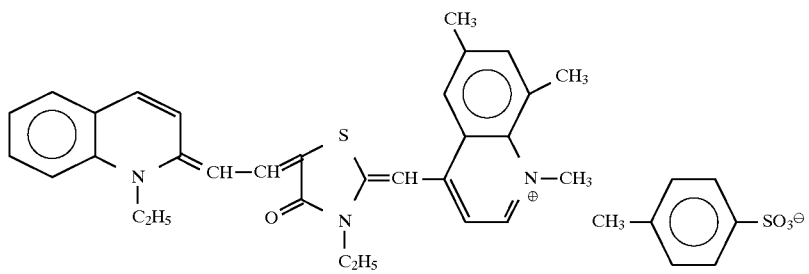 |
| 368 | 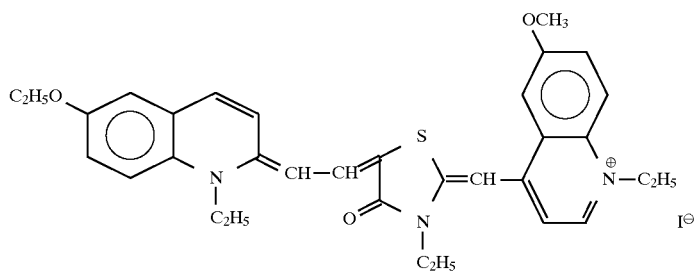 |
| 369 | 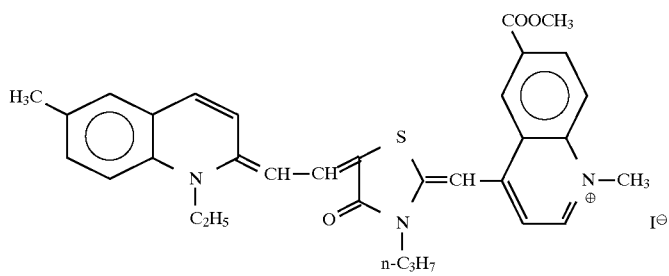 |

-continued
| Compound No. | Structure |
|---|---|
| 370 | 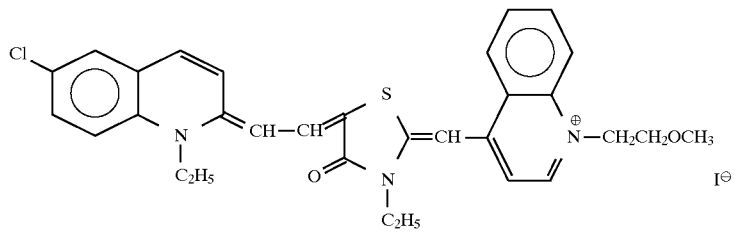 |
| 371 | 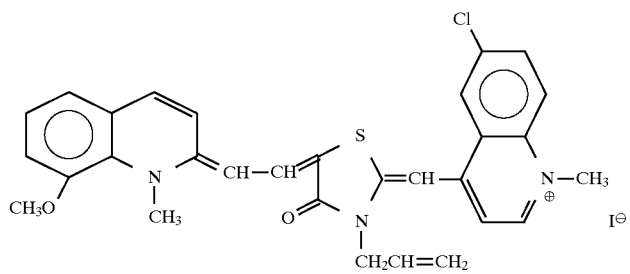 |
| 372 | 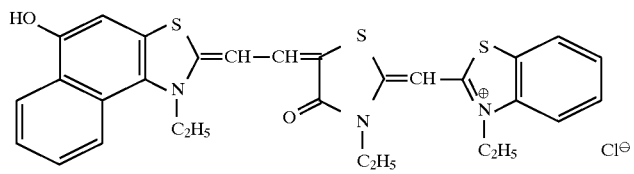 |
| 373 | 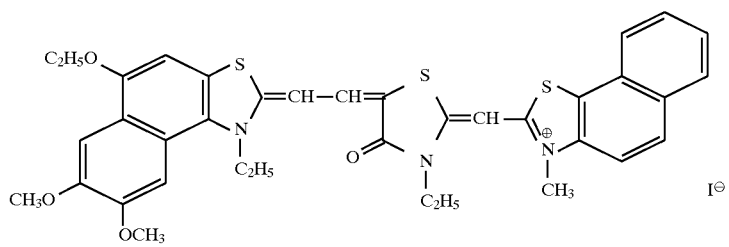 |
| 374 | 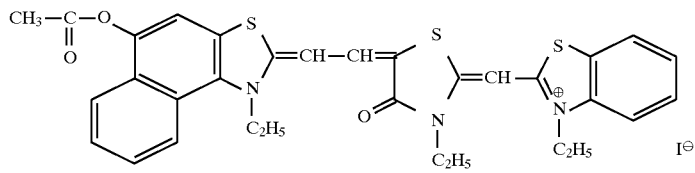 |
| 375 | 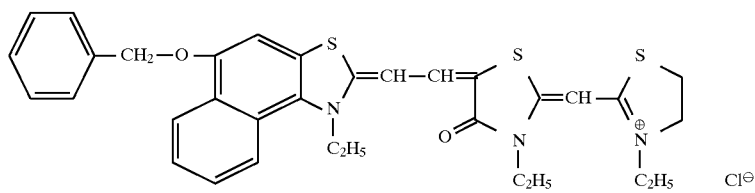 |
| 376 | 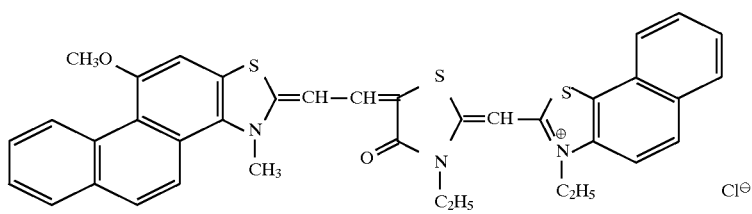 |

-continued

| Compound No. | Structure |
|---|---|
| 377 | 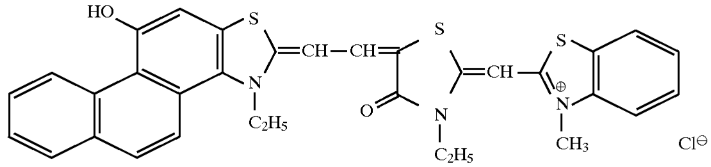 |
| 378 | 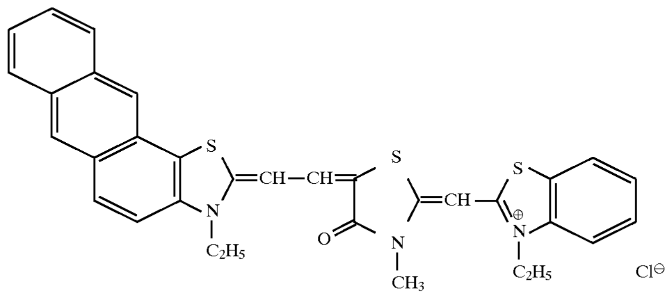 |
| 379 | 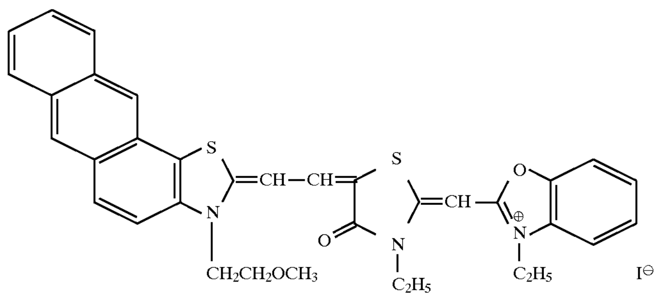 |
| 380 | 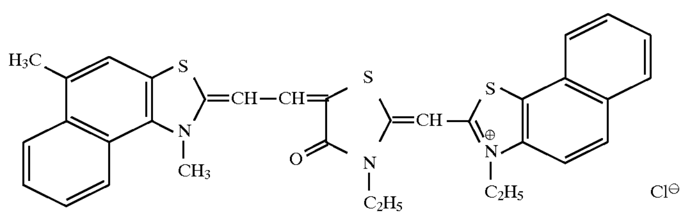 |
| 381 | 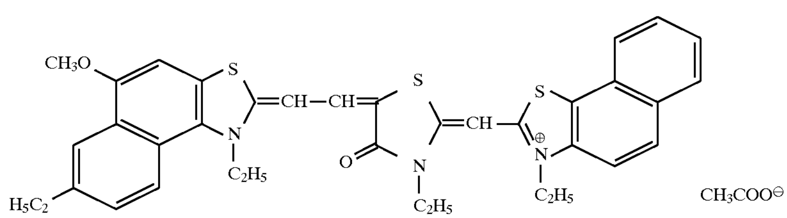 |
| 382 | 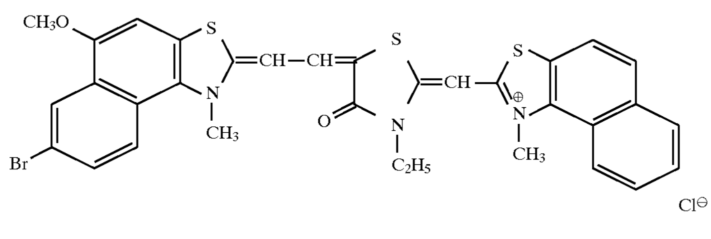 |
| 383 | 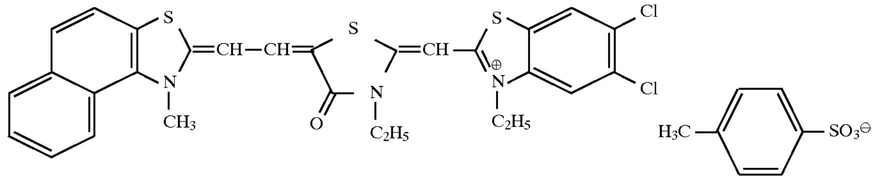 |

| Compound No. | Structure |
|---|---|
| 384 | 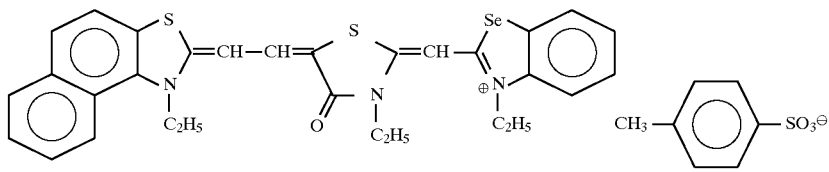 |
| 385 | 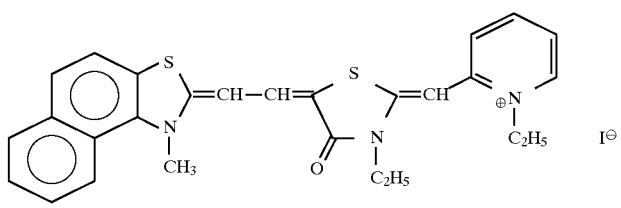 |
| 386 | 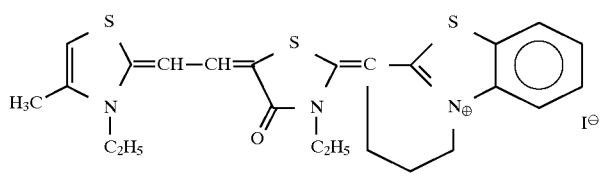 |
| 387 | 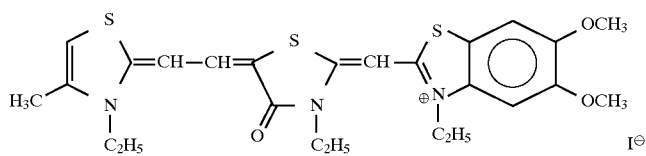 |
| 388 | 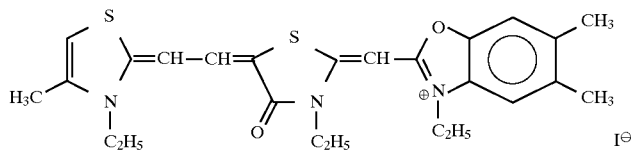 |
| 389 | 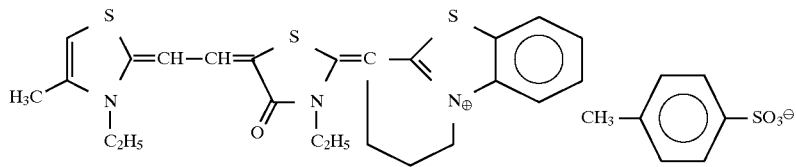 |
| 390 | 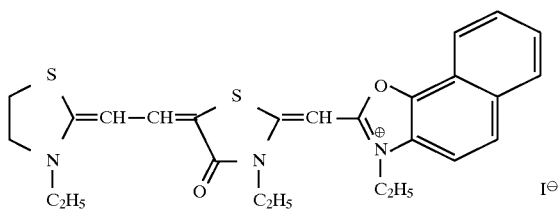 |
| 391 | 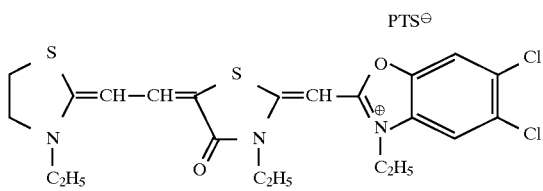 |

5,861,424
137
138
-continued
| Compound No. | Structure |
|---|---|
| 392 | 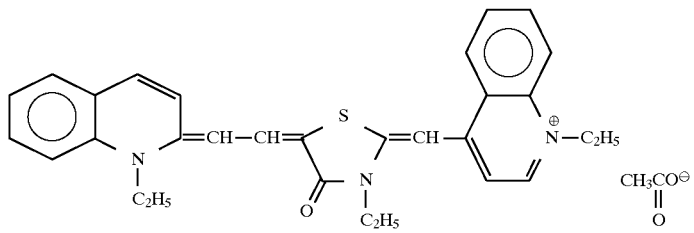 |
| 393 | 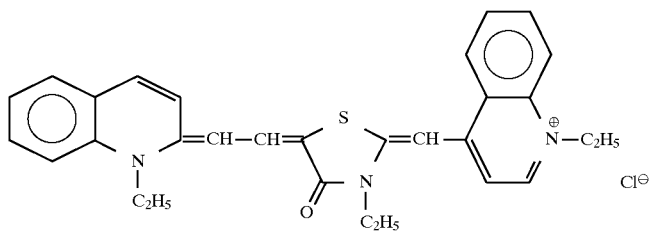 |
| 394 | 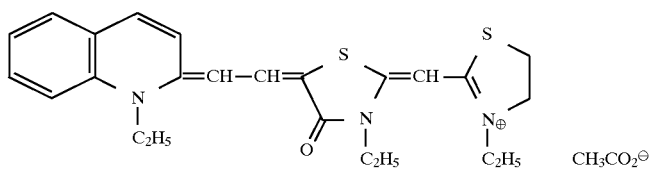 |
| 395 | 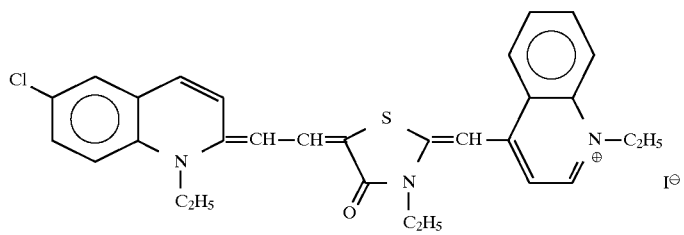 |
| 396 | 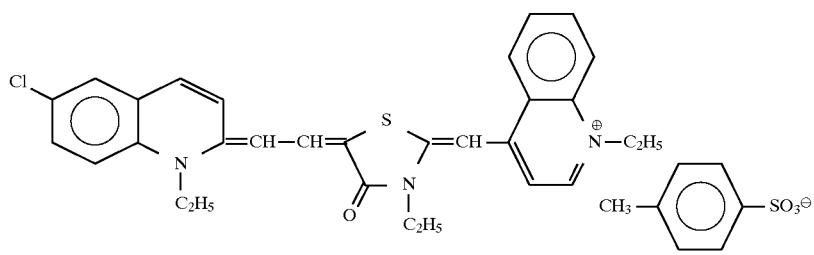 |
| 397 | 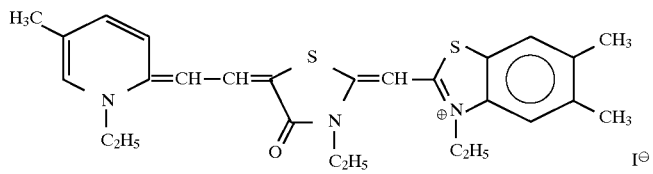 |
| 398 | 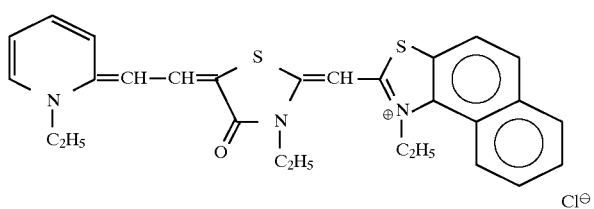 |

| Compound No. | Structure |
|---|---|
| 399 | 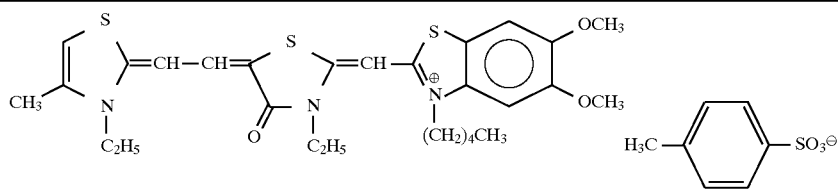 |
| 400 | 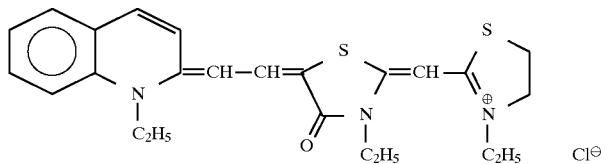 |
| 401 | 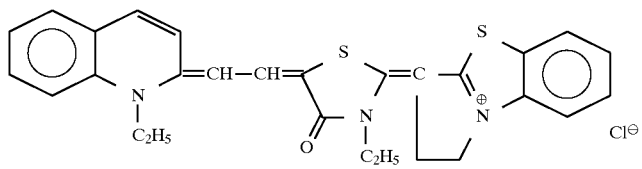 |

The following examples are given to illustrate in greater detail typical synthesis of specific compounds within the scope of the General Formula (1)–(6) above. Unless otherwise indicated herein, all parts, percents, ratios and the like are by weight.

SYNTHESIS EXAMPLE 1-1 (Compound 247)

28 g of 5-[(1-ethyl-2(1H)-1,2-dihydroquinolinylidene)-ethylidene]-2-methylmercapto-4-thiazolone etho-p-toluenesulfonate and 20 g of 1-ethyl-4-methyl-quinolinium p-toluenesulfonate were mixed in 700 cc of acetonitrile.

To the mixture was added 20 cc of triethylamine at ice-water temperature and, after 10 min, 1 l of ethyl acetate was added. Then, the mixture was stirred for 30 min.

The precipitate was filtered off and washed with ethyl acetate. The product obtained was then dissolved in 1 l of methanol and a solution of 20 g of sodium iodide in 50 cc of methanol was added and then the mixture was stirred for 3 hours at room temperature (about 20°–30° C.).

The crude Compound 247 precipitated was filtered off and washed with methanol and dried. After crystallization from methanol/chloroform (1:1 by volume), the pure product was obtained in a yield of 28% with a melting point of 305° to 310° C. (decomp.) $\lambda_{max}^{MeOH}$ 672 nm ($\epsilon_{max}^{MeOH}$=8.00×10⁴).

SYNTHESIS EXAMPLE 1-2 (Compound 262)

(a) Method using Silver Acetate:

To a suspension of 3.5g of Compound 247 produced as described above in 600 cc of chloroform, 2 g of silver acetate was added with stirring at room temperature.

After 1 hour, the reaction mixture was filtered through Celite (Celite 545, a commercially available diatomaceous earth from Manville Sales Corp.) and the filtrate was dried under reduced pressure. To this residue 50 ml of chloroform and then 1 l of ethyl acetate were added.

The product precipitated was collected by suction filtration and washed with ethyl acetate. After drying, 2.55 g of pure Compound 262 was obtained in a yield of 82% with a melting point of 189° to 190° C. (decomp.) $\lambda_{max}^{MeOH}$ 672 nm ($\epsilon_{max}^{MEOH}$=8.00×10⁴).

(b) Method using Ion-Exchange Resin:

100 g of ion-exchange resin (DIATON WA-21, produced by Mitsubishi Chemical Ind. Ltd.) was packed in a column and treated with 1 l of 1N-sodium hydroxide/methanol solution and then treated with 0.5 l of 1N-acetic acid/methanol solution.

7 g of Compound 247 in 1 l of 1N-acetic acid/methanol solution was passed through the column described above.

Compound 262 was eluted with the solution of 1N-acetic acid/methanol solution and the eluent was concentrated to about 200 ml under reduced pressure and to this residue, 0.71 of ethyl acetate was added. The product precipitated was collected by suction filtration and washed with ethyl acetate. After drying, 5.0 g of pure Compound 262 was obtained in a yield of 84%.

The melting point and $\lambda_{max}^{MeOH}$ ($\epsilon_{max}$) were as described.

SYNTHESIS EXAMPLE 2-1 (Compound 55)

17.1g of 5-[(3-methyl-2(1H)-naphtho[1,2-d]thiazolinilidene)ethylidene]-2-mercapto-4-thiazolone etho-p-toluenesulfonate and 12.0 g of 3-ethyl-2-methylnaphtho[2,1-d]thiazolium p-toluene-sulfonate were added to 1000 ml of methanol. The mixture was added to 8 ml of triethylamine at room temperature and stirred 3 hours. The product precipitated was collected by suction filtration and washed with methanol and then recrystallized from chloroform-methanol (1:1 by vol.). The product was obtained in a yield of 60% with a melting point of 300° to 304° C. (decomp.). $\lambda_{max}^{MeOH}$ 621 nm ($\epsilon_{max}^{MeOH}$=1.06×10⁵)

SYNTHESIS EXAMPLE 2-2 (Compound 57)

(a) Method using Concentrated Hydrochloric Acid:

4.0 g of Compound 55 produced as described above, was dissolved in 300 ml of methanol-chloroform (1:1 by vol.) mixture.

To this solution, 4 ml of concentrated (35%) hydrochloric acid was added and then concentrated under reduced pressure until the volume was about 150 ml at 35° C. The product precipitated was collected by suction filtration and washed with ethanol. After recrystallization from methanol-chloroform (1:1 by vol.), 3.2 g of pure Compound 57 was obtained in a yield of 98% with a melting point of 223° to 227° C. (decomp.). $\lambda_{max}^{MeOH}$ 621 nm ($\epsilon_{max}^{MeOH}$=9.72×10⁴).

(b) Method using Ion-Exchange Resin 100 g of an ion-exchange resin (AMBERLYST A-26, produced by Rhom & Haas, Inc.) was packed in a column and then a solution of 6.5 g of Compound 55 in 500 ml of methanol-chloroform (1:1 by vol.) was passed through this column.

Compound 55 was eluted with 2 l of methanol and the eluent was concentrated to about 200 ml. To this residue, 500 ml of ethanol was added and then reconcentrated to about 500 ml.

The product precipitated was collected by suction filteration and washed with ethanol. After drying, 4.6 g of pure Compound 57 was obtained in a yield of 86%. The melting point and $\lambda_{max}^{MeOH}$ ($\epsilon_{max}$) where as described.

SYNTHESIS EXAMPLE 2-3 (Compound 32)

The procedures described above were repeated but using sodium iodide (2.5 mol equivalent) instead of conc. hydrochloric acid. From 24.5 g of Compound 55, 22.7 g of Compound 32 was obtained in a yield of 98% and with a melting point of 223° to 226° C. (decomp.). $\lambda_{max}^{MeOH}$ 621 nm ($\epsilon_{max}^{MeOH}$ =9.71×10⁴).

SYNTHESIS EXAMPLE 2-4 (Compound 56)

16.2 g of Compound 32 was added to 1.6 l of methanol-chloroform (1:1 by vol) mixture and the mixture was stirred at room temperature. To this suspension, 11 g of silver acetate was added and the mixture was stirred 4.5 hours at room temperature.

This reaction mixture was filtered through celite and the filtrate was subjected to evaporation under reduced pressure. The residue was dissolved in 500 cc of methanol and filtered. The filtrate was concentrated under reduced pressure to about 200 cc and then 300 cc of diethyl ether and 100 cc of ethyl acetate were added to this solution to precipitate Compound 56.

The product was collected by suction filtration and 13.5 g of pure Compound 56 was obtained in a yield of 92% and with a melting point of 190° to 194° C. $\lambda_{max}^{MeOH}$ 621 nm ($\epsilon_{max}^{MeOH}$=9.43×10⁴).

Other compounds of the General Formulas (1) to (6) useful in this invention were easily synthesized using procedures similar to those above described. These compounds are shown in Table II below along with their absorption maximum and coefficient of absorption maximum.

TABLE II

| Compound No. | $\epsilon_{max}^{MeOH^*}$ | $\lambda_{max}^{MeOH}$ |
|---|---|---|
| 1 | 9.30 | 586 |
| 2 | 9.31 | 589 |
| 3 | 10.8 | 606 |
| 4 | 7.18 | 656 |
| 5 | 5.32 | 636 |
| 6 | 10.8 | 614 |
| 7 | 11.0 | 620 |
| 8 | 13.4 | 624 |
| 9 | 8.03 | 616 |
| 10 | 10.6 | 598 |
| 11 | 10.9 | 602 |
| 12 | 10.3 | 587 |
| 13 | 8.59 | 636 |
| 14 | 7.01 | 634 |

TABLE II-continued

| Compound No. | $\epsilon_{max}^{MeOH^*}$ | $\lambda_{max}^{MeOH}$ |
|---|---|---|
| 15 | 7.37 | 655 |
| 16 | 10.7 | 626 |
| 17 | 10.9 | 617 |
| 18 | 9.74 | 622 |
| 19 | 7.39 | 658 |
| 20 | 12.5 | 603 |
| 21 | 10.2 | 610 |
| 22 | 11.6 | 616 |
| 23 | 9.15 | 554 |
| 24 | 8.18 | 630 |
| 25 | 11.5 | 625 |
| 26 | 7.41 | 649 |
| 27 | 6.63 | 640 |
| 28 | 6.48 | 651 |
| 29 | 7.06 | 664 |
| 30 | 11.0 | 620 |
| 31 | 10.3 | 623 |
| 33 | 9.28 | 623 |
| 34 | 10.5 | 614 |
| 35 | 11.7 | 600 |
| 36 | 10.8 | 604 |
| 37 | 11.0 | 616 |
| 38 | 11.2 | 616 |
| 39 | 11.0 | 609 |
| 40 | 7.01 | 640 |
| 41 | 10.1 | 593 |
| 42 | 10.2 | 591 |
| 43 | 8.40 | 638 |
| 44 | 9.94 | 622 |
| 45 | 9.84 | 621 |
| 46 | 10.2 | 623 |
| 47 | 8.82 | 620 |
| 48 | 8.71 | 619 |
| 49 | 10.8 | 623 |
| 50 | 10.0 | 627 |
| 51 | 8.19 | 625 |
| 52 | 9.21 | 623 |
| 53 | 10.3 | 624 |
| 54 | 10.7 | 623 |
| 58 | 8.11 | 589 |
| 59 | 7.61 | 599 |
| 60 | 10.8 | 615 |
| 61 | 9.94 | 629 |
| 62 | 10.7 | 615 |
| 63 | 6.31 | 624 |
| 64 | 8.97 | 588 |
| 65 | 9.59 | 588 |
| 66 | 9.42 | 589 |
| 67 | 10.5 | 622 |
| 68 | 10.4 | 622 |
| 69 | 10.8 | 623 |
| 70 | 11.4 | 604 |
| 71 | 11.6 | 617 |
| 72 | 11.3 | 616 |
| 73 | 10.0 | 622 |
| 74 | 11.1 | 619 |
| 75 | 12.1 | 615 |
| 76 | 11.9 | 613 |
| 77 | 11.5 | 617 |
| 78 | 12.1 | 603 |
| 79 | 10.6 | 614 |
| 80 | 11.0 | 604 |
| 81 | 10.3 | 617 |
| 82 | 9.33 | 591 |
| 83 | 8.99 | 601 |
| 84 | 10.9 | 622 |
| 85 | 10.1 | 634 |
| 86 | 6.95 | 641 |
| 87 | 7.02 | 640 |
| 88 | 6.88 | 645 |
| 89 | 6.57 | 652 |
| 90 | 7.98 | 608 |
| 91 | 7.42 | 606 |
| 92 | 8.34 | 606 |
| 93 | 7.09 | 603 |
| 94 | 8.76 | 586 |
| 95 | 9.32 | 607 |

TABLE II-continued

| Compound No. | $\epsilon^{MeOH*}_{max}$ | $\lambda^{MeOH}_{max}$ |
|---|---|---|
| 96 | 6.58 | 606 |
| 97 | 8.45 | 613 |
| 98 | 9.47 | 611 |
| 99 | 10.8 | 620 |
| 100 | 9.66 | 614 |
| 101 | 10.8 | 627 |
| 102 | 9.32 | 611 |
| 103 | 7.72 | 604 |
| 104 | 8.02 | 620 |
| 105 | 8.41 | 616 |
| 106 | 7.55 | 631 |
| 107 | 9.11 | 608 |
| 108 | 9.05 | 608 |
| 109 | 9.01 | 610 |
| 110 | 9.17 | 616 |
| 111 | 9.09 | 611 |
| 112 | 10.1 | 603 |
| 113 | 9.83 | 609 |
| 114 | 8.89 | 615 |
| 115 | 8.55 | 617 |
| 116 | 7.69 | 562 |
| 117 | 8.21 | 562 |
| 118 | 8.37 | 563 |
| 119 | 7.95 | 563 |
| 120 | 8.41 | 563 |
| 121 | 7.99 | 562 |
| 122 | 7.89 | 563 |
| 123 | 8.06 | 559 |
| 124 | 8.27 | 554 |
| 125 | 8.38 | 556 |
| 126 | 8.31 | 556 |
| 127 | 8.16 | 559 |
| 128 | 8.52 | 559 |
| 129 | 8.73 | 557 |
| 130 | 8.56 | 558 |
| 131 | 8.53 | 554 |
| 132 | 8.27 | 554 |
| 133 | 8.93 | 559 |
| 134 | 8.65 | 557 |
| 135 | 7.87 | 549 |
| 136 | 9.12 | 559 |
| 137 | 7.69 | 554 |
| 138 | 8.02 | 562 |
| 139 | 8.47 | 555 |
| 140 | 8.27 | 554 |
| 141 | 7.93 | 552 |
| 142 | 6.96 | 529 |
| 143 | 9.12 | 544 |
| 144 | 8.25 | 557 |
| 145 | 8.27 | 555 |
| 146 | 5.49 | 605 |
| 147 | 5.26 | 584 |
| 148 | 8.43 | 561 |
| 149 | 8.26 | 556 |
| 150 | 7.00 | 561 |
| 151 | 8.34 | 545 |
| 152 | 7.59 | 567 |
| 153 | 8.33 | 559 |
| 154 | 8.33 | 552 |
| 155 | 8.61 | 556 |
| 156 | 7.11 | 560 |
| 157 | 8.46 | 556 |
| 158 | 8.26 | 539 |
| 159 | 6.02 | 575 |
| 160 | 8.08 | 555 |
| 161 | 7.66 | 553 |
| 162 | 7.63 | 558 |
| 163 | 7.65 | 550 |
| 164 | 5.57 | 588 |
| 165 | 5.98 | 577 |
| 166 | 7.57 | 556 |
| 167 | 7.70 | 554 |
| 168 | 7.82 | 557 |
| 169 | 8.05 | 557 |
| 170 | 11.4 | 575 |
| 171 | 11.2 | 566 |
| 172 | 10.8 | 572 |
| 173 | 11.3 | 565 |
| 174 | 10.9 | 560 |
| 175 | 6.90 | 590 |
| 176 | 11.3 | 557 |
| 177 | 10.2 | 583 |
| 178 | 9.60 | 583 |
| 179 | 11.2 | 571 |
| 180 | 9.99 | 590 |
| 181 | 9.76 | 590 |
| 182 | 10.8 | 588 |
| 183 | 8.61 | 588 |
| 184 | 8.31 | 588 |
| 185 | 10.1 | 572 |
| 186 | 9.83 | 603 |
| 187 | 8.85 | 580 |
| 188 | 8.81 | 582 |
| 189 | 9.62 | 587 |
| 190 | 8.99 | 590 |
| 191 | 9.16 | 595 |
| 192 | 9.60 | 569 |
| 193 | 9.21 | 572 |
| 194 | 8.98 | 565 |
| 195 | 7.01 | 576 |
| 196 | 7.11 | 568 |
| 197 | 8.15 | 573 |
| 198 | 7.33 | 558 |
| 199 | 7.95 | 531 |
| 200 | 7.08 | 570 |
| 201 | 6.55 | 590 |
| 202 | 6.61 | 601 |
| 203 | 7.07 | 575 |
| 204 | 8.69 | 568 |
| 205 | 9.51 | 565 |
| 206 | 9.29 | 577 |
| 207 | 9.20 | 576 |
| 208 | 9.33 | 570 |
| 209 | 10.2 | 579 |
| 210 | 5.48 | 593 |
| 211 | 6.98 | 593 |
| 212 | 9.19 | 585 |
| 213 | 9.59 | 582 |
| 214 | 8.75 | 584 |
| 215 | 5.89 | 611 |
| 216 | 8.61 | 553 |
| 217 | 10.0 | 569 |
| 218 | 8.89 | 598 |
| 219 | 8.75 | 598 |
| 220 | 9.13 | 583 |
| 221 | 7.97 | 551 |
| 222 | 8.20 | 562 |
| 223 | 7.57 | 569 |
| 224 | 8.74 | 588 |
| 225 | 8.90 | 565 |
| 226 | 8.55 | 570 |
| 227 | 8.36 | 571 |
| 228 | 8.64 | 553 |
| 229 | 8.57 | 568 |
| 230 | 9.40 | 590 |
| 231 | 6.44 | 587 |
| 232 | 5.69 | 654 |
| 233 | 6.50 | 577 |
| 234 | 7.45 | 586 |
| 235 | 7.76 | 592 |
| 236 | 7.56 | 583 |
| 237 | 7.74 | 565 |
| 238 | 7.33 | 567 |
| 239 | 6.59 | 590 |
| 240 | 7.22 | 581 |
| 241 | 8.25 | 560 |
| 242 | 9.00 | 565 |
| 243 | 8.63 | 580 |
| 244 | 10.5 | 603 |
| 245 | 10.9 | 621 |
| 246 | 7.57 | 653 |
| 248 | 5.73 | 501 |
| 249 | 7.65 | 671 |
| 250 | 12.4 | 631 |

TABLE II-continued

| Compound No. | $\epsilon^{MeOH*}_{max}$ | $\lambda^{MeOH}_{max}$ |
| --- | --- | --- |
| 251 | 12.6 | 624 |
| 252 | 11.3 | 641 |
| 253 | 12.4 | 634 |
| 254 | 13.3 | 635 |
| 255 | 12.9 | 641 |
| 256 | 7.69 | 665 |
| 257 | 10.8 | 640 |
| 258 | 13.7 | 629 |
| 259 | 7.59 | 664 |
| 260 | 6.94 | 665 |
| 261 | 10.7 | 600 |
| 263 | 8.04 | 620 |
| 264 | 6.11 | 657 |
| 265 | 9.66 | 590 |
| 266 | 10.1 | 601 |
| 267 | 11.5 | 613 |
| 268 | 9.81 | 625 |
| 269 | 10.3 | 624 |
| 270 | 7.32 | 655 |
| 271 | 7.02 | 624 |
| 272 | 7.21 | 602 |
| 273 | 7.53 | 606 |
| 274 | 7.44 | 605 |
| 275 | 8.01 | 615 |
| 276 | 8.28 | 604 |
| 277 | 7.98 | 612 |
| 278 | 9.47 | 610 |
| 279 | 6.47 | 671 |
| 280 | 6.73 | 658 |
| 281 | 8.26 | 609 |
| 282 | 5.80 | 646 |
| 283 | 7.76 | 615 |
| 284 | 8.11 | 597 |
| 285 | 8.17 | 608 |
| 286 | 6.66 | 653 |
| 287 | 7.89 | 605 |
| 288 | 7.53 | 607 |
| 289 | 7.47 | 596 |
| 290 | 14.4 | 678 |
| 291 | 15.1 | 671 |
| 292 | 16.0 | 659 |
| 293 | 10.8 | 615 |
| 294 | 13.6 | 671 |
| 295 | 3.46 | 661 |
| 296 | 6.27 | 616 |
| 297 | 13.4 | 668 |
| 298 | 12.5 | 659 |
| 299 | 14.9 | 677 |
| 300 | 13.5 | 675 |
| 301 | 17.1 | 675 |
| 302 | 13.7 | 680 |
| 303 | 8.48 | 722 |
| 304 | 8.63 | 721 |
| 305 | 8.32 | 700 |
| 306 | 15.0 | 679 |
| 307 | 16.2 | 676 |
| 308 | 14.4 | 688 |
| 309 | 13.3 | 677 |
| 310 | 9.51 | 603 |
| 311 | 9.33 | 615 |
| 312 | 10.6 | 681 |
| 313 | 13.3 | 681 |
| 314 | 14.1 | 680 |
| 315 | 6.11 | 730 |
| 316 | 7.40 | 625 |
| 317 | 9.76 | 627 |
| 318 | 9.90 | 635 |
| 319 | 7.59 | 696 |
| 320 | 9.85 | 636 |
| 321 | 8.89 | 613 |
| 322 | 8.65 | 617 |
| 323 | 10.2 | 630 |
| 324 | 9.41 | 603 |
| 325 | 8.05 | 590 |
| 326 | 5.98 | 666 |
| 327 | 10.4 | 606 |
| 328 | 10.9 | 581 |
| 329 | 7.07 | 517 |
| 330 | 6.17 | 530 |
| 331 | 7.78 | 497 |
| 332 | 7.07 | 504 |
| 333 | 5.43 | 525 |
| 334 | 6.81 | 504 |
| 335 | 6.56 | 508 |
| 336 | 10.2 | 620 |
| 337 | 6.2 | 585 |
| 338 | 6.73 | 565 |
| 339 | 5.44 | 661 |
| 340 | 7.20 | 642 |
| 341 | 8.35 | 694 |
| 342 | 8.08 | 690 |
| 343 | 7.11 | 671 |
| 344 | 7.60 | 670 |
| 345 | 8.32 | 681 |
| 346 | 8.03 | 656 |
| 347 | 7.09 | 649 |
| 348 | 7.54 | 669 |
| 349 | 11.2 | 608 |
| 350 | 2.60 | 580 |
| 351 | 12.6 | 617 |
| 352 | 6.40 | 664 |
| 353 | 7.18 | 668 |
| 354 | 8.01 | 687 |
| 355 | 8.44 | 620 |
| 356 | 8.21 | 680 |
| 357 | 8.01 | 675 |
| 358 | 7.92 | 684 |
| 359 | 6.99 | 673 |
| 360 | 7.32 | 683 |
| 361 | 7.95 | 680 |
| 362 | 7.33 | 685 |
| 363 | 8.01 | 680 |
| 364 | 7.11 | 688 |
| 365 | 7.40 | 681 |
| 366 | 7.47 | 684 |
| 367 | 7.91 | 673 |
| 368 | 7.55 | 685 |
| 369 | 6.98 | 670 |
| 370 | 7.06 | 670 |
| 371 | 7.14 | 678 |
| 372 | 9.80 | 618 |
| 373 | 9.76 | 626 |
| 374 | 9.95 | 610 |
| 375 | 9.63 | 593 |
| 376 | 8.86 | 645 |
| 377 | 7.93 | 647 |
| 378 | 9.33 | 630 |
| 379 | 9.54 | 616 |
| 380 | 9.44 | 626 |
| 381 | 9.16 | 627 |
| 382 | 9.58 | 623 |

* × 10$^4$

The pharmaceutical compositions of this invention containing one or more compounds of the General Formulas (1) to (6) described above can be effectively used to treat various types of cancer including melanomas, hepatomas, gliomas, neuroblastomas, sarcomas and carcinomas of the lung, colon, breast, bladder, ovary, testis, prostate, cervix, pancreas, stomach, small intestine and other organs.

The pharmaceutical compositions of this invention can contain one or more compounds of the General Formulas (1) to (6) described above and, if desired, can be employed in combination with other therapeutic agents including conventional anti-tumor agents known in the art. Suitable examples of such conventional anti-tumor agents which can be used include adriamycin, cisplatin, colchicine, CCNU (Lomastine), BCNU (Carmustine), Actinomycin D, 5-fluorouracil, thiotepa, cytosinearabinoside, cyclophosphamide, mitomycin C, and the like.

Suitable examples of pharmaceutical carriers or diluents which can be employed in the pharmaceutical composition of this invention in combination with the compound of the General Formulas (1) to (6) include glucose, sucrose, lactose, ethyl alcohol, glycerin, mannitol, sorbitol, pentaerythritol, diethylene glycol, triethylene glycol, ethylene glycol, propylene glycol, dipropylene glycol, polyethylene glycol 400, other polyethylene glycols, mono-, di- and triglycerides of saturated fatty acids such as glyceryl trilaurate, glyceryl monostearate, glyceryl tristearate and glyceryl distearate, pectin, starch, alginic acid, xylose, talc, lycopodium, oils and fats such as olive oil, peanut oil, castor oil, corn oil, wheat germ oil, sesame oil, cottonseed oil, sunflower seed oil and cod-liver oil, gelatin, lecithin, silica, cellulose, cellulose derivatives such as methyl hydroxypropyl cellulose, methyl cellulose, hydroxyethyl cellulose, magnesium and calcium salts of fatty acids with 12 to 22 carbon atoms such as calcium stearate, calcium laureate, magnesium oleate, calcium palmitate, calcium behenate and magnesium stearate, emulsifiers, esters of saturated and unsaturated fatty acids, e.g., having 2 to 22 carbon atoms, especially 10 to 18 carbon atoms, with monohydric aliphatic alcohols (e.g., having 1 to 20 carbon atoms such as alkanols) or polyhydric alcohols such as glycols, glycerine, diethylene glycol, pentaerythritol, ethyl alcohol, butyl alcohol, octadecyl alcohol and silicones such as dimethyl polysiloxane. Additional carriers conventionally used in pharmaceutical compositions may also be appropriate for this invention.

The pharmaceutically effective amount of the compound of the General Formulas (1) to (6) which can be employed and the mode or manner of administration will be dependent upon the nature of the cancer, the therapy sought, the severity of the disease, the degree of malignancy, the extent of metastatic spread, the tumor load, general health status, body weight, age, sex, and the (genetic) racial background of the patient. However, in general, suitable modes of administration include intravenous, intraperitoneal, intramuscular or intravesicular injection in the form of, for example, a compound of the General Formulas (1) to (6) in, e.g., a 5% glucose aqueous solution or with other appropriate carriers or diluents as described above. A suitable therapeutically effective amount of a compound of the General Formulas (1) to (6) in the composition is about 0.01% by weight to about 10% by weight, more generally 0.1% by weight to about 1%, based on the weight of the composition.

Again, as noted above, pharmaceutically effective amounts will be generally determined by the practitioner based on the clinical symptoms observed and degree of progression of disease and like factors but a suitable therapeutically effective amount of the compound of the General Formulas (1) to (6) generally can range from 10 mg to 500 mg, more generally 100 mg to 200 mg, administered per day per 70 kg of body weight, in single or multiple doses, as determined appropriate for the therapy involved.

In order to demonstrate the effectiveness of the compounds of the General Formulas (1) to (6) and the pharmaceutical compositions and method of this invention, the following examples are given to demonstrate effectiveness and selectivity values for a number of the compounds of the initial General Formulas (1) to (6) employed in the composition and method of this invention as well as compounds for comparison. The results obtained are shown in the tables below.

EXAMPLE 1

The data obtained in Table III below were obtained in the following manner.

Human colon carcinoma cell line CX-1 or normal monkey kidney epithelial cell line CV-1 was chosen as representatives of cancer cells and normal cells, respectively. This assay demonstrates the selective killing of cancer cells by compounds of the General Formula (I). CX-1 cells (2,000 cells/well) and CV-1 cells (1,000 cells/well) were plated in 24-well plastic culture plates. Compounds of General Formulas (1) to (6) were dissolved in dimethylsulfoxide at a concentration of 1 mg/ml and serial dilutions of this solution in cell culture media at concentrations varying from 20 µg/ml to 0.0025 µg/ml were added to individual wells. The control received culture media only. Cells were treated with compounds of General Formulas (1) to (6) at 37° C. for 24 hours. After rinsing with fresh culture medium three times, the cells were further incubated at 37° C. for 7 to 10 days. Cell colonies were fixed and stained with 2% crystal violet in 70% ethanol for 10 minutes and rinsed in water. The number of colonies in each well were counted and the concentration of compounds at which the colony number was reduced to 50% of the control ($IC_{50}$.) was determined. The selectivity is defined as the ratio of $IC_{50}$ for CV-1 and $IC_{50}$ for CX-1.

TABLE III

| Compound No. | CV-1 ($IC_{50}$) µg/ml | CX-1 ($IC_{50}$) µg/ml | Selectivity |
| --- | --- | --- | --- |
| 6 | 10 | 0.025 | 400 |
| 7 | 4 | 0.04 | 100 |
| 12 | 1 | 0.01 | 100 |
| 20 | 6 | 0.03 | 200 |
| 30 | 5 | 0.025 | 200 |
| 31 | 10 | 0.025 | 400 |
| 32 | 20 | 0.02 | 1000 |
| 33 | 20 | 0.02 | 1000 |
| 37 | 5 | 0.02 | 250 |
| 40 | 5.14 | 0.02 | 257 |
| 44 | 20 | 0.02 | 1000 |
| 45 | 20 | 0.02 | 1000 |
| 46 | 20 | 0.05 | 400 |
| 47 | 20 | 0.05 | 400 |
| 48 | 20 | 0.005 | 4000 |
| 49 | 20 | 0.03 | 667 |
| 51 | 10 | 0.03 | 333 |
| 52 | >20 | 0.03 | >667 |
| 53 | 20 | 0.05 | 400 |
| 54 | 20 | 0.04 | 500 |
| 56 | 20 | 0.1 | 200 |
| 67 | 10 | 0.05 | 200 |
| 68 | 5 | 0.0.5 | 100 |
| 69 | 5 | 0.05 | 100 |
| 70 | 10 | 0.04 | 250 |
| 74 | 10 | 0.1 | 100 |
| 92 | 9 | 0.05 | 180 |
| 96 | 20 | 0.03 | 667 |
| 97 | 2 | 0.01 | 200 |
| 123 | 20 | 0.1 | 200 |
| 124 | 5 | 0.03 | 167 |
| 125 | 8 | 0.04 | 200 |
| 134 | 10 | 0.1 | 100 |
| 137 | 5 | 0.05 | 100 |
| 138 | 0.8 | 0.005 | 160 |
| 141 | 20 | 0.05 | 400 |
| 142 | 20 | 0.1 | 200 |
| 143 | 5 | 0.05 | 100 |
| 145 | 10 | 0.05 | 200 |
| 150 | 1 | 0.01 | 100 |
| 151 | 20 | 0.08 | 250 |
| 154 | 5 | 0.04 | 125 |
| 157 | 8 | 0.08 | 100 |
| 178 | 2 | 0.01 | 200 |
| 185 | 2.0 | 0.05 | 400 |
| 206 | 6 | 0.01 | 600 |
| 207 | 1.5 | 0.01 | 150 |
| 208 | 6 | 0.01 | 600 |

TABLE III-continued

| Compound No. | CV-1 (IC$_{50}$) µg/ml | CX-1 (IC$_{50}$) µg/ml | Selectivity |
|---|---|---|---|
| 209 | 1 | 0.01 | 100 |
| 214 | 8 | 0.03 | 267 |
| 220 | 5 | 0.04 | 125 |
| 230 | 15 | 0.05 | 375 |
| 234 | 10 | 0.03 | 333 |
| 235 | >20 | 0.05 | >400 |
| 247 | 20 | 0.1 | 200 |
| 249 | 5 | 0.05 | 100 |
| 252 | >20 | 0.1 | >200 |
| 253 | >20 | 0.04 | >500 |
| 254 | 10 | 0.1 | 100 |
| 278 | 10 | 0.03 | 333 |
| 290 | 2.5 | 0.025 | 100 |
| 307 | 3 | 0.02 | 150 |
| 317 | 20 | 0.2 | 100 |
| 330 | 2.5 | 0.025 | 100 |
| A | 2 | 0.04 | 50 |
| B | 0.6 | 0.03 | 20 |
| C | <0.1 | 0.05 | <2 |
| 383 | 20 | 0.1 | 200 |
| 384 | 10 | 0.1 | 100 |
| 385 | 20 | 0.2 | 100 |
| 386 | 10 | 0.1 | 100 |
| 381 | 20 | 0.2 | 100 |
| 388 | 8 | 0.03 | 261 |
| 389 | 15 | 0.08 | 188 |
| 390 | 20 | 0.08 | 250 |
| 391 | 8 | 0.07 | 114 |
| 392 | 20 | 0.01 | 286 |
| 393 | 20 | 0.05 | 400 |
| 394 | 10 | 0.08 | 125 |
| 395 | 20 | 0.2 | 100 |
| 396 | 20 | 0.08 | 250 |
| 391 | 20 | 0.05 | 400 |
| 398 | 16 | 0.04 | 400 |
| 399 | 10 | 0.1 | 100 |
| 400 | >20 | 0.08 | >250 |

Compounds A, B and C used for comparison were as follows:

From the results set forth in Table III above, it is very clear that the compounds of the General Formulas (1) to (6) used in this invention have distinctively high selectivity values in comparison with Compounds A, B and C for comparison.

Based on information available in the literature, Compounds B and C with a selectivity of 20 and <2, respectively, would be highly toxic to animals and, therefore, humans. Indeed, it has been found that B and C are highly toxic to normal nude mice. Although Compound A is less toxic to normal nude mice, because of its lower selectivity compared with other compounds of General Formulas (1) to (6), it is expected to have lower efficacy in treating cancers in animals as well as in humans.

EXAMPLE 2

To further demonstrate the uniqueness of the present invention, compounds of the General Formulas (1) to (6) were tested using the protocol described in Example 1 except that the human bladder carcinoma EJ cell line was used instead of the human colon carcinoma cell line CX-1. The selectivity values, EJ values and CV-1 values for compounds of the present invention are shown in Table IV below.

TABLE IV

| Compound No. | CV-1 (IC$_{50}$) µg/ml | EJ (IC$_{50}$) µg/ml | Selectivity |
|---|---|---|---|
| 37 | 5 | 0.03 | 167 |
| 45 | 20 | 0.05 | 400 |
| 46 | 20 | 0.082 | 244 |
| 47 | 20 | 0.082 | 244 |
| 49 | 20 | 0.045 | 444 |
| 51 | 10 | 0.04 | 500 |
| 52 | >20 | 0.05 | >400 |
| 54 | 20 | 0.04 | 500 |
| 56 | 20 | 0.09 | 222 |
| 97 | 2 | 0.013 | 154 |

Compound No. Structural Formula

A 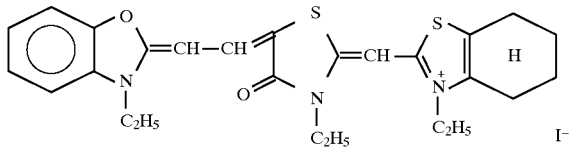

B 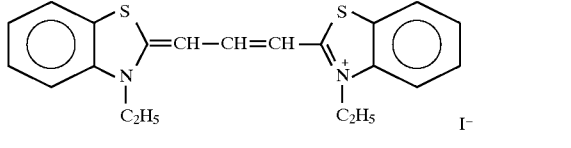

C 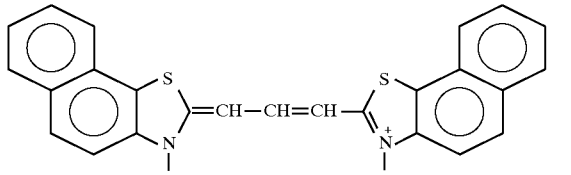

TABLE IV-continued

| Compound No. | CV-1 (IC$_{50}$) µg/ml | EJ (IC$_{50}$) µg/ml | Selectivity |
|---|---|---|---|
| 123 | 20 | 0.13 | 154 |
| 124 | 5 | 0.05 | 100 |
| 125 | 8 | 0.06 | 133 |
| 145 | 10 | 0.082 | 122 |
| 206 | 6 | 0.013 | 462 |
| 214 | 8 | 0.04 | 200 |
| 230 | 15 | 0.05 | 300 |
| 235 | 10 | 0.02 | 500 |

EXAMPLE 3

To further demonstrate the uniqueness of the present invention, compounds of the General Formulas (1) to (6) were tested using the protocol described in Example 1 except that the human melanoma LOX cell line was used instead of the human colon carcinoma cell line CX-1. The Selectivity values, LOX values and CV-1 values for compounds of the present invention are shown in Table V below.

TABLE V

| Compound No. | CV-1 (IC$_{50}$) µg/ml | LOX (IC$_{50}$) µg/ml | Selectivity |
|---|---|---|---|
| 37 | 5 | 0.05 | 100 |
| 45 | 20 | 0.07 | 286 |
| 46 | 20 | 0.064 | 312 |
| 47 | 20 | 0.082 | 244 |
| 48 | 20 | 0.01 | 200 |
| 49 | 20 | 0.075 | 267 |
| 51 | 10 | 0.09 | 222 |
| 52 | >20 | 0.08 | >250 |
| 54 | 20 | 0.07 | 286 |
| 96 | 20 | 0.09 | 222 |
| 97 | 2 | 0.015 | 133 |
| 124 | 5 | 0.04 | 125 |
| 125 | 8 | 0.06 | 133 |
| 141 | 20 | 0.064 | 312 |
| 145 | 10 | 0.064 | 156 |
| 206 | 6 | 0.03 | 196 |
| 208 | 6 | 0.039 | 154 |
| 214 | 8 | 0.04 | 200 |
| 230 | 15 | 0.06 | 200 |
| 234 | 10 | 0.03 | 333 |
| 278 | 10 | 0.035 | 286 |

EXAMPLE 4

To further demonstrate the uniqueness of the present invention, compounds of the General Formulas (1) to (6) were tested using the protocol described in Example 1 except that the human breast carcinoma MCF-7 cell line was used instead of the human colon carcinoma cell line CX-1. The Selectivity values, MCF-7 values and CV-1 values for compounds of the General Formulas (1) to (6) used in the present invention are shown in Table VI below.

TABLE VI

| Compound No. | CV-1 (IC$_{50}$) µg/ml | MCF-7 (IC$_{50}$) µg/ml | Selectivity |
|---|---|---|---|
| 37 | 5 | 0.05 | 100 |
| 45 | 20 | 0.06 | 333 |
| 46 | 20 | 0.082 | 244 |
| 47 | 20 | 0.1 | 200 |
| 49 | 20 | 0.06 | 333 |
| 52 | >20 | 0.03 | >666 |
| 54 | 20 | 0.05 | 400 |
| 125 | 8 | 0.06 | 133 |
| 141 | 20 | 0.184 | 109 |
| 145 | 10 | 0.1 | 100 |
| 178 | 2 | 0.0046 | 435 |
| 206 | 6 | 0.048 | 125 |
| 230 | 15 | 0.09 | 167 |
| 234 | 10 | 0.05 | 200 |
| 278 | 10 | 0.09 | 111 |

EXAMPLE 5

To further demonstrate the uniqueness of the present invention, compounds of the General Formulas (1) to (6) were tested using the protocol described in Example 1 except that the human pancreatic carcinoma CRL 1420 cell line was used instead of the human colon carcinoma cell line CX-1. The Selectivity values, CRL 1420 values and CV-1 values for compounds of the General Formulas (1) to (6) used in the present invention are shown in Table VII below.

TABLE VII

| Compound No. | CV-1 (IC$_{50}$) µg/ml | CRL-1420 (IC$_{50}$) µg/ml | Selectivity |
|---|---|---|---|
| 32 | 20 | <0.1 | >200 |
| 37 | 5 | 0.03 | 167 |
| 40 | 2 | 0.05 | 100 |
| 41 | 1.5 | 0.05 | 120 |
| 45 | 20 | 0.07 | 286 |
| 46 | 20 | 0.064 | 312 |
| 47 | 20 | 0.064 | 312 |
| 49 | 20 | 0.075 | 267 |
| 51 | 10 | 0.07 | 286 |
| 52 | >20 | 0.06 | >333 |
| 53 | 20 | 0.18 | 111 |
| 54 | 20 | 0.05 | 400 |
| 56 | 20 | <0.046 | >435 |
| 123 | 20 | 0.13 | 154 |
| 124 | 5 | 0.04 | 125 |
| 125 | 8 | 0.05 | 160 |
| 141 | 20 | 0.045 | 444 |
| 145 | 10 | 0.082 | 122 |
| 178 | 2 | 0.013 | 154 |
| 206 | 6 | 0.03 | 196 |
| 214 | 8 | 0.04 | 200 |
| 230 | 15 | 0.05 | 300 |
| 234 | 10 | 0.03 | 333 |
| 249 | 5 | 0.045 | 111 |
| 278 | 10 | 0.04 | 250 |

EXAMPLE 6

Nude Mice Bearing Human Melanoma as a Model System

LOX, a human melanoma cell line, grown subcutaneously in nude mice was excised, trypsinized to yield a single cell suspension using a metal grid with a 4 mm mesh. Red blood cells were lysed by incubation with 0.17 molar ammonium chloride at 4° C. for 20 minutes. Five million viable trypan blue negative cells made up in 0.1 ml of Dulbecco modified Eagles' medium (DME) were injected into the peritoneal cavity of a male athymic Swiss nu/nu mouse. The control group and each treatment group consisted of 5 to 10 mice. Treatment was commenced the following day by intraperitoneal injection.

Ten control mice received 0.25 ml of 2% dextrose on those days the treated groups were injected with the compounds of this invention. The compounds of the General Formulas. (1) to (6) used in this invention which were tested are listed in Table VIII below and the results obtained are shown in Table VIII and FIG. 1–6 of the accompanying drawings. T/C is the ratio, expressed as a percentage of the mean survival age of the treated group to the mean survival age of the untreated control group.

TABLE VIII

Survival Rate (%) of Nude Mice Implanted with Human Melanoma LOX

| Test No. | Compound No. | Dose (mg/kg) | Schedule (i.p. on day) | T/C (%) |
|---|---|---|---|---|
| 1 | 6 | 5 | 1, 3, 5, 7 | 126 |
| 2 | 31 | 40 | 1, 2, 3, 4, 8, 10, 17 | 169 |
| 3 | 32 | 40 | 1, 2, 3, 4, 5, 7, 8, 9, 10 | 231 |
| 4 | 33 | 10 | 1, 2, 3, 4, 5, 7, 8, 9, 10, 11 | 173 |
| 5 | 41 | 5 | 1, 5, 9 | 128 |
| 6 | 45 | 20 | 1, 2, 3, 6, 9, 13 | 137 |
| 7 | 46 | 20 | 1, 3, 6, 9, 13, 16 | 222 |
| 9 | 47 | 20 | 1, 3, 6, 9, 13, 16, | 156 |
| 9 | 51 | 20 | 1, 2, 3, 6, 9, 13 | 174 |
| 10 | 52 | 10 | 1, 2, 3, 6, 9 | 168 |
| 11 | 53 | 20 | 1, 3, 6, 9, 13, 16 | 222 |
| 12 | 96 | 2 | 1, 2, 3*, 6*, 9*, 13*, 16* | 253 |
| 13 | 150 | 5 | 1, 2, 9, 13, 16 | 216 |
| 14 | 204 | 5 | 1, 4, 7, 10, 13, 16, 19, 22 | 174 |
| 15 | 244 | 10 | 1, 3, 5, 7, 9 | 153 |
| 16 | 247 | 20 | 1, 2, 3, 4, 8, 9 | 227 |
| 17 | 116 | 5 | 1, 5, 9, 13, 17, 22 | 582 |
| 18 | 330 | 5 | 1, 3, 5, 7, 9 | 128 |

*4 mg/kg of body weight

EXAMPLE 7

Ovarian Carcinoma Test Using Nude Mice Protocol

Figure 9:
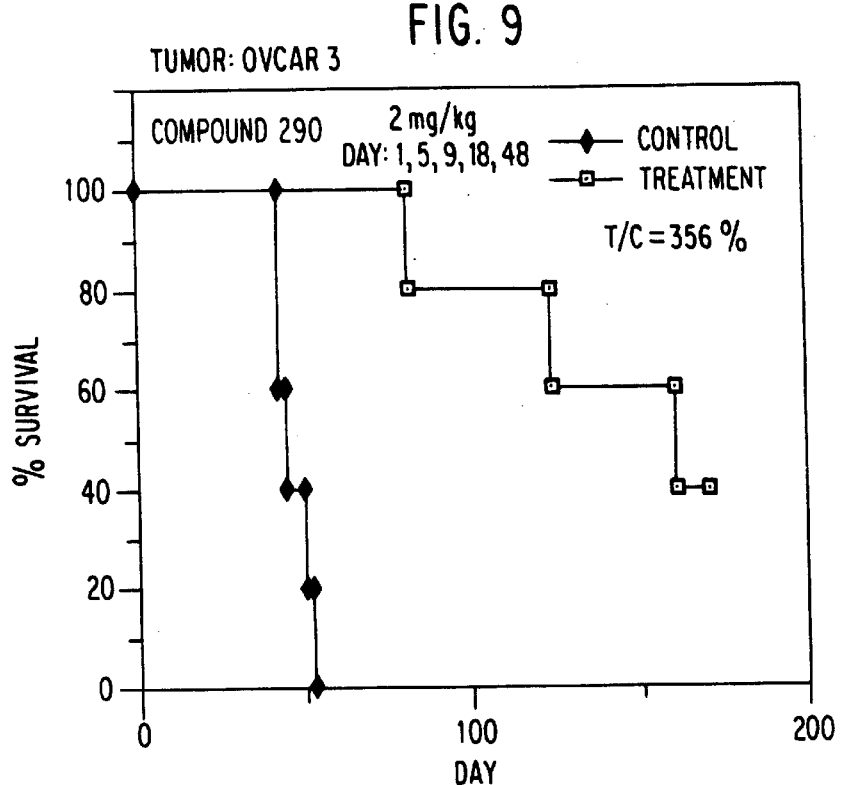
Figure 10:
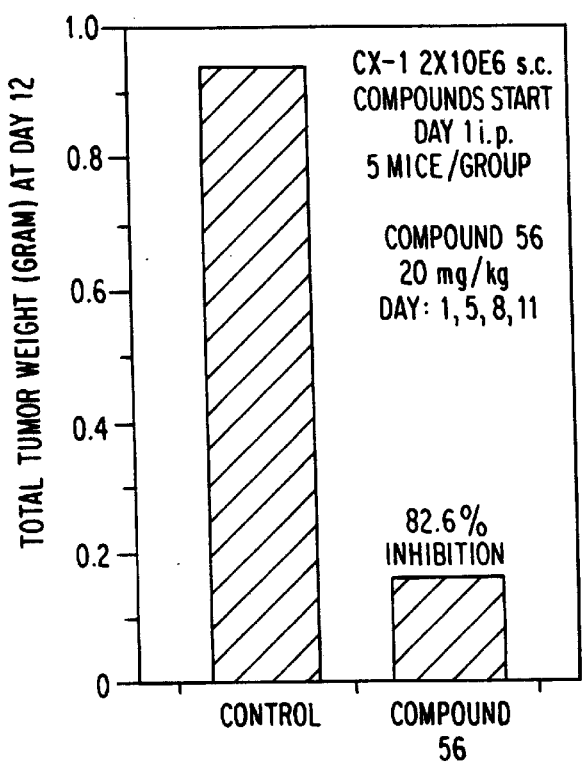
Figure 11:
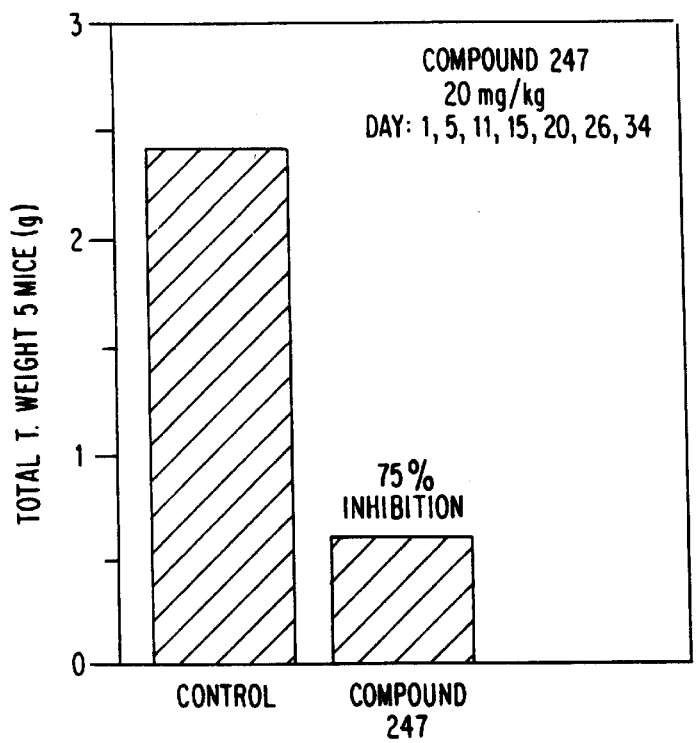
Figure 12:
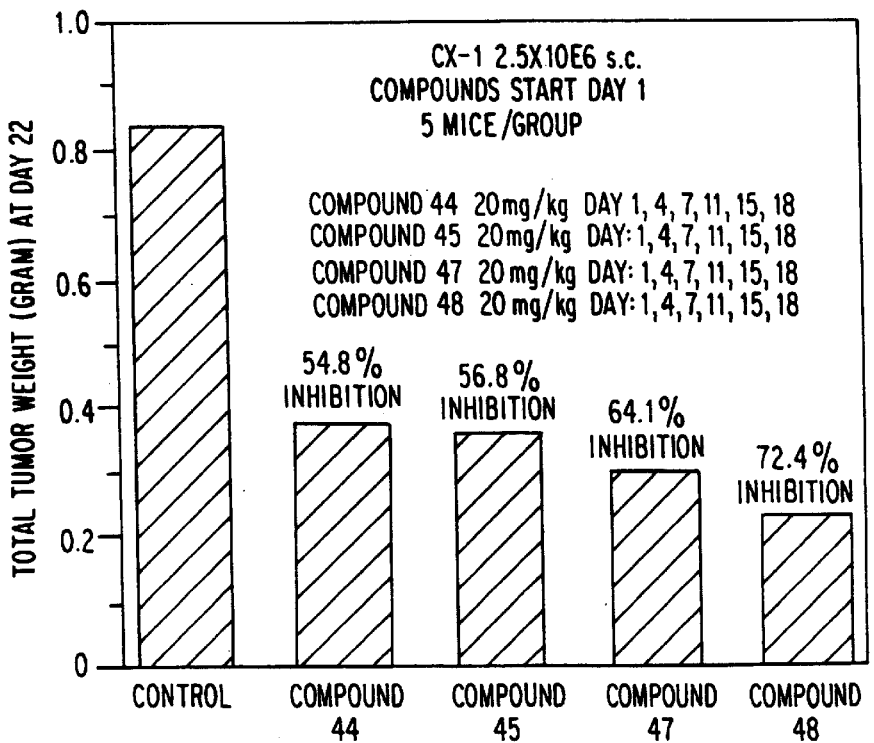
Figure 13:
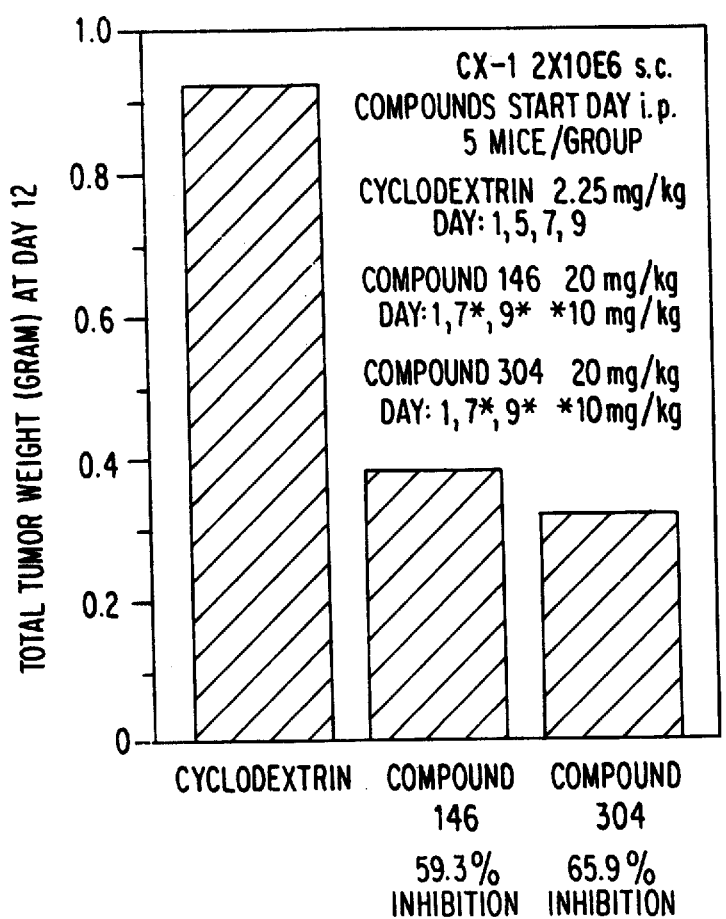

A human ovarian carcinoma cell line, OVCAR-3, was used. Ten million cells of this cell line were injected IP into ten athymic Swiss nu/nu mice. Ten mice into which these cancer cells had been injected were selected as a control group and received in equal volume of 5% dextrose as that of the treated group. The compounds of the General Formulas (1) to (6) which were tested and the results obtained are shown in Table IX below and in FIG. 7–9 of the accompanying drawings.

TABLE IX

Survival Rate (%) of Nude Mice Implanted with Human Ovarian Carcinoma OVCAR-3

| Test No. | Compound No. | Dose (mg/kg) | Schedule (i.p. on day) | T/C (%) |
|---|---|---|---|---|
| 2-1 | 116 | 5 | 1, 5, 9, 14, 19, 23, 27, 48 | >378 |
| 2-2 | 247 | 20 | 1, 5, 9, 14, 23, 48 | >378 |
| 2-3 | 290 | 2 | 1, 5, 9, 18, 48 | 356 |

EXAMPLE 8

Anti-Human Colon Carcinoma CX-1 Activity Using Nude Mice

Human colon carcinoma cell line CX-1 has been chosen by the National Cancer Institute as a mode for cancer drug screening (NCI Protocol 3C2H2). It was established in culture from the surgical explant of the primary colon adenocarcinoma of a 44 year old woman with no previous chemotherapy. The cultured CX-1 cells, upon subcutaneous injection, can grow readily in nude mice as a moderately- to well-differentiated human colon carcinoma. CEA is expressed as expected for differentiated colon carcinoma cells. Abundant keratin, consistent with epithelial origin, is present. Increased uptake and prolonged retention of delocalized lipophilic cations are observed.

Swiss nu/nu mice obtained from Taconic Farm were housed in a pathogen-free environment. Tumors subcutaneously passaged in nude mice were excised under sterile conditions and converted to a single cell suspension using a metal grid with a 0.4 mm mesh. Red blood cells were lysed by incubation with 0.17M ammonium chloride at 4° C. for 20 minutes. Cells were scored for viability with trypan blue. Viable CX-1 cells (2.5 million) made up in 0.1 ml of cell culture medium were injected subcutaneously into each nude mouse. The mice were randomly allocated into a control group (five mice) and a treatment group (five mice per group). The drug treatment was commenced the next day. Doses and schedules were developed empirically and were based mainly on information on LD50 and LD10 obtained from preliminary toxicity studies. The control group received an equivalent volume of hydroxylpropyl-β-cyclodextrin-5% glucose solution.

The pharmaceutical compositions tested comprised solutions in 5% glucose subjected to sonication at concentrations of 1 mg/ml. Those compounds which were not completely dissolved by this procedure were dissolved in hydroxypropyl-β-cyclodextrin using the following method. Hydroxypropyl-β-cyclodextrin (45 g) was mixed with 100 ml of sterilized, double distilled water and stirred for four hours. Each of the compounds to be tested (20 mg) was mixed with 10 ml of hydroxypropyl-β-cyclodextrin solution and sonicated for 60 minutes in the dark. This solution was then diluted in 5% glucose to yield a final compound concentration of 0.5 mg/ml, and further sonicated for 60 minutes in the dark to assure that the compound was completely dissolved.

When the growth of tumors in the control group reached the exponential phase and the size of the tumor was palpable (usually 20 to 30 days after tumor implantation), the experiments were terminated. Tumors in each mouse were excised and weighed using an analytical balance. Total tumor weight in each group from five mice was calculated. Per cent tumor inhibition between the treated group and the control group was then calculated for each group.

The results obtained are shown in Table X below and graphically in FIG. 10–13.

TABLE X

| Test No. | Compound No | Dose (mg/kg) | Schedule (i.p. on day) | Tumor Inhibition (%) |
|---|---|---|---|---|
| 1 | 15 | 20 | 1, 5, 7, 9 | 33.4 |
| 2 | 32 | 20 | 1, 2, 4, 6, 8 | 40.5 |
| 3 | 44 | 20 | 1, 4, 7, 11, 15, 18 | 54.8 |
| 4 | 45 | 20 | 1, 4, 7, 11, 15, 18 | 56.8 |
| 5 | 46 | 20 | 1, 5, 7, 9 | 60.1 |
| 6 | 47 | 20 | 1, 4, 7, 11, 15, 18 | 64.1 |
| 7 | 48 | 20 | 1, 4, 7, 11, 15, 18 | 72.4 |
| 8 | 304 | 20 | 1, 7**, 9** | 65.9 |
| 9 | 54 | 5 | 1, 5, 9, 13 | 42.6 |
| 10 | 55 | 20 | 1, 4, 7, 11, 15, 18 | 55.3 |

TABLE X-continued

| Test No. | Compound No | Dose (mg/kg) | Schedule (i.p. on day) | Tumor Inhibition (%) |
|---|---|---|---|---|
| 11 | 56 | 20 | 1, 5, 8, 11 | 82.6 |
| 12 | 116 | 5 | 1, 6, 10, 14, 19, 23 | 77 |
| 13 | 146 | 20 | 1, 7**, 9** | 59.3 |
| 14 | 247 | 20 | 1, 5, 11, 15, 20, 26, 34 | 75 |
| 15 | 249 | 20 | 1, 5, 7, 9 | 41.1 |

*2.5 mg/kg
**10 mg/kg

While the invention has been described in detail and with reference to specific embodiments thereof, it will be apparent to one skilled in the art that various changes and modifications can be made without departing from the spirit and scope of the invention.

What is claimed is:

1. A pharmaceutical composition for treatment of cancer in an animal, wherein said cancer is sensitive to said pharmaceutical composition and said pharmaceutical composition comprises:

(A) a therapeutically effective amount of at least one compound selected from the group consisting of compounds represented by the General Formulas (1) to (6)

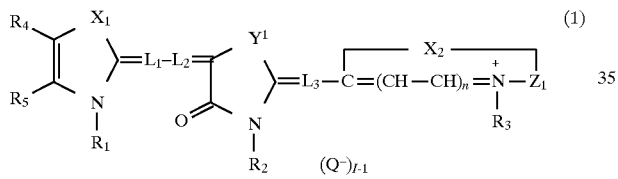

(1)

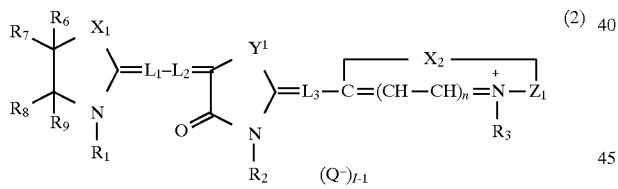

(2)

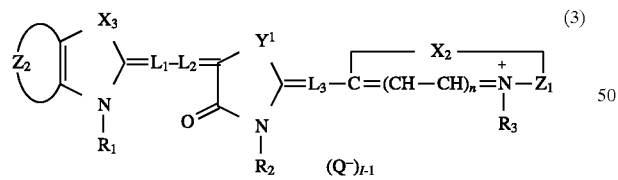

(3)

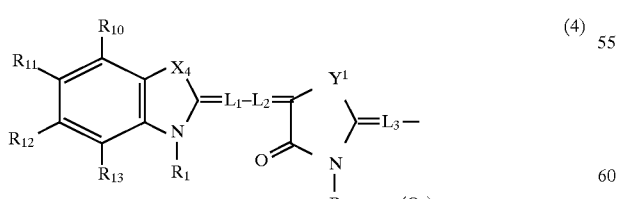

(4)

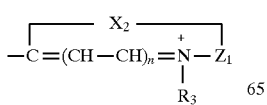

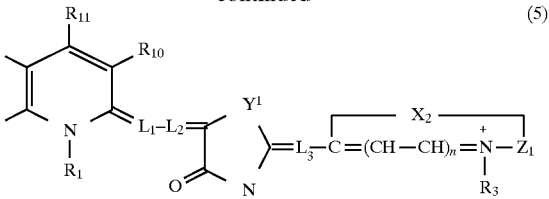

(5)

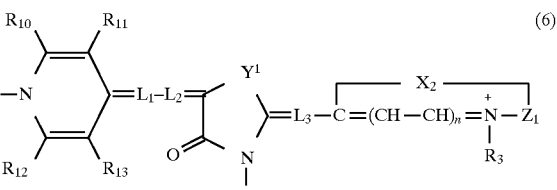

(6)

wherein
$X_1$ is O, S, Se, or >N—$R_{14}$,
$X_2$ is O, S, Se,

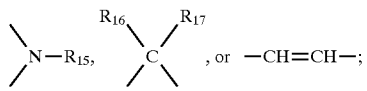, or —CH=CH—;

$X_3$ is O, S, or Se,
$X_4$ is

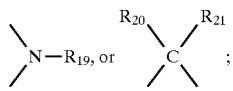 ;

$Y_1$ is O, S, Se, or >N—$R_{18}$;
$Z_1$ represents an atomic group necessary to form a saturated or unsaturated 5- or 6-membered ring selected from the group consisting of a thiazole ring, a benzothiazole ring, a naphthothiazole ring, an oxazole ring, a benzoxazole ring, a naphthoxazole ring, a selenazole ring, a benzoselenazole ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring and a naphthimidazole ring
$Z_2$ represents an atomic group necessary to form a naphthalene ring, an anthracene ring or a phenanthrene ring;
$R_1$, $R_3$, $R_{14}$, $R_{15}$, and $R_{19}$, which may be the same or different, each represents an alkyl group having 1 to 15 carbon atoms
$R_2$ and $R_{18}$, which may be the same or different, each represents an alkyl group having 1 to 15 carbon atoms, an aryl group having 6 to 20 carbon atoms or a heterocyclic ring selected from the group consisting of an imidazole ring, a thiazole ring, a pyrrole ring, a pyrazole ring, a furan ring, a thiophene ring, a piperidine ring, a morpholine ring, a piperadine ring, a pyrazine ring, a pyridine ring, and a pyrimidine ring;
$L_1$, $L_2$ and $L_3$, which may be the same or different, each represents a methine group and $L_1$ and $R_1$ and/or $L_3$ and $R_3$ may combine and form a saturated or unsaturated 5- or 6-membered ring;
$R_4$ and $R_5$, which may be the same or different, each represent a hydrogen atom, an alkyl group having 1 to 15 carbon atoms or an aryl group having 6 to 20 carbon atoms;

$R_6$, $R_7$, $R_8$, and $R_9$, which may be the same or different, each represents a hydrogen atom, an alkyl group having 1 to 15 carbon atoms or an aryl group having 6 to 20 carbon atoms or any two of $R_6$ to $R_9$ may combine and form a saturated or unsaturated 5- or 6-membered ring;

$R_{10}$, $R_{11}$, $R_{12}$ and $R_{13}$, which may be the same or different, each represents a hydrogen atom, an alkyl group having 1 to 15 carbon atoms, an aryl group having 6 to 20 carbon atoms, an alkoxy group having 1 to 15 carbon atoms, an aryloxy group having 6 to 20 carbon atoms, an acyl group, an alkoxycarbonyl group, a trifluoromethyl group, a benzoyl group, a ureido group, an amino group, an amido group, an sulfamido group, a carbamyl group, a sulfamoyl group, a halogen atom, a nitro group, a cyano group, a hydroxyl group or a carboxyl group, or any adjacent two of $R_{10}$ to $R_{13}$ may combine and form a saturated or unsaturated 5- or 6-membered ring, which may have other rings fused therewith;

$R_{16}$, $R_{17}$, $R_{20}$ and $R_{21}$, which may be the same or different, each represents an alkyl group having 1 to 15 carbon atoms;

Q represents a pharmaceutically acceptable anion;

n represents 0 or 1; and l represents 1 or 2, in combination with (B) a sterile pharmaceutically acceptable carrier or diluent.

2. The composition of claim 1, wherein said at least one compound of the General Formulas (1) to (6) is a compound selected from the group consisting of compounds represented by the General Formula (1)

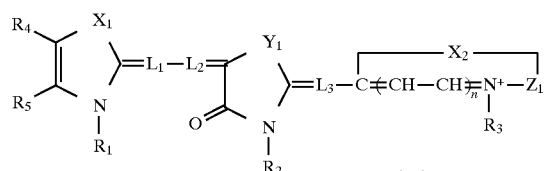

wherein $X_1$, $X_2$, $Y_1$, $Z_1$, $R_1$, $R_2$, $R_3$, $R_4$, $R_5$, $L_1$, $L_2$, $L_3$, Q, n and l are as defined in claim 1.

3. The composition of claim 1, wherein said at least one compound of the General Formulas (1) to (6) is a compound selected from the group consisting of compounds represented by the General Formula (2)

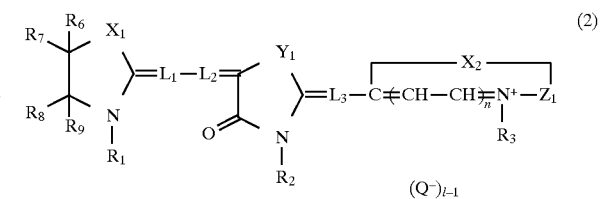

wherein $X_1$, $X_2$, $Y_1$, $Z_1$, $R_1$, $R_2$, $R_3$, $R_6$, $R_7$, $R_8$, $R_9$, $L_1$, $L_2$, $L_3$, Q, n and l are as defined in claim 1.

4. The composition of claim 1, wherein said at least one compound of the General Formulas (1) to (6) is a compound selected from the group consisting of compounds represented by the General Formula (3)

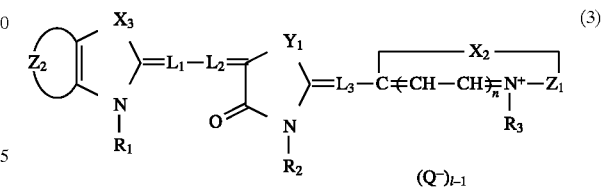

wherein $X_2$, $X_3$, $Y_1$, $Z_1$, $Z_2$, $R_1$, $R_2$, $R_3$, $L_1$, $L_2$, $L_3$, Q, n and l are as defined in claim 1.

5. The composition of claim 1, wherein said at least one compound of the General Formulas (1) to (6) is a compound selected from the group consisting of compounds represented by the General Formula (4)

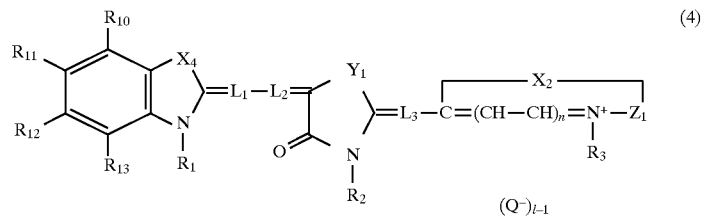

wherein $X_2$, $X_4$, $Y_1$, $Z_1$, $R_1$, $R_2$, $R_3$, $R_{10}$, $R_{11}$, $R_{12}$, $R_{13}$, $L_1$, $L_2$, $L_3$, Q, n and l are as defined in claim 1.

6. The composition of claim 2, wherein $X_1$ is O or S;

$Y_1$ is O or S;

$X_2$ is O, S, Se or —CH=CH—;

$R_1$, $R_2$ and $R_3$ each is an alkyl group having from 1 to 8 carbon atoms; and $L_1$ and $L_2$ each is a methine group.

7. The composition of claim 6, wherein $X_1$ is S;

$Y_1$ is S;

said ring formed by $Z_1$ is a benzoxazole ring, a benzothiazole ring or an α-naphthothiazole ring; said alkyl group for $R_2$ has 1 to 3 carbon atoms;

$R_4$ is a hydrogen atom; and $R_5$ is a methyl group.

8. The composition of claim 2, wherein the compound is selected from the group consisting of compounds represented by the General Formula (7)

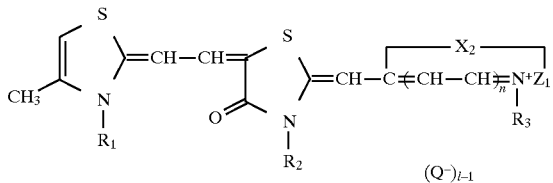

wherein

Q, n and L are as defined in claim 2;

$X_2$ is O or S;

$Z_1$ is an atomic group necessary to form a benzothiazole ring, an α-naphthothiazole ring, a 5,6-dimethylbenzothiazole ring and a 5,6-dimethoxybenzoxazole ring;

$R_1$ and $R_2$ each is a methyl group or an ethyl group; and $R_3$ is a methyl group, an ethyl group, a propyl group, a butyl group or a pentyl group.

9. The composition of claim 2, wherein the compound is selected from the group consisting of compounds represented by the General Formula (8)

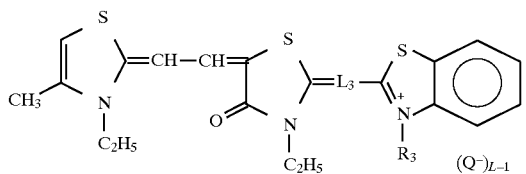

wherein $L_3$, Q and L are as defined in claim 2;

$R_3$ is an ethyl group or a propyl group, and $L_3$ and $R_3$ may combine and form a 5- or 6-membered ring.

10. The composition of claim 3, wherein $X_1$ is S; $Y_1$ is O or S; $X_2$ is O, S, Se, $CR_{16}R_{17}$ or —CH=CH—; $R_2$ is an alkyl group or an aryl group; $R_6$ and $R_7$ each is a hydrogen atom; $R_8$ and $R_9$ each is a hydrogen atom or an alkyl group; and $L_1$, $L_2$ and $L_3$ each is a methine group.

11. The composition of claim 10, wherein $Y_1$ is S; $X_2$ is O, S, Se or —CH=CH—, said ring formed by $Z_1$ is a benzoxazole ring, a naphthoxazole ring, a thiazoline ring, a thiazole ring, a benzothiazole ring, a naphthothiazole ring, a benzoselenazole ring, an indolenine ring, 2-quinoline ring or a 4-quinoline ring; said alkyl group for $R_1$ has 1 to 2 carbon atoms; $R_2$ has 1 to 3 carbon atoms and said aryl group for $R_2$ is a phenyl group; $R_3$ has 1 to 6 carbon atoms; $R_6$ and $R_7$ each is a hydrogen atom; and $R_8$ and $R_9$ each is a hydrogen atom or a methyl group. aryl group; and $L_1$ and $L_2$ each is a methine group.

12. The composition of claim 4, wherein $X_2$ is O, S, Se or —CH=CH—; $X_3$ is O or S; $Y_1$ is S; said ring formed by $Z_2$ is a naphthalene ring; $R_2$ is an alkyl group or an aryl group; and $L_1$ and $L_2$ each is a methine group.

13. The composition of claim 12, wherein said ring formed by $Z_1$ is a benzoxazole ring, a naphthoxazole ring, a thiazole ring, a benzothiazole ring, a naphthothiazole ring, a benzoselenazole ring, a 2-pyridine ring or 2-quinoline ring; said naphthalene ring formed by $Z_2$ fuses with the ring formed by $X_3$ to form an α-naphthothiazole ring, a β-naphthothiazole ring, an α-naphthoxazole ring, a β-naphthoxazole ring or a γ-naphthoxazole ring; $R_1$ and $R_3$ each has 1 to 8 carbon atoms; said alkyl group for $R_2$ has carbon atoms from 1 to 8 and said aryl group for $R_2$ has carbon atoms from 6 to 8; and $L_3$ is a methine group.

14. The composition of claim 13, wherein $X_2$ is O or S; said ring formed by $Z_1$ is a naphthoxazole ring or a naphthothiazole ring.

15. The composition of claim 14, wherein $X_2$ and $X_3$ each is S; said ring formed by $Z_1$ is a naphthothiazole ring; $R_1$ is a methyl group or an ethyl group; $R_2$ is a methyl group, an ethyl group, a vinyl methyl group, a n-propyl group, $CH_3COOCH_2CH_2$ or a phenyl group, and $R_3$ is a methyl group, an ethyl group, a n-propyl group or a hydoxyethyl group.

16. The composition of claim 13, wherein $X_2$ and $X_3$ each is S; said ring formed by $Z_1$ is an α-naphthothiazole ring, β-naphthothiazole ring or a benzothiazole ring; said naphthalene ring formed by $Z_2$ fuses with the ring formed by $X_3$ to form an α-naphthothiazole ring or a β-naphthothiazole ring; $R_1$ is a methyl group or an ethyl group; $R_2$ is a methyl group, an ethyl group, a vinyl methyl group, a n-propyl group, $CH_3COOCH_2CH_2$ or a phenyl group; and $R_3$ is a methyl group, an ethyl group, a n-propyl group or a hydoxyethyl group.

17. The composition of claim 13, wherein $X_2$ is O; $X_3$ is O or S; said ring formed by $Z_1$ is an α-naphthoxazole ring, a β-naphthoxazole ring; said naphthalene ring formed by $Z_2$ fuses with the ring formed by $X_3$ to form an α-naphthothiazole ring, a β-naphthothiazole ring or a β-naphthoxazole ring; $R_1$ is a methyl group or an ethyl group; $R_2$ is a methyl group, an ethyl group, a vinyl methyl group, a n-propyl group, $CH_3COOCH_2CH_2$ or a phenyl group; and $R_3$ is a methyl group, an ethyl group, a n-propyl group or a hydoxyethyl group.

18. The composition of claim 1 wherein said pharmaceutically acceptable carrier or diluent is a glucose or saline aqueous solution.

19. The composition of claim 1, wherein said at least one compound of the General Formulas (1) to (6) is present in said composition in an amount of 0.01% to 10% by weight based on the total weight of the composition.

20. The composition of claim 4, wherein said at least one compound is

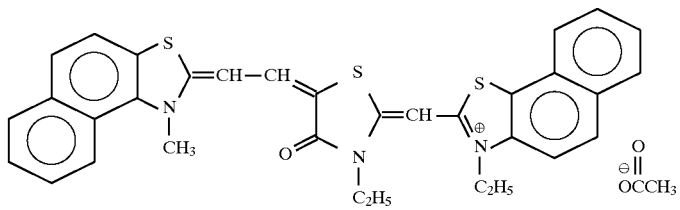

21. The composition of claim 1, wherein said at least one compound of the General Formulas (1) to (6) is a compound selected from the group consisting of compounds represented by the General Formula (5)

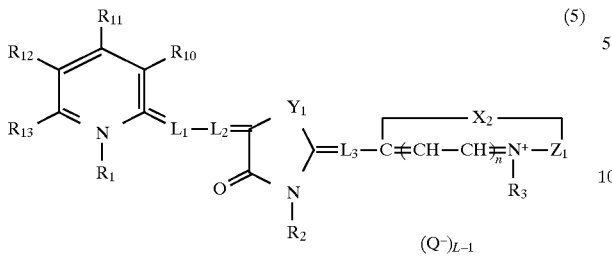

wherein $X_2$, $Y_1$, $Z_1$, $R_1$, $R_2$, $R_3$, $R_{10}$, $R_{11}$, $R_{12}$, $R_{13}$, $L_1$, $L_2$, $L_3$, Q, and n and L are as defined in claim 1.

22. The composition of claim 1, wherein said at least one compound of the General Formulas (1) to (6) is a compound selected from the group consisting of compounds represented by the General Formula (6)

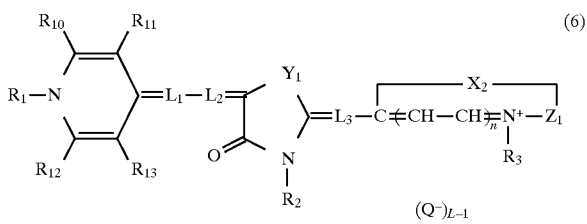

wherein $X_2$, $Y_1$, $Z_1$, $R_1$, $R_2$, $R_3$, $R_{10}$, $R_{11}$, $R_{12}$, $R_{13}$, $L_1$, $L_2$, $L_3$, Q, n and L are as defined in claim 1.

23. The composition of claim 3, wherein the compound is selected from the group consisting of compounds represented by the General Formula (9)

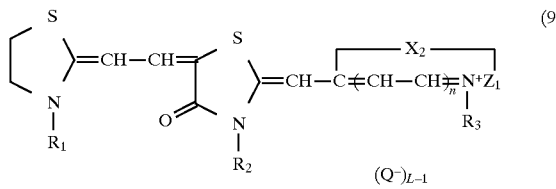

wherein

Q, n and L all have the same meaning as defined in claim 3;

$X_2$ is O, S, Se or —CH=CH—;

$Z_1$ is an atomic group necessary to form a benzoxazole ring, a naphthoxazole ring, a thiazoline ring, a benzothiazole ring, a naphthothiazole ring, a benzoselenazole ring or a 4-quinoline ring;

$R_1$ is a methyl group or an ethyl group;

$R_2$ is methyl group, an ethyl group, $CH_3OCH_2CH_2$ or a phenyl group; and $R_3$ is a methyl group, an ethyl group, a propyl group, a butyl group, n-$C_5H_{11}$, $HOCH_2CH_2$, $HOCOCH_2CH_2$, $CH_3OCH_2CH_2$, $NH_2COCH_2CH_2$, $HOCH_2(HO)CH_2$, $CH_3SO_2NHCOCH_2$ or

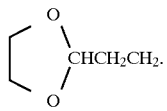

24. The composition of claim 23, wherein said ring formed by $Z_1$ is an α-naphthoxazole ring, a thiazoline ring, a benzothiazole ring, a 5-chlorobenzothiazole ring, a 5-methylbenzothiazole ring, a 5-methoxybenzothiazole ring, a 5,6-dimethoxy benzothiazole ring, a 4-methoxy benzothiazole ring, a 5,6-dichlorobenzothiazole ring, an α-naphthothiazole ring, a benzoselenazole ring, a 4-quinoline ring; $R_2$ is a methyl group or an ethyl group; and $R_3$ is a methyl group, an ethyl group or $CH_3OCH_2CH_2$.

25. The composition of claim 13, wherein $X_2$ is —CH=CH—; $X_3$ is S; said ring formed by $Z_1$ is a 4-quinoline ring; said naphthalene ring formed by $Z_2$ fuses with the ring formed by $X_3$ to form an α-naphthothiazole ring or a β-naphthothiazole ring; $R_1$ is a methyl group or an ethyl group; $R_2$ is a methyl group, an ethyl group, a vinyl methyl group, a n-propyl group, $CH_3COOCH_2CH_2$ or a phenyl group; and $R_3$ is a methyl group, an ethyl group, a n-propyl group or a hydoxyethyl group.

26. The composition of claim 5, wherein $X_2$ is O, S or —CH=CH—; $X_4$ is

$Y_1$ is S; said ring formed by $Z_1$ is a benzoxazole ring, a thiazole ring, a benzothiazole ring, a naphthothiazole ring, 2-quinoline ring or 4-quinoline ring; $R_2$ is an alkyl group or an aryl group; $R_{11}$ and $R_{12}$ each is a hydrogen atom, a halogen atom or an alkyl group; $R_{10}$ and $R_{13}$ each is a hydrogen atom; and $L_1$ and $L_2$ and $L_3$ each is a methine group.

27. The composition of claim 5, wherein $X_2$ is O, S, Se or —CH=CH—; $X_4$

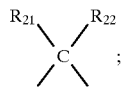

$Y_1$ is S; said ring formed by $Z_1$ is a benzoxazole ring, a naphthoxazole ring, a thiazoline ring, a thiazole ring, a benzothiazole ring, a naphthothiazole ring, a benzoselenazole ring, an indolenine ring, 2-quinoline ring or a 4-quinoline ring; $R_2$ is an alkyl group; $R_{10}$, $R_{12}$ and $R_{13}$ each is a hydrogen atom; $R_{11}$, is a hydrogen atom, a halogen atom, a nitro group, an alkylcarbonyl group, an acylamino group, an aminoalkyl group or an alkylsulfamido group; and $L_1$, $L_2$ and $L_3$ each is a methine group.

28. The composition of claim 5, wherein the compound is selected from the group consisting of compounds represented by the General Formula (10)

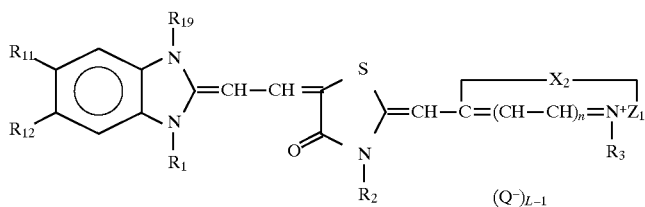

(10)

wherein

Q, n and L are as defined in claim 5;

$X_2$ is S;

$Z_1$ is an atomic group necessary to form a naphthothiazole ring;

$R_1$, $R_2$, $R_3$ and $R_{19}$ each is an alkyl group having from 1 to 8 carbon atoms;

$R_{11}$ is a hydrogen atom; and $R_{12}$ is a hydrogen atom, a halogen atom or a halogenated alkyl group.

29. The composition of claim 28, wherein said ring formed by $Z_1$ is a α-naphthoxazole ring or a β-naphthoxazole ring; $R_1$ is a methyl group, an ethyl group or $CHF_2CF_2CH_2$; $R_2$, $R_3$ and $R_{19}$ each is a methyl group or an ethyl group; and $R_{12}$ is hydrogen atom, a chlorine atom or a trifluoromethyl group.

30. The composition of claim 5, wherein the compound is selected from the group consisting of compounds represented by the General Formula (11)

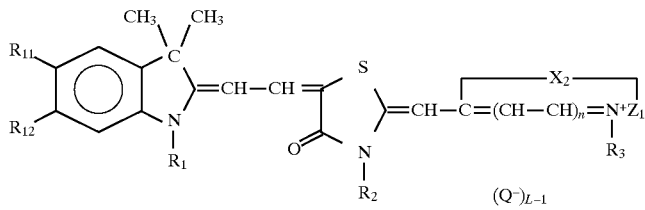

(11)

wherein

Q, n and L are as defined in claim 5;

$X_2$ is O, S or —CH=CH—;

$Z_1$ is an atomic group necessary to form a thiazole ring, a benzothiazole ring, a naphthothiazole ring, a naphthoxazole ring, a 2-quinoline ring or a 4-quinoline ring;

$R_1$, $R_2$ and $R_3$ each is an alkyl group having from 1 to 8 carbon atoms;

$R_{11}$ is a hydrogen atom or a halogen atom; and $R_{12}$ is a hydrogen atom.

31. The composition of claim 30, wherein said ring formed by $Z_1$ is 4,5-diphenylthiazole ring, a benzothiazole ring, a 6-methylbenzothiazole ring, a 5-chlorbenzothiazole ring, a 5-ethoxy-6-methylbenzothiazole ring, a α-naphthothiazole ring, a α-naphthoxazole ring or a 4-quinoline ring; $R_1$, $R_2$ and $R_3$ each is a methyl group or an ethyl group; and $R_1$, is a hydrogen atom or a chlorine atom.

32. The composition of claim 21, wherein the compound is selected from the group consisting of compounds represented by the General Formula (12)

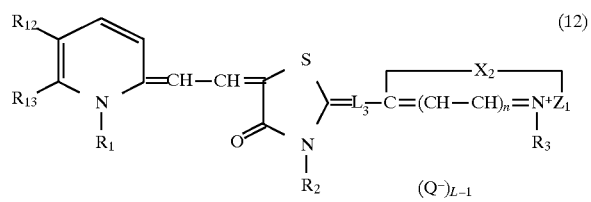

(12)

wherein $L_3$, Q, n and L are as defined in claim 21;

$X_2$ is or —CH=CH—;

$Z_1$ is an atomic group necessary to form a thiazoline ring, a benzothiazole ring, a naphthothiazole ring or a 4-quinoline ring;

$R_1$, $R_2$ and $R_3$ each is an alkyl group having from 1 to 8 carbon atoms; and $R_{12}$ and $R_{13}$ each is a hydrogen atom or an alkyl group or $R_{12}$ and $R_{13}$ may combine and form a saturated or unsaturated 6-membered ring.

33. The composition of claim 32, wherein $X_2$ is S; said ring formed by $Z_1$ is a benzothiazole ring or a naphthothiazole ring; $R_{12}$ is a hydrogen atom or a methyl group or an ethyl group; $R_{13}$ is a hydrogen atom; and $L_3$ is a methine group.

34. The composition of claim 33, wherein said ring formed by $Z_1$ is a 5,6-dimethylbenzothiazole ring or a β-naphthothiazole ring; $R_{12}$ is a hydrogen atom or a methyl group; $R_1$ and $R_3$ each is a methyl group or an ethyl group; $R_2$ is a methyl group, an ethyl group or a vinyl methyl group.

35. The composition of claim 21, wherein the compound is selected from the group consisting of compounds represented by the General Formula (13)

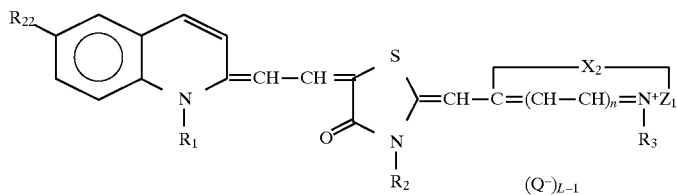

(13)

wherein

Q, n and L are as defined in claim 21;

$X_2$ is S or —CH=CH—;

$Z_1$ is an atomic group necessary to form a thiazoline ring, a benzothiazole ring, a naphthothiazole ring or a 4-quinoline ring;

$R_1$, $R_2$ and $R_3$ each is an alkyl group having from 1 to 8 carbon atoms;

$R_{22}$ is a hydrogen atom, an alkyl group, an alkoxy group or a halogen atom.

36. The composition of claim 35, wherein said ring formed by $Z_1$ is a thiazoline ring, an α-naphthothiazole ring or a 4-quinoline ring; $R_1$ and $R_3$ each is a methyl group or an ethyl group; $R_2$ is an ethyl group or a vinyl methyl group; and $R_{22}$ is a hydrogen atom, a methyl group, an ethoxy group or a chlorine atom.

37. The composition of claim 22, wherein the compound is selected from the group consisting of compounds represented by the General Formula (14)

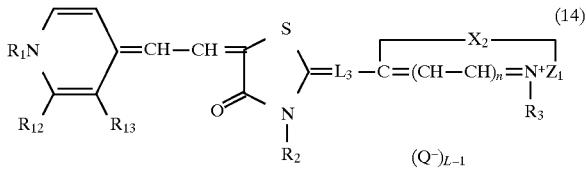

wherein $R_1$, $R_3$, $L_3$, Q, n and L are as defined in claim 22;

$X_2$ is S or —CH=CH—;

$Z_1$ is an atomic group necessary to form a benzothiazole ring, a naphthothiazole ring or a 4-quinoline ring;

$R_2$ is an alkyl group; and $R_{12}$ and $R_{13}$ each is a hydrogen atom or an alkyl group, and $R_{12}$ and $R_{13}$ may combine and form an unsaturated or saturated 6-membered ring.

38. The composition of claim 37, wherein $X_2$ is S; said ring formed by $Z_1$ is a benzothiazole ring or a naphthothiazole ring; $R_1$, $R_2$ and $R_3$ each has carbon atoms from 1 to 8; $R_{12}$ and $R_{13}$ each is a hydrogen atom; and $L_3$ is a methine group.

39. The composition of claim 38, wherein said ring formed by $Z_1$ is a benzothiazole ring; and $R_1$, $R_2$ and $R_3$ each is a methyl group or an ethyl group.

40. The composition of claim 22, wherein the compound is selected from the group consisting of compounds represented by the General Formula (15)

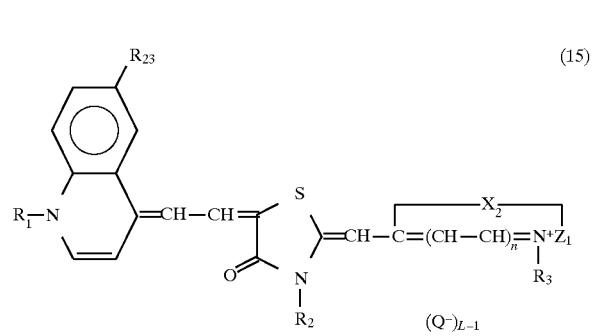

wherein

Q, n and L are as defined in claim 22;

$X_2$ is S or —CH=CH—;

$Z_1$ is an atomic group necessary to form a benzothiazole ring, a naphthothiazole ring or a 4-quinoline ring;

$R_1$, $R_2$ and $R_3$ each is an alkyl group having from 1 to 8 carbon atoms; and $R_{23}$ is a hydrogen atom, an alkoxy group, an acylamino group, a halogen atom or a halogenated alkyl group.

41. The composition of claim 40, wherein $X_2$ is S; said ring formed by $Z_1$ is an α-naphthothiazole ring or a β-naphthothiazole ring; $R_1$ and $R_3$ each is a methyl group or an ethyl group; $R_2$ is a methyl group, an ethyl group or a vinyl methyl group; and $R_{23}$ is a hydrogen atom.

42. A method for treating cancer comprising administering a therapeutically effective amount of the composition of claim 1 to a host afflicted with cancer sentitive to said composition.

43. The method of claim 42, wherein said administering is orally, intravenously, intraperitoneally, intramuscularly or intravesicularly.

44. The method of claim 43, wherein said administering is intraperitoneally or intravenously.

45. The method of claim 42, wherein said cancer is a melanoma, a hepatoma, a glioma, a neuroblastoma, a sarcoma or a carcinoma of the lung, colon, pancreas, breast, bladder ovary, testis, prostate, cervix, stomach or small intestine.

46. The method of claim 45, wherein said cancer is a carcinoma.

47. The method of claim 45, wherein said cancer is a melanoma.

48. The method of claim 42, wherein said cancer is colon cancer.

49. The method of claim 42, wherein said host is a mammal.

50. The method of claim 49, wherein said mammal is a human.

* * * * *